United States Patent
Facchetti et al.

(10) Patent No.: US 9,711,728 B1
(45) Date of Patent: Jul. 18, 2017

(54) FUSED THIOPHENE-BASED CONJUGATED POLYMERS AND THEIR USE IN OPTOELECTRONIC DEVICES

(71) Applicants: Northwestern University, Evanston, IL (US); Polyera Corporation, Skokie, IL (US)

(72) Inventors: Antonio Facchetti, Chicago, IL (US); Tobin J. Marks, Evanston, IL (US); Atsuro Takai, Evanston, IL (US); Mark Seger, Chicago, IL (US); Zhihua Chen, Skokie, IL (US)

(73) Assignees: Northwestern University, Evanston, IL (US); Flexterra, Inc., Skokie, IL (US)

( * ) Notice: Subject to any disclaimer, the term of this patent is extended or adjusted under 35 U.S.C. 154(b) by 0 days.

(21) Appl. No.: 14/884,986

(22) Filed: Oct. 16, 2015

Related U.S. Application Data

(63) Continuation of application No. 14/520,304, filed on Oct. 21, 2014, now Pat. No. 9,178,160.

(60) Provisional application No. 61/893,862, filed on Oct. 21, 2013.

(51) Int. Cl.
| | |
|---|---|
| *C07D 333/54* | (2006.01) |
| *H01L 51/42* | (2006.01) |
| *H01L 51/00* | (2006.01) |
| *C08G 61/12* | (2006.01) |
| *H01L 51/05* | (2006.01) |
| *H01L 51/44* | (2006.01) |

(52) U.S. Cl.
CPC ........ *H01L 51/0043* (2013.01); *C08G 61/122* (2013.01); *C08G 61/126* (2013.01); *H01L 51/0035* (2013.01); *H01L 51/0036* (2013.01); *C08G 2261/12* (2013.01); *C08G 2261/122* (2013.01); *C08G 2261/1412* (2013.01); *C08G 2261/18* (2013.01); *C08G 2261/3223* (2013.01); *C08G 2261/3241* (2013.01); *C08G 2261/3243* (2013.01); *C08G 2261/3246* (2013.01); *C08G 2261/91* (2013.01); *H01L 51/0512* (2013.01); *H01L 51/4253* (2013.01); *H01L 51/441* (2013.01)

(58) Field of Classification Search
CPC ........ C07D 333/54; H01L 51/99; H01L 51/42
See application file for complete search history.

(56) References Cited

U.S. PATENT DOCUMENTS

| | | | |
|---|---|---|---|
| 2007/0073052 A1 | 3/2007 | Velusamy et al. | ................. 540/1 |
| 2011/0288300 A1 | 11/2011 | Wu et al. | ......................... 546/12 |

FOREIGN PATENT DOCUMENTS

CN    101497746    8/2009

OTHER PUBLICATIONS

Hong et al., 1999, caplus an 1999:784563.*
Fukazawa et al., 2013, caplus an 2013:1279708.*
Rahman et al., 2006, caplus an 2006:169726.*
Ruiz Delgado et al., 2008, caplus an 2008:141146.*
Brisset et al., "Linearly extended hybrid tetrathiafulvalene analogues with bridged dithienylethylene pi-conjugating spacers," *J. Mater. Chem.*, 7(10): 2027-2032, 1997.
Blanchard et al., "Electrosynthesis of a Low Band Gap pi-Conjugated Polymer from a Multibridged Dithienylethylene," *J. Org. Chem.*, 63: 7107-7110, 1998.
Gilman et al., caplus an 1958:6337 (1958).

* cited by examiner

*Primary Examiner* — Sun Jae Yoo
(74) *Attorney, Agent, or Firm* — Karen K. Chan

(57) ABSTRACT

The present teachings relate to polymeric compounds and their use as organic semiconductors in organic and hybrid optical, optoelectronic, and/or electronic devices such as photovoltaic cells, light emitting diodes, light emitting transistors, and field effect transistors. The disclosed compounds generally include as repeating units at least one annulated thienyl-vinylene-thienyl (TVT) unit and at least one other pi-conjugated unit. The annulated TVT unit can be represented by the formula:

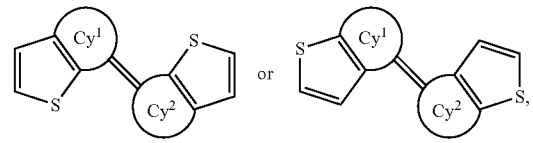

where $Cy^1$ and $Cy^2$ can be a five- or six-membered carbocyclic ring. The annulated TVT unit can be optionally substituted at any available ring atom(s), and can be covalently linked to the other pi-conjugated unit via either the thiophene rings or the carbocyclic rings $Cy^1$ and $Cy^2$. The other pi-conjugated unit can be a conjugated linear linker including one or more unsaturated bonds, or a conjugated cyclic linker including one or more carbocyclic and/or heterocyclic rings.

20 Claims, 3 Drawing Sheets

FUSED THIOPHENE-BASED CONJUGATED POLYMERS AND THEIR USE IN OPTOELECTRONIC DEVICES

CROSS-REFERENCE TO RELATED APPLICATIONS

This application is a continuation of U.S. patent application Ser. No. 14/520,304, filed on Oct. 21, 2014, which claims priority to and the benefit of U.S. Provisional Patent Application Ser. No. 61/893,862, filed on Oct. 21, 2013, the disclosure of each of which is incorporated by reference herein in its entirety.

STATEMENT REGARDING FEDERALLY SPONSORED RESEARCH OR DEVELOPMENT

This invention was made with government support under grant number DE-SC0001059 awarded by the Department of Energy. The government has certain rights in the invention.

BACKGROUND

A new generation of optoelectronic devices such as organic photovoltaic (OPV) devices, organic light emitting transistors (OLETs), organic light emitting diodes (OLEDs), organic thin film transistors (OTFTs), printable circuits, electrochemical capacitors, and sensors are built upon organic semiconductors as their active components. To enable high device efficiencies such as large charge carrier mobilities (μ) needed for transistor/circuit operations, or efficient exciton formation/splitting that is necessary for OLED/OPV operations, it is desirable that both p-type and n-type organic semiconductor materials are available. Furthermore, these organic semiconductor-based devices should exhibit satisfactory stability in ambient conditions and should be processable in a cost-effective manner. For example, a benchmark polymer, regioregular poly(3-hexylthiophene) (rr-P3HT), can provide hole mobilities in the order of about 0.1 $cm^2/Vs$ and current modulation in the order of about $10^5$ or greater, which is close to amorphous silicon.

Bulk heterojunction (BHJ) solar cells commonly are considered the most promising OPV structures because they can be fabricated using roll-to-roll and large-scale production. BHJ solar cells include a photoactive layer disposed between an anode and a cathode, where the photoactive layer is composed of a blend film including a donor material and an acceptor material. State-of-the-art BHJ solar cells use fullerene-based compounds as the acceptor material. Typical fullerenes include C60 or C70 "bucky ball" compounds functionalized with solubilizing side chains such as [6,6]-phenyl-$C_{61}$-butyric acid methyl ester (PCBM) or [6,6]-phenyl-$C_{71}$-butyric acid methyl ester ($PC_{71}BM$). The most common donor material used in BHJ solar cells is poly(3-hexylthiophene) (P3HT). However, it is well known that P3HT-based cell have limited efficiency due to poor light absorption above 500 nm. Furthermore, P3HT also has poor air stability.

Accordingly, the art desires new polymeric semiconducting materials as active layers in various optoelectronic devices.

SUMMARY

In light of the foregoing, the present teachings provide novel polymeric compounds that can be used as organic semiconductor materials. More specifically, the present polymers include at least one annulated thienyl-vinylene-thienyl (TVT) unit and at least one other pi-conjugated unit as repeating units. Also provided are associated devices and related methods for the preparation and use of these compounds. The present compounds can exhibit properties such as optimized optical absorption, good charge transport characteristics and chemical stability in ambient conditions, low-temperature processability, large solubility in common solvents, and processing versatility (e.g., via various solution processes). As a result, optoelectronic devices such as OPV cells that incorporate one or more of the present compounds as a photoactive layer can exhibit high performance in ambient conditions, for example, demonstrating one or more of low band-gap, high fill factor, high open circuit voltage, and high power conversion efficiency, and preferably all of these criteria. Similarly, other organic semiconductor-based devices such as OTFTs can be fabricated efficiently using the organic semiconductor materials described herein.

The present teachings also provide methods of preparing such compounds and semiconductor materials, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF DRAWINGS

It should be understood that the drawings described below are for illustration purposes only. The drawings are not necessarily to scale, with emphasis generally being placed upon illustrating the principles of the present teachings. The drawings are not intended to limit the scope of the present teachings in any way.

DETAILED DESCRIPTION

Figure 1:
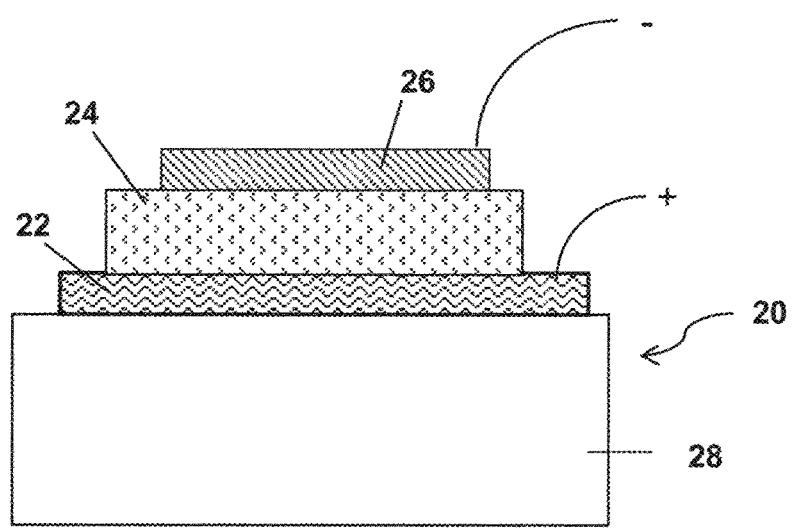
FIG. 1 illustrates a representative organic photovoltaic device (also known as a solar cell) structure, which can incorporate one or more polymeric compounds of the present teachings in its photoactive layer (as donor and/or acceptor materials).

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "p-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about $10^{-5}$ cm$^2$/Vs. In the case of field-effect devices, a p-type semiconductor also can exhibit a current on/off ratio of greater than about 10.

As used herein, an "n-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about $10^{-5}$ cm$^2$/Vs. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when a transistor incorporating the compound as its semiconducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period.

As used herein, fill factor (FF) is the ratio (given as a percentage) of the actual maximum obtainable power, ($P_m$ or $V_{mp}*J_{mp}$), to the theoretical (not actually obtainable) power, ($J_{sc}*V_{oc}$). Accordingly, FF can be determined using the equation:

$$FF=(V_{mp}*J_{mp})/(J_{sc}*V_{oc})$$

where $J_{mp}$ and $V_{mp}$ represent the current density and voltage at the maximum power point ($P_m$), respectively, this point being obtained by varying the resistance in the circuit until J*V is at its greatest value; and $J_{sc}$ and $V_{oc}$ represent the short circuit current and the open circuit voltage, respectively. Fill factor is a key parameter in evaluating the performance of solar cells. Commercial solar cells typically have a fill factor of about 0.60% or greater.

As used herein, the open-circuit voltage ($V_{oc}$) is the difference in the electrical potentials between the anode and the cathode of a device when there is no external load connected.

As used herein, the power conversion efficiency (PCE) of a solar cell is the percentage of power converted from incident light to electrical power. The PCE of a solar cell can be calculated by dividing the maximum power point ($P_m$) by the input light irradiance (E, in W/m$^2$) under standard test conditions (STC) and the surface area of the solar cell (A, in m$^2$). STC typically refers to a temperature of 25° C. and an irradiance of 1000 W/m$^2$ with an air mass 1.5 (AM 1.5) spectrum.

As used herein, a component (such as a thin film layer) can be considered "photoactive" if it contains one or more compounds that can absorb photons to produce excitons for the generation of a photocurrent.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, and blade coating.

As used herein, a "semicrystalline polymer" refers to a polymer that has an inherent tendency to crystallize at least partially either when cooled from a melted state or deposited from solution, when subjected to kinetically favorable conditions such as slow cooling, or low solvent evaporation rate and so forth. The crystallization or lack thereof can be readily identified by using several analytical methods, for example, differential scanning calorimetry (DSC) and/or X-ray diffraction (XRD).

As used herein, "annealing" refers to a post-deposition heat treatment to the semicrystalline polymer film in ambient or under reduced/increased pressure for a time duration of more than 100 seconds, and "annealing temperature" refers to the maximum temperature that the polymer film is exposed to for at least 60 seconds during this process of annealing. Without wishing to be bound by any particular theory, it is believed that annealing can result in an increase of crystallinity in the polymer film, where possible, thereby increasing field effect mobility. The increase in crystallinity can be monitored by several methods, for example, by comparing the differential scanning calorimetry (DSC) or X-ray diffraction (XRD) measurements of the as-deposited and the annealed films.

As used herein, a "polymeric compound" (or "polymer") refers to a molecule including a plurality of one or more repeating units connected by covalent chemical bonds. A polymeric compound can be represented by the general formula:

wherein M is the repeating unit or monomer. The polymeric compound can have only one type of repeating unit as well as two or more types of different repeating units. When a polymeric compound has only one type of repeating unit, it can be referred to as a homopolymer. When a polymeric compound has two or more types of different repeating units, the term "copolymer" or "copolymeric compound" can be used instead. For example, a copolymeric compound can include repeating units

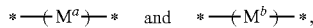

where $M^a$ and $M^b$ represent two different repeating units. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer. For example, the general formula:

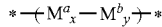

can be used to represent a copolymer of $M^a$ and $M^b$ having x mole fraction of $M^a$ and y mole fraction of $M^b$ in the copolymer, where the manner in which comonomers $M^a$ and $M^b$ is repeated can be alternating, random, regiorandom, regioregular, or in blocks. In addition to its composition, a polymeric compound can be further characterized by its degree of polymerization (n) and molar mass (e.g., number average molecular weight ($M_n$) and/or weight average molecular weight ($M_w$) depending on the measuring technique(s)).

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, iso-butyl, sec-butyl, tert-butyl), pentyl groups (e.g., n-pentyl, iso-pentyl, neo-pentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula —$C_sH_{2s+1-t}X^0_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxyl, hexoxyl groups, and the like. The alkyl group in the —O-alkyl group can be substituted as described herein.

As used herein, "alkylthio" refers to an —S— alkyl group. Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and optionally can be substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which optionally can be substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which optionally can be substituted as described herein.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5] decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., $—C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an -alkyl-aryl group, where the arylalkyl group is covalently linked to the defined chemical structure via the alkyl group. An arylalkyl group is within the definition of a $—Y—C_{6-14}$ aryl group, where Y is as defined herein. An example of an arylalkyl group is a benzyl group ($—CH_2—C_6H_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

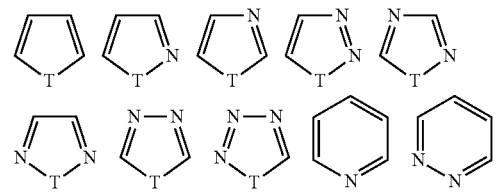

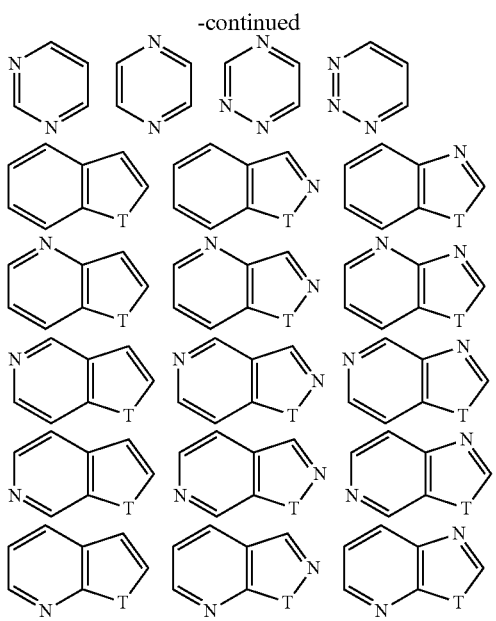

where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent C$_{1-20}$ alkyl group (e.g., a methylene group), a divalent C$_{2-20}$ alkenyl group (e.g., a vinylyl group), a divalent C$_{2-20}$ alkynyl group (e.g., an ethynylyl group). a divalent C$_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —NO$_2$, —CN, —NC, —S(R$^0$)$_2^+$, —N(R$^0$)$_3^+$, —SO$_3$H, —SO$_2$R$^0$, —SO$_3$R$^0$, —SO$_2$NHR$^0$, —SO$_2$N(R$^0$)$_2$, —COOH, —COR$^0$, —COOR$^0$, —CONHR$^0$, —CON(R$^0$)$_2$, C$_{1-40}$ haloalkyl groups, C$_{6-14}$ aryl groups, and 5-14 membered electron-poor heteroaryl groups; where R$^0$ is a C$_{1-20}$ alkyl group, a C$_{2-20}$ alkenyl group, a C$_{2-20}$ alkynyl group, a C$_{1-20}$ haloalkyl group, a C$_{1-20}$ alkoxy group, a C$_{6-14}$ aryl group, a C$_{3-14}$ cycloalkyl group, a 3-14 membered cycloheteroalkyl group, and a 5-14 membered heteroaryl group, each of which can be optionally substituted as described herein. For example, each of the C$_{1-20}$ alkyl group, the C$_{2-20}$ alkenyl group, the C$_{2-20}$ alkynyl group, the C$_{1-20}$ haloalkyl group, the C$_{1-20}$ alkoxy group, the C$_{6-14}$ aryl group, the C$_{3-14}$ cycloalkyl group, the 3-14 membered cycloheteroalkyl group, and the 5-14 membered heteroaryl group can be optionally substituted with 1-5 small electron-withdrawing groups such as F, Cl, Br, —NO$_2$, —CN, —NC, —S(R$^0$)$_2^+$, —N(R$^0$)$_3^+$, —SO$_3$H, —SO$_2$R$^0$, —SO$_3$R$^0$, —SO$_2$NHR$^0$, —SO$_2$N(R$^0$)$_2$, —COOH, —COR$^0$, —COOR$^0$, —CONHR$^0$, and —CON(R$^0$)$_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include —OH, —OR$^0$, —NH$_2$, —NHR$^0$, —N(R$^0$)$_2$, and 5-14 membered electron-rich heteroaryl groups, where R$^0$ is a C$_{1-20}$ alkyl group, a C$_{2-20}$ alkenyl group, a C$_{2-20}$ alkynyl group, a C$_{6-14}$ aryl group, or a C$_{3-14}$ cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and geometric isomers (diastereomers). The present teachings include such optical and geometric isomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one regioisomer includes any other regioisomers and any regioisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

Throughout the specification, structures may or may not be presented with chemical names. Where any question arises as to nomenclature, the structure prevails.

The present teachings relate to polymeric compounds that can be used as organic semiconductor materials. The present compounds can have good solubility in various common organic solvents and good stability in air. When incorporated into optical, electronic or optoelectronic devices including, but not limited to, organic photovoltaic or solar cells, organic light emitting diodes, and organic field effect transistors, the present compounds can confer various desirable performance properties.

More specifically, the present teachings provide polymers (or polymeric compounds) including as repeating units at least one annulated thienyl-vinylene-thienyl (TVT) unit and at least one other pi-conjugated unit. The annulated TVT unit can be represented by the formula:

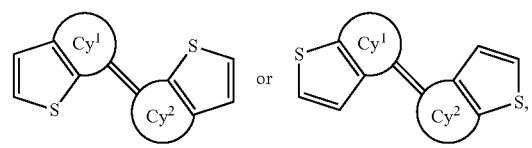

where $Cy^1$ and $Cy^2$ can be a five- or six-membered saturated or unsaturated carbocyclic ring. The annulated TVT unit can be optionally substituted at any available ring atom(s) (e.g., with 1-14 groups each independently selected from halogen, CN, a $C_{1-40}$ alkyl group, a $C_{2-40}$ alkenyl group, and a $C_{1-40}$ haloalkyl group), and can be covalently linked to the other pi-conjugated unit via either the thiophene rings or the carbocyclic rings $Cy^1$ and $Cy^2$. The other pi-conjugated unit can be a conjugated linear linker including one or more unsaturated bonds, or a conjugated cyclic linker including one or more carbocyclic and/or heterocyclic rings which may be fused or covalently linked to each other.

In some embodiments, the annulated TVT unit can be covalently linked to the other pi-conjugated unit via the thiophene ring. For example, the present polymer can include an annulated TVT unit selected from:

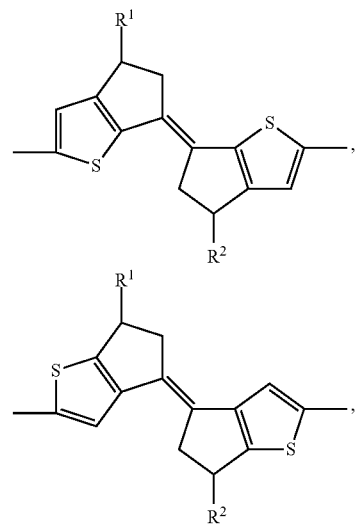

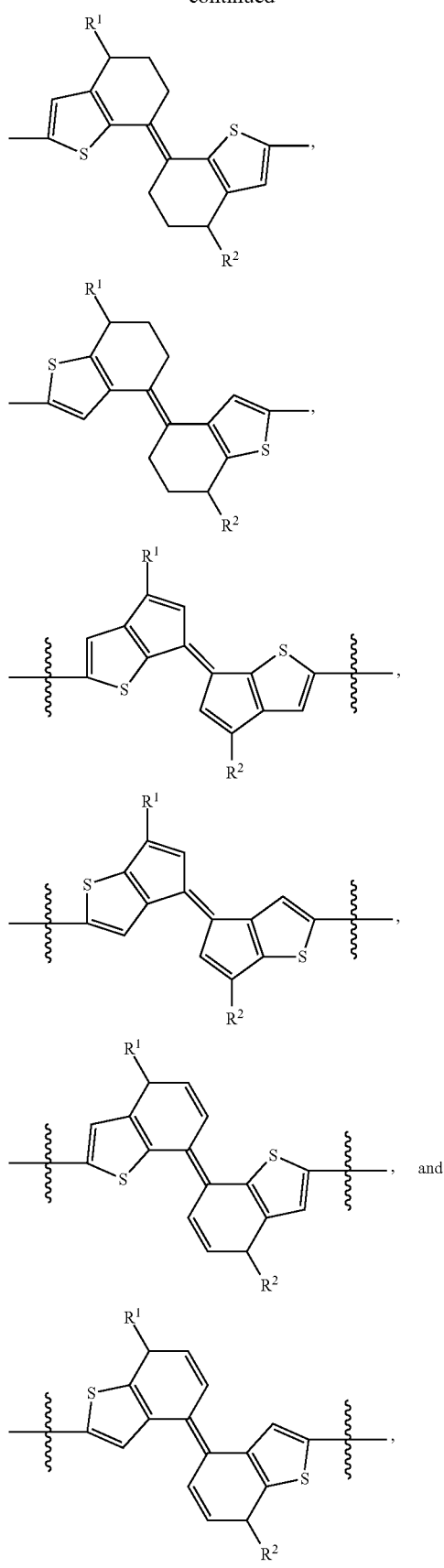

where $R^1$ and $R^2$ independently are selected from the group consisting of H, halogen, CN, a $C_{1-40}$ alkyl group, a $C_{2-40}$ alkenyl group, and a $C_{1-40}$ haloalkyl group.

In some embodiments, the annulated TVT unit can be covalently linked to the other pi-conjugated unit via the five- or six-membered carbocyclic ring. For example, the present polymer can include an annulated TVT unit selected from:

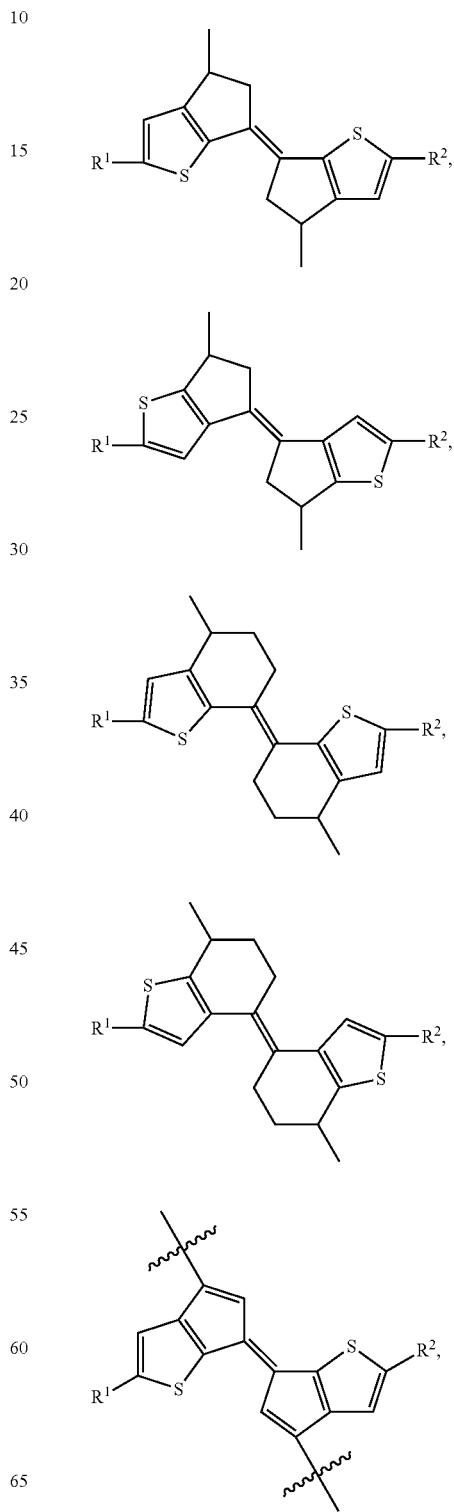

-continued

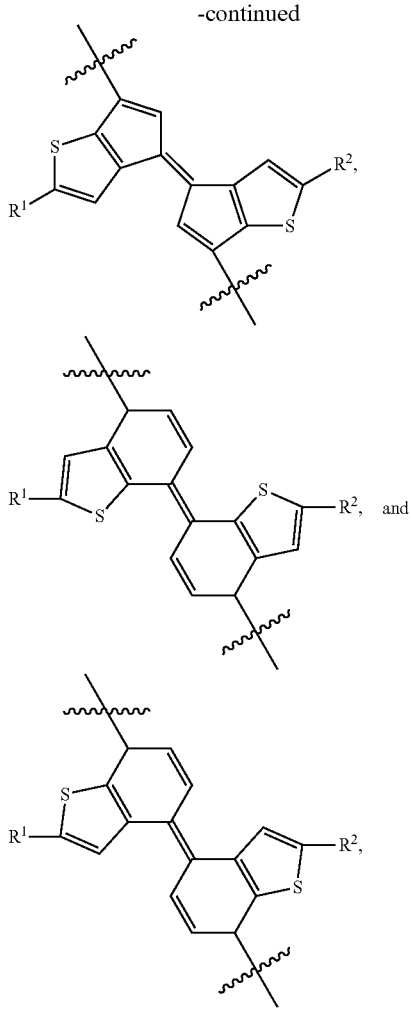

where R¹ and R² independently are selected from the group consisting of H, halogen, CN, a $C_{1-40}$ alkyl group, a $C_{2-40}$ alkenyl group, and a $C_{1-40}$ haloalkyl group.

In some embodiments, the present polymer can have a repeating unit of the formula:

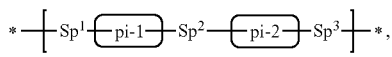

wherein the annulated TVT unit described above is present as pi-1, pi-2 is a covalent bond or an optionally substituted conjugated polycyclic moiety; and Sp¹, Sp², and Sp³ independently are a covalent bond or a conjugated spacer group comprising at least one of a conjugated linear linker and an optionally substituted conjugated monocyclic moiety; provided at least one of pi-2, Sp¹, Sp², and Sp³ is not a covalent bond.

The conjugated spacer groups Sp¹, Sp², and Sp³ can be identical or different and independently can be selected from the group consisting of:

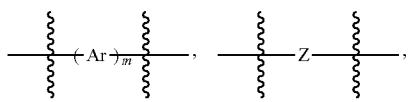

-continued

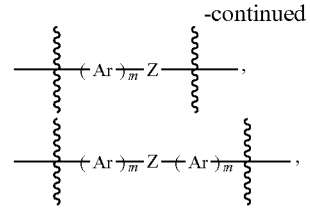

and a covalent bond, wherein each Ar independently is an optionally substituted conjugated monocyclic moiety; Z is a conjugated linear linker; and m is 1, 2, 3, 4 or 5.

In various embodiments, each Ar independently can be an optionally substituted monocyclic 5-membered or 6-membered aryl or heteroaryl group. For example, Ar can be selected from the group consisting of a phenyl group, a thienyl group, a thiazolyl group, an isothiazolyl group, a thiadiazolyl group, a furyl group, an oxazolyl group, an isoxazolyl group, an oxadiazolyl group, a pyrrolyl group, a triazolyl group, a tetrazolyl group, a pyrazolyl group, an imidazolyl group, a pyridyl group, a pyrimidyl group, a pyridazinyl group, and a pyrazinyl group, each of which optionally can be substituted with 1-4 R³ groups independently selected from a halogen, CN, oxo, $=C(CN)_2$, a $C_{1-40}$ alkyl group, a $C_{1-40}$ haloalkyl group, a $C_{1-40}$ alkoxy group, and a $C_{1-40}$ alkylthio group.

In various embodiments, Z can be selected from the group consisting of:

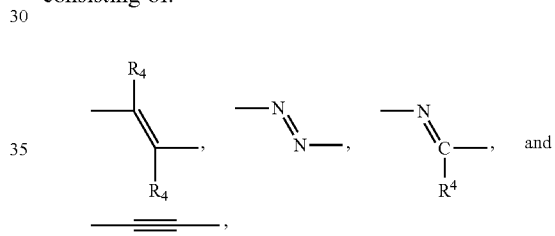

wherein each R⁴ independently is selected from the group consisting of H, a halogen, CN, a $C_{1-40}$ alkyl group, a $C_{1-40}$ haloalkyl group, a $C_{1-40}$ alkoxy group, and a $C_{1-40}$ alkylthio group.

In certain embodiments, Sp¹ and Sp² can be

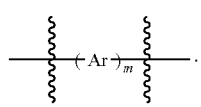

Accordingly, certain embodiments of the present polymers can have a repeating unit of the formula:

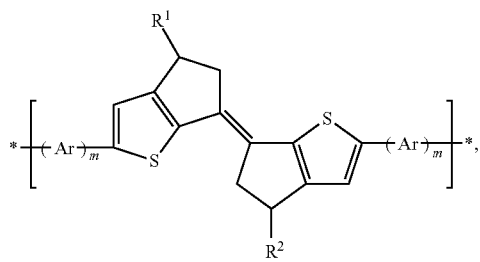

-continued

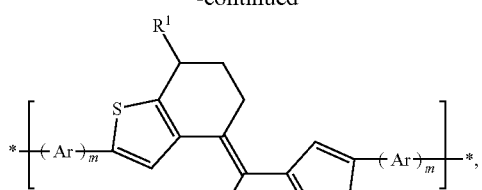

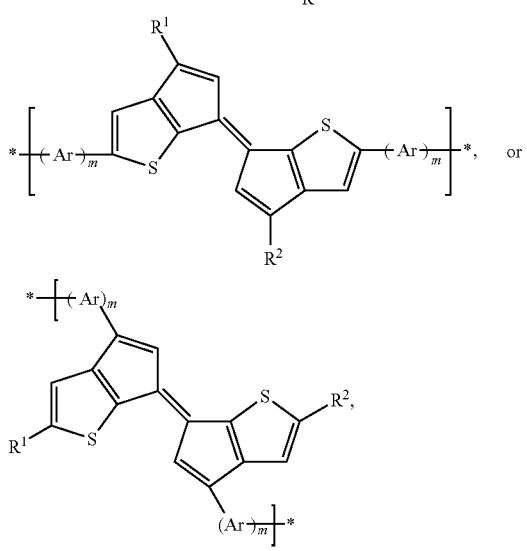

where Ar, $R^1$, $R^2$, and m are as defined herein.

In particular embodiments, Ar can be a thienyl group optionally substituted with 1-2 functional groups independently selected from the group consisting of F, Cl, —CN, R, —OR, —SR, —C(O)R, —OC(O)R, and —C(O)OR; wherein R is selected from the group consisting of a $C_{1-40}$ alkyl group, a $C_{1-40}$ haloalkyl group, a $C_{2-40}$ alkenyl group, and a $C_{2-40}$ alkynyl group. Accordingly, particular embodiments of the present polymers can have a repeating unit of the formula:

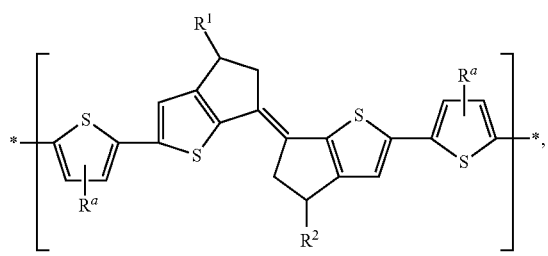

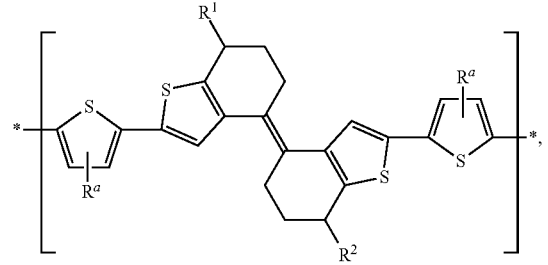

-continued

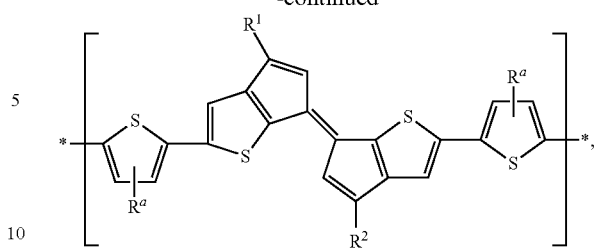

or

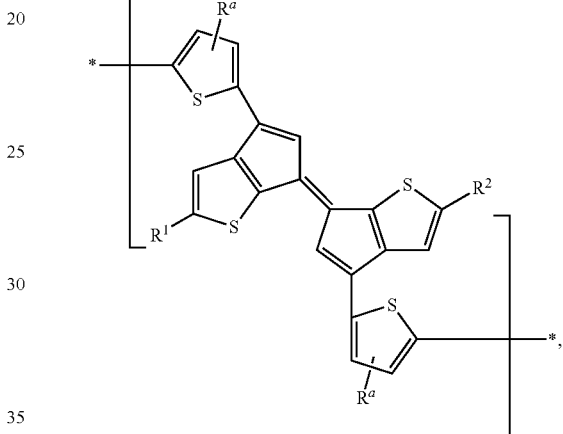

wherein $R^a$ is selected from the group consisting of H, F, Cl, —CN, R, —OR, —SR, —C(O)R, —OC(O)R, and —C(O)OR; wherein R is selected from the group consisting of a $C_{1-40}$ alkyl group, a $C_{1-40}$ haloalkyl group, a $C_{2-40}$ alkenyl group, and a $C_{2-40}$ alkynyl group.

In some embodiments, $Sp^1$ and $Sp^2$ can be

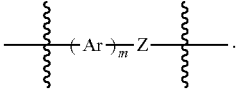

Accordingly, certain embodiments of the present polymers can have a repeating unit of the formula:

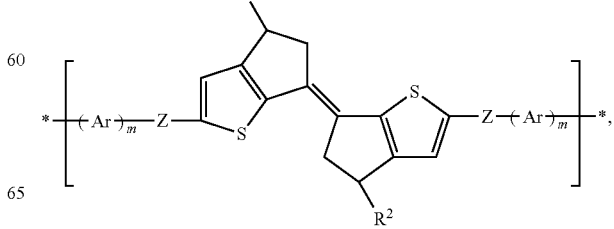

-continued

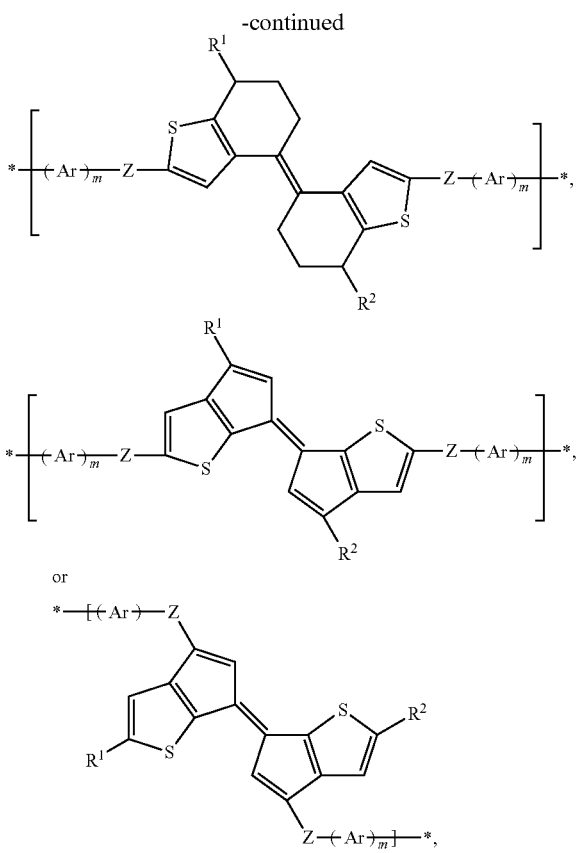

where Ar, Z, $R^1$, $R^2$, and m are as defined herein. For example, Ar can be a thienyl group optionally substituted with 1-2 functional groups independently selected from the group consisting of F, Cl, —CN, R, —OR, —SR, —C(O)R, —OC(O)R, and —C(O)OR; where R is selected from the group consisting of a $C_{1-40}$ alkyl group, a $C_{1-40}$ haloalkyl group, a $C_{2-40}$ alkenyl group, and a $C_{2-40}$ alkynyl group; and Z can be —$CR^4$=$CR^4$—, where each $R^4$ independently can be selected from the group consisting of H, a halogen, CN, a $C_{1-40}$ alkyl group, and a $C_{1-40}$ haloalkyl group.

In certain embodiments, one of $Sp^1$, $Sp^2$, and $Sp^3$ can have the formula:

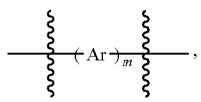

while the other two of $Sp^1$, $Sp^2$, and $Sp^3$ are each a covalent bond. In particular embodiments, the spacer group that is not a covalent bond can be an electron-donor unit having the formula:

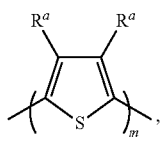

wherein m can be 3, 4 or 5, and $R^a$ is selected from the group consisting of H, F, Cl, —CN, R, —OR, —SR, —C(O)R, —OC(O)R, and —C(O)OR; wherein R is selected from the group consisting of a $C_{1-40}$ alkyl group, a $C_{1-40}$ haloalkyl group, a $C_{2-40}$ alkenyl group, and a $C_{2-40}$ alkynyl group. For example, in certain embodiments, each $R^a$ can be H; while in certain embodiments, at least one of the $R^a$ groups can be F, Cl, —CN, R, —OR, —SR, —C(O)R, —OC(O)R, and —C(O)OR, wherein R is as defined herein.

To illustrate, in certain embodiments, the electron-donating spacer group can comprise a terthiophene, where optionally the terthiophene can be selected from the group consisting of:

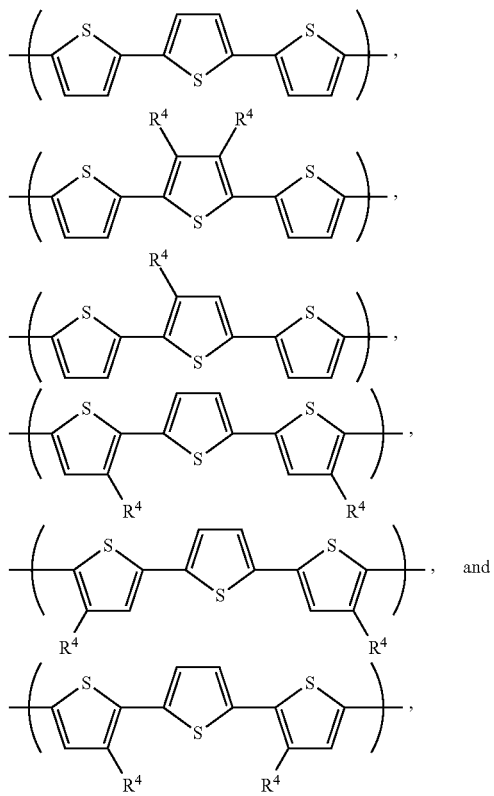

wherein $R^4$, at each occurrence, independently can be selected from the group consisting of a -L-$C_{6-40}$ alkyl group, a -L-$C_{6-40}$ alkenyl group, and a -L-$C_{6-40}$ haloalkyl group, wherein L, at each occurrence, can be selected from the group consisting of O, S, and a covalent bond.

In other embodiments, the electron-donating spacer group can comprise a quaterthiophene, where optionally the quaterthiophene can be selected from the group consisting of:

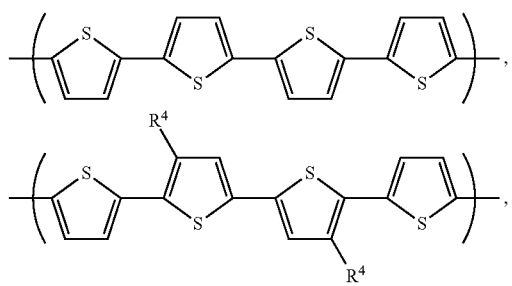

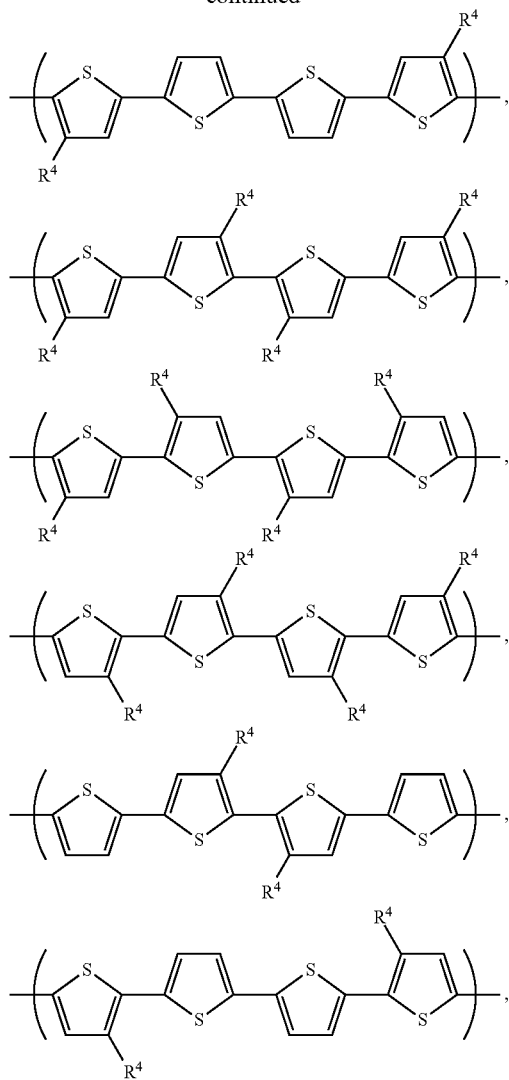

wherein R⁴, at each occurrence, independently can be selected from the group consisting of a -L-$C_{6-40}$ alkyl group, a -L-$C_{6-40}$ alkenyl group, and a -L-$C_{6-40}$ haloalkyl group, wherein L, at each occurrence, can be selected from the group consisting of O, S, and a covalent bond.

In various embodiments of the present polymers, pi-2 can be a covalent bond. Accordingly, certain embodiments of the present polymers can be represented by a formula selected from the group consisting of:

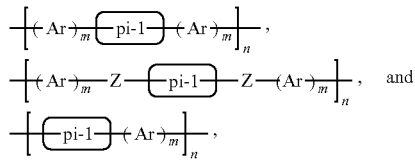

where Ar, Z, and m are as defined herein. The degree of polymerization (n) can be an integer in the range of 2 to 10,000, for example, in the range of 3 and 5,000, preferably between 5 and 5,000, and more preferably, between 10 and 5,000. For example, particular embodiments of the present polymers can have a formula selected from the group consisting of:

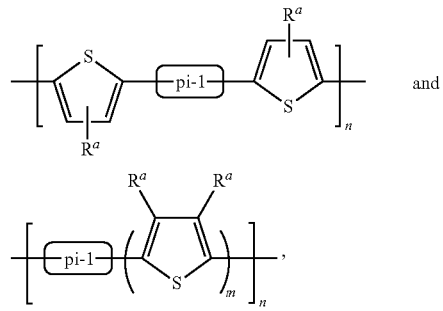

where each $R^a$ independently is selected from the group consisting of H, F, Cl, —CN, R, —OR, —SR, —C(O)R, —OC(O)R, and —C(O)OR; wherein R is selected from the group consisting of a $C_{1-40}$ alkyl group, a $C_{1-40}$ haloalkyl group, a $C_{2-40}$ alkenyl group, and a $C_{2-40}$ alkynyl group; m is 3, 4 or 5; and n is an integer in the range of 3 and 5,000.

Other embodiments of the present polymers can include one or more pi-2 moieties, where each pi-2 is an optionally substituted conjugated polycyclic moiety. For example, each pi-2 independently can be a conjugated polycyclic moiety selected from the group consisting of:

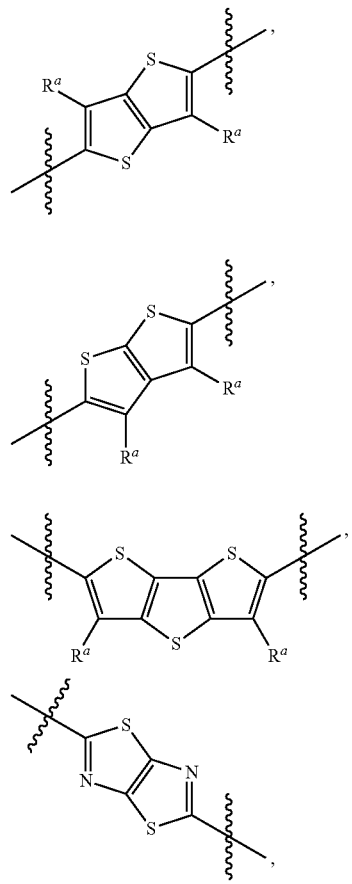

23
-continued
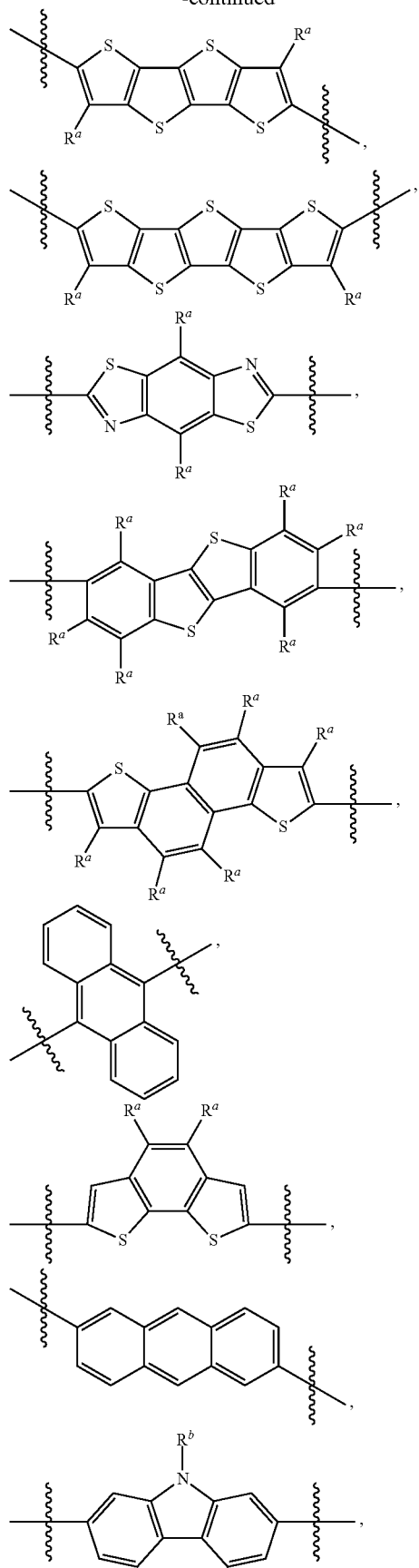
24
-continued
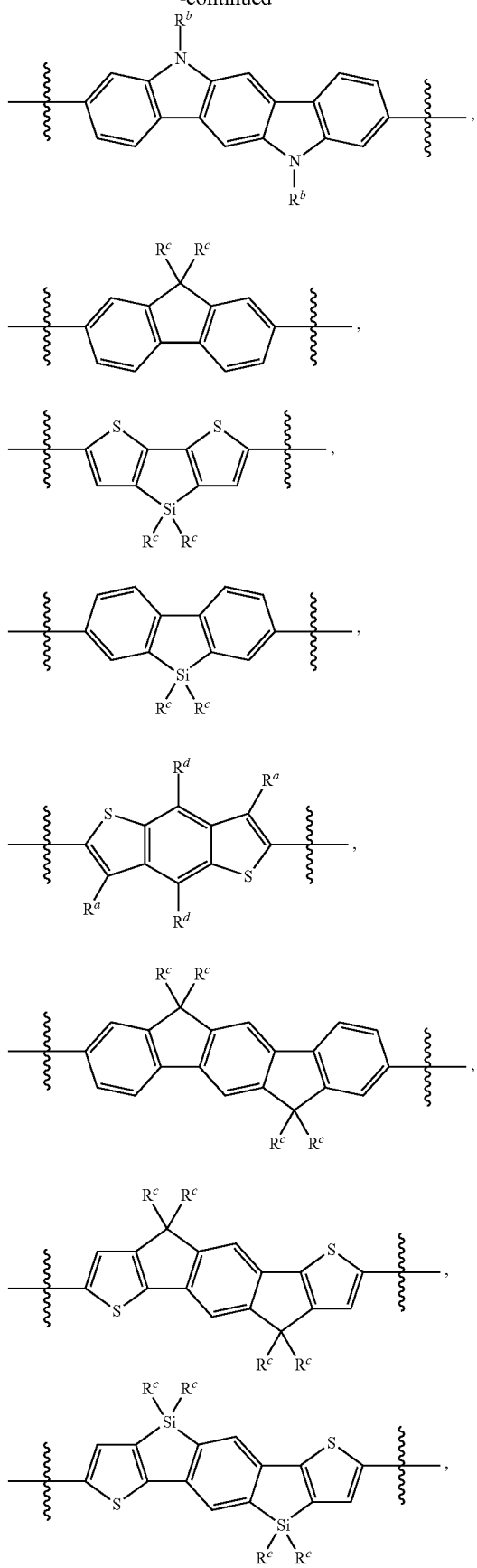

-continued
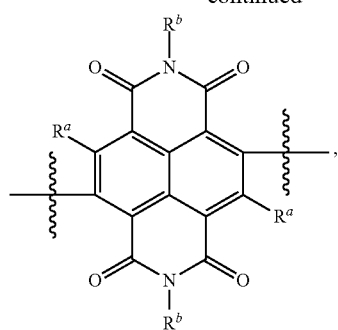
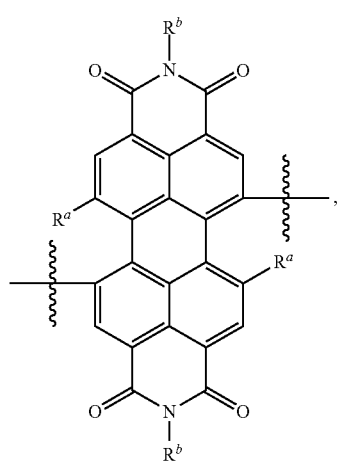
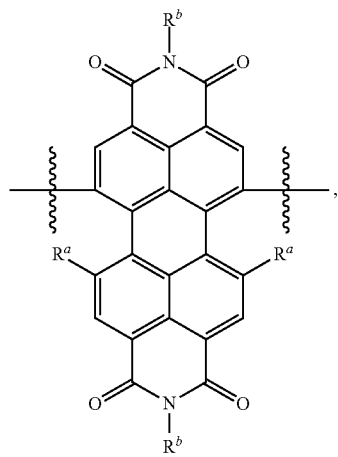
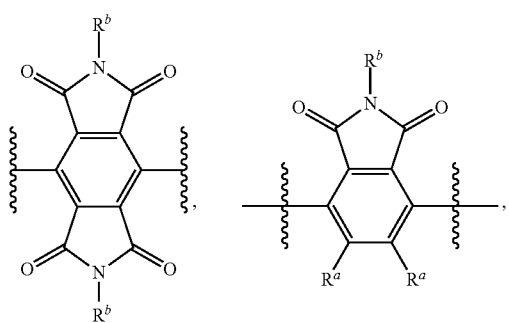
-continued
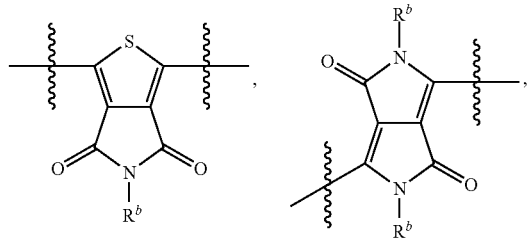
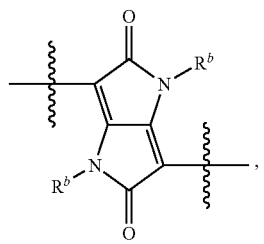
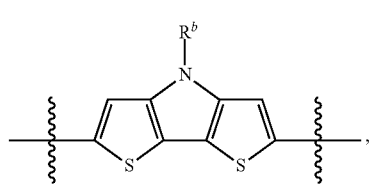
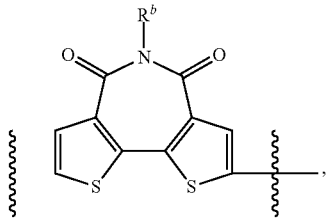
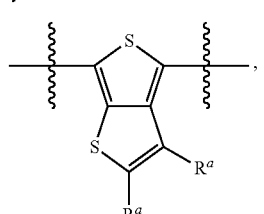
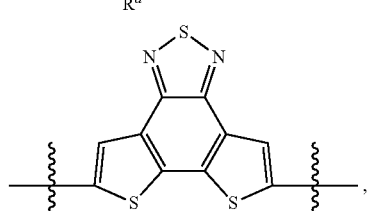
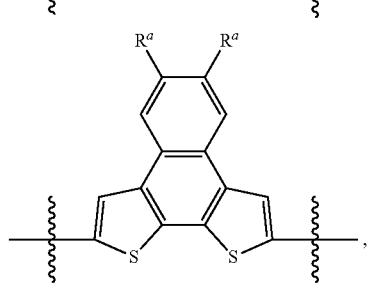

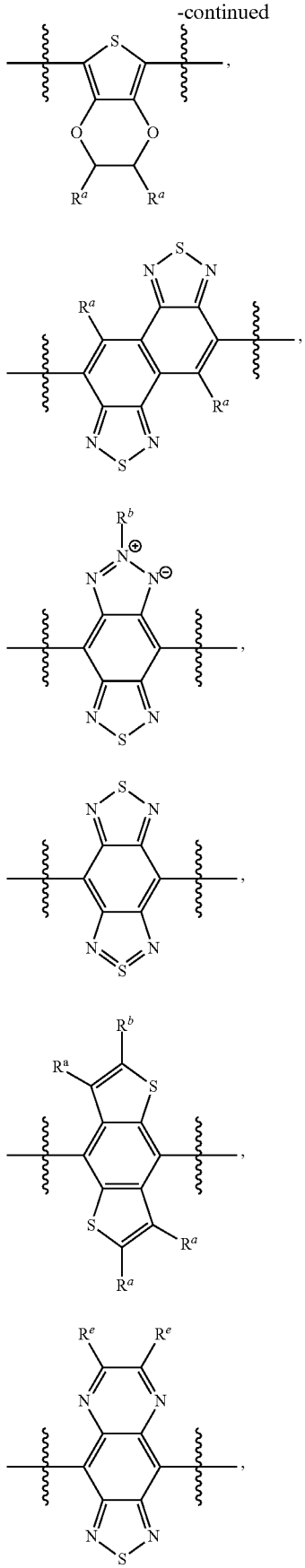

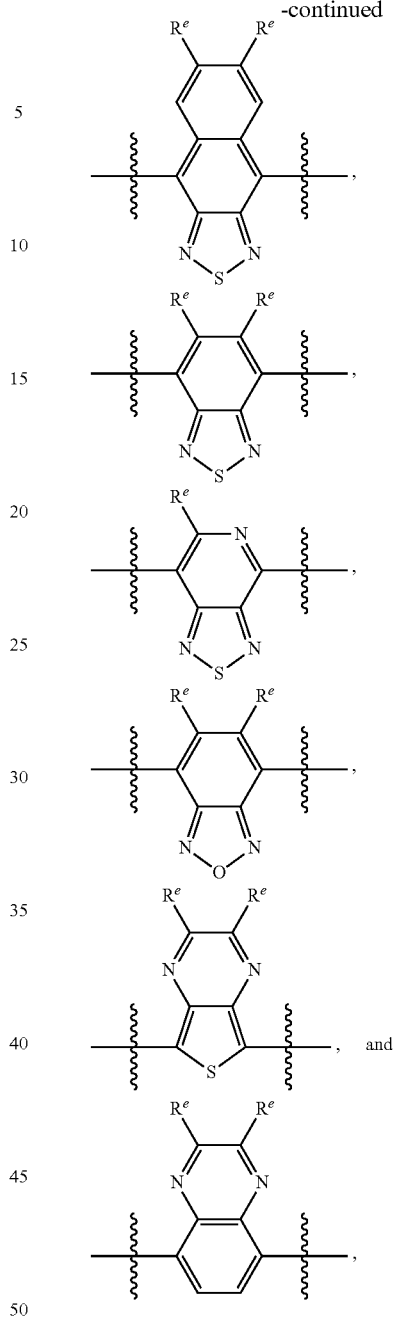

wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;
$R^c$ is H or R;
$R^d$ is selected from the group consisting of H, F, Cl, —CN, R, —OR, —SR, —C(O)R, —OC(O)R, —C(O)OR, and -L-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group.

Embodiments of the present polymers including a pi-2 moiety can be obtained by copolymerization of a first building block including pi-1 and a second building block including pi-2. The second building block including pi-2 can include conjugated spacer groups $Sp^2$ and/or $Sp^3$. For example, certain embodiments of the present polymers can have a formula selected from the group consisting of:

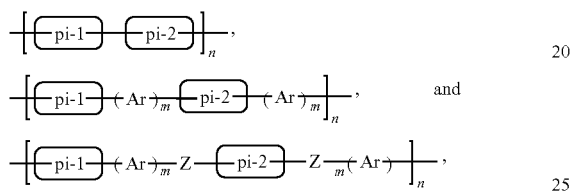

where pi-1, pi-2, Ar, Z, and m are as defined herein. The degree of polymerization (n) can be an integer in the range of 2 to 10,000, for example, in the range of 3 and 5,000, preferably between 5 and 5,000, and more preferably, between 10 and 5,000. For example, particular embodiments of the present polymers can have a formula selected from the group consisting of:

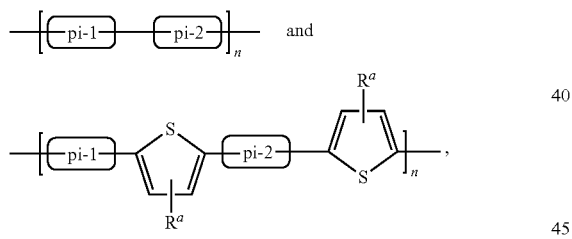

wherein:

$R^a$ is selected from the group consisting of H, F, Cl, —CN, R, —OR, —SR, —C(O)R, —OC(O)R, and —C(O)OR, where R is selected from the group consisting of a $C_{1-40}$ alkyl group, a $C_{1-40}$ haloalkyl group, a $C_{2-40}$ alkenyl group, and a $C_{2-40}$ alkynyl group;

pi-1 is selected from the group consisting of:

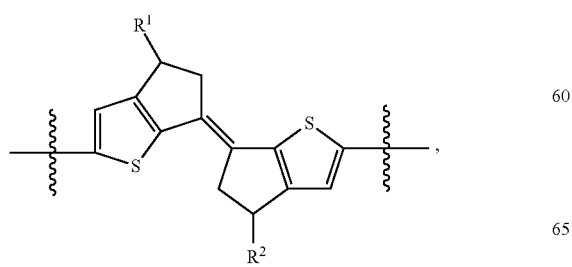

-continued

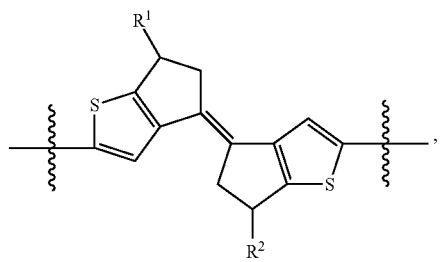

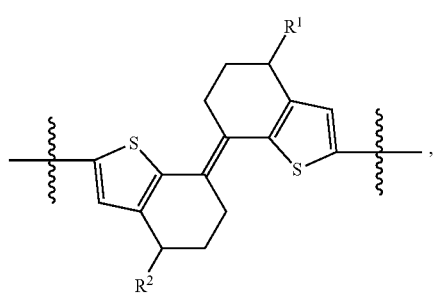

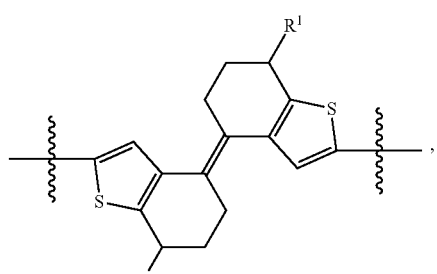

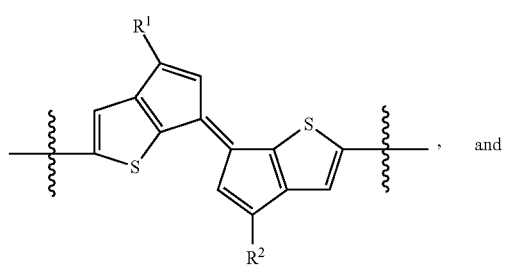, and

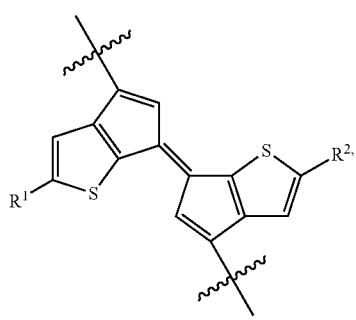

where $R^1$ and $R^2$ can be H or a $C_{1-40}$ alkyl group;

pi-2 is selected from the group consisting of:
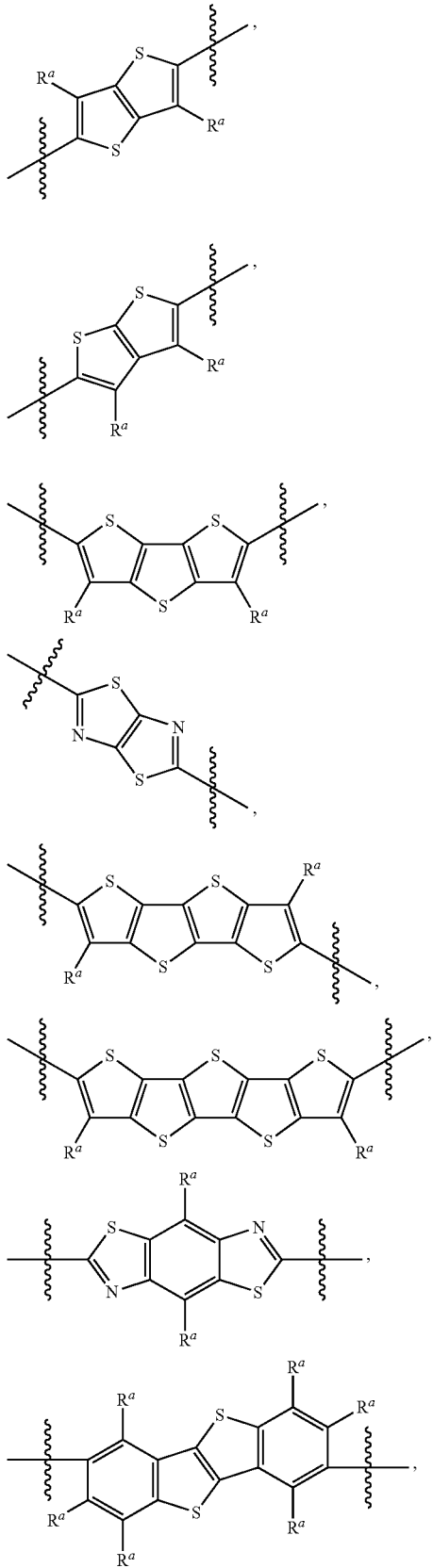
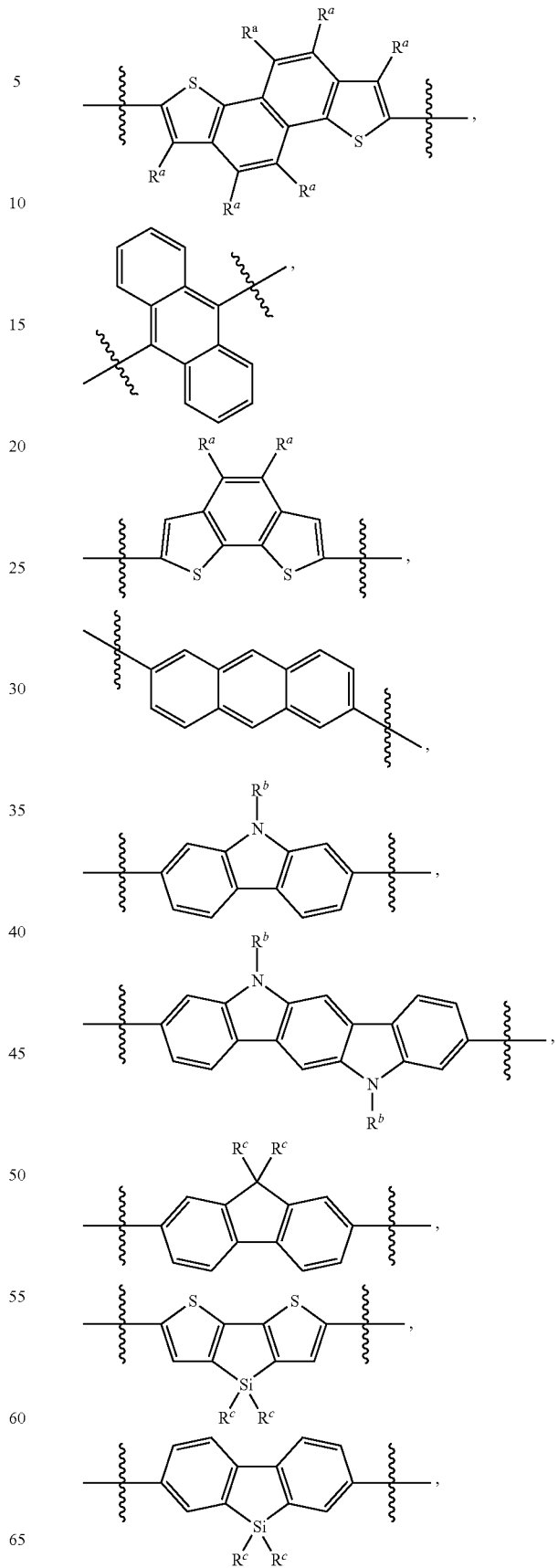

-continued
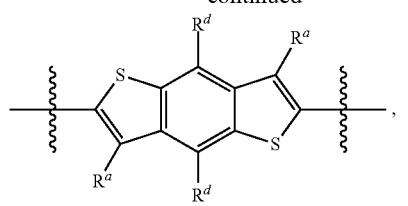
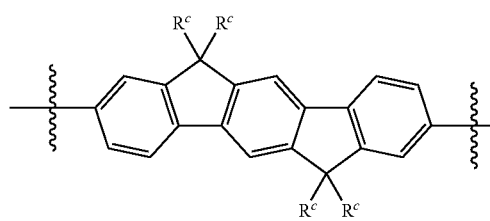
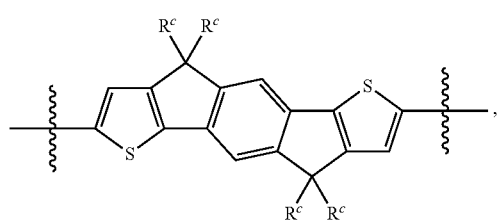
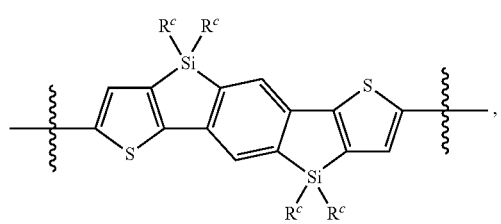
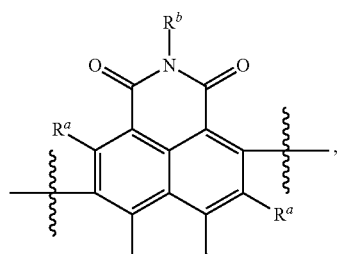
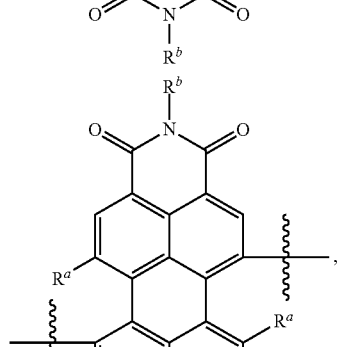
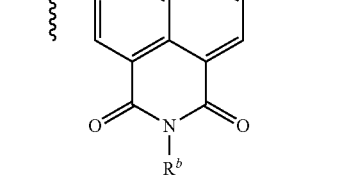
-continued
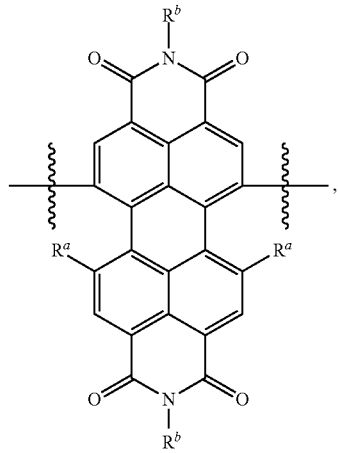
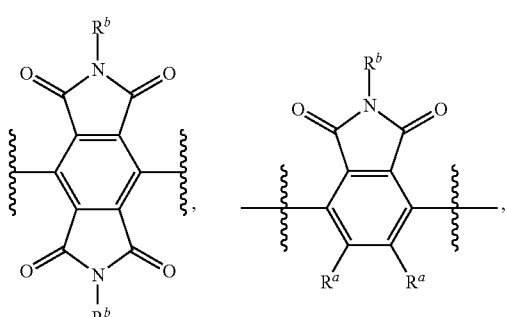
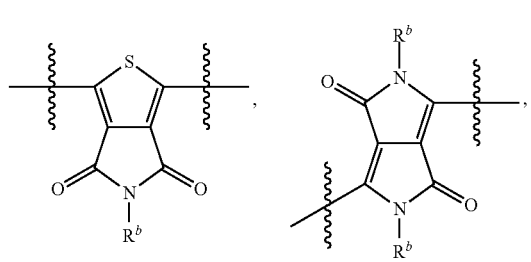
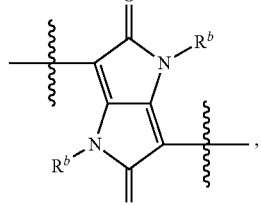
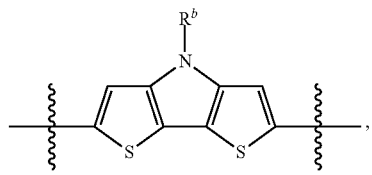
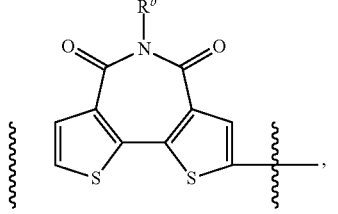

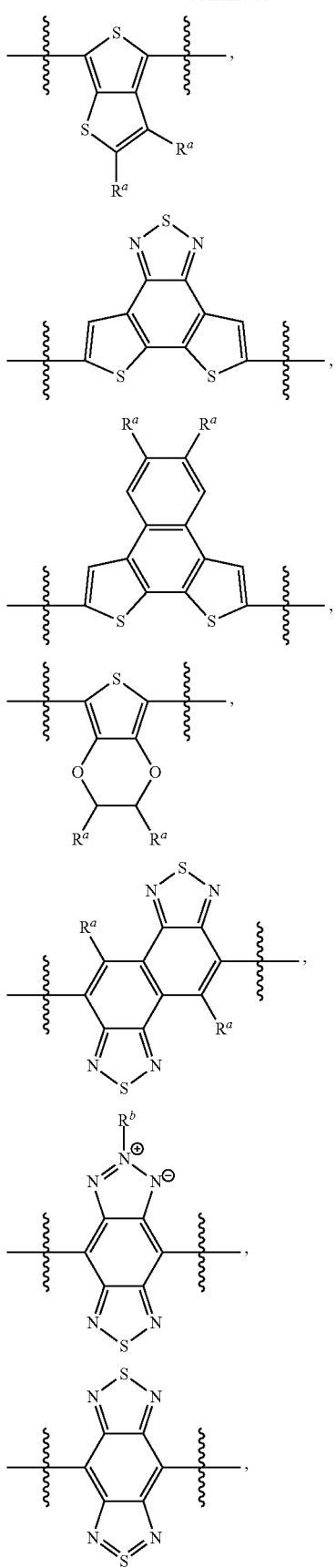
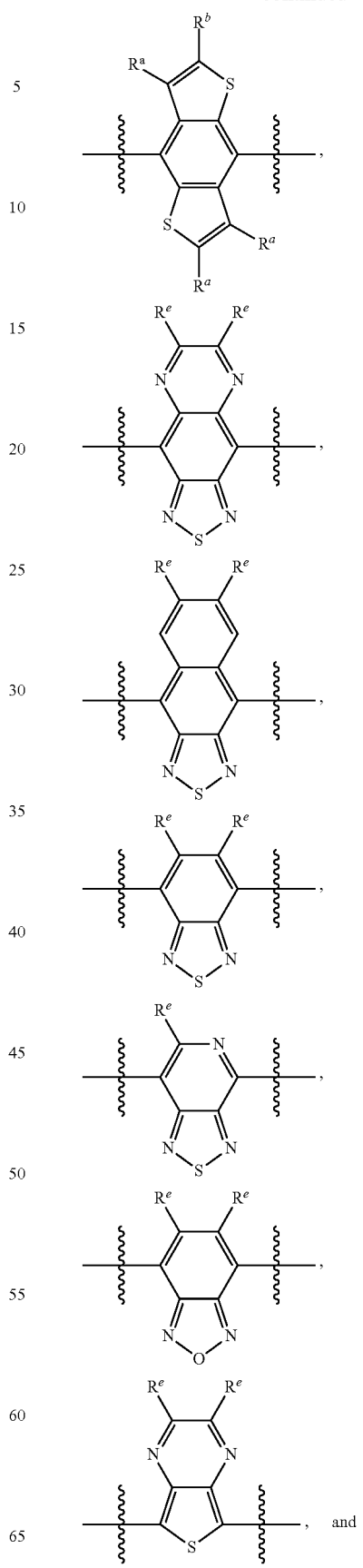

-continued

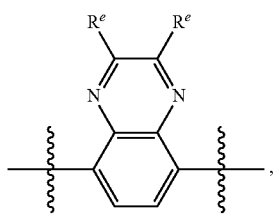

wherein:

$R^a$ is selected from the group consisting of H, F, Cl, —CN, R, —OR, —SR, —C(O)R, —OC(O)R, and —C(O)OR;

$R^b$ is selected from the group consisting of H, R, and -L-$R^f$;

$R^c$ is H or R;

$R^d$ is selected from the group consisting of H, F, Cl, —CN, R, —OR, —SR, —C(O)R, —OC(O)R, —C(O)OR, and -L-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group; and n is an integer in the range of 3 and 5,000.

To illustrate, certain embodiments of the present polymers can be an n-type semiconducting polymer having a formula selected from the group consisting of:

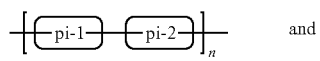 and

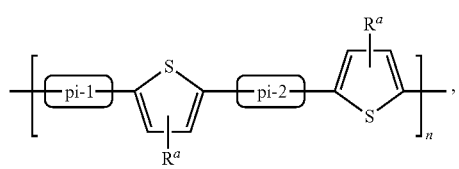

wherein:

$R^a$ is selected from the group consisting of H, F, Cl, —CN, R, —OR, —SR, —C(O)R, —OC(O)R, and —C(O)OR, where R is selected from the group consisting of a $C_{1-40}$ alkyl group, a $C_{1-40}$ haloalkyl group, a $C_{2-40}$ alkenyl group, and a $C_{2-40}$ alkynyl group;

pi-1 is an annulated TVT unit as described herein; and pi-2 is an optionally substituted fused ring tetracarboxylic diimide and can be selected from the group consisting of:

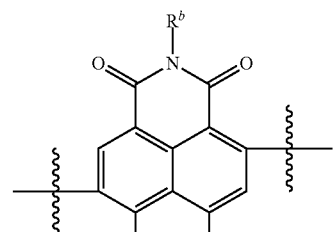

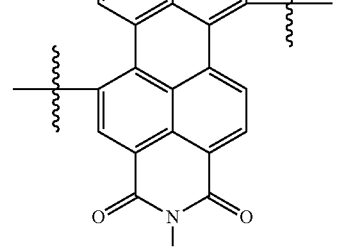

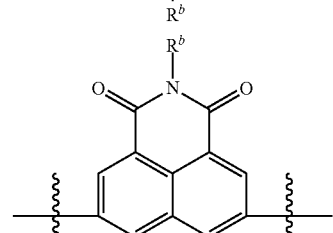

and

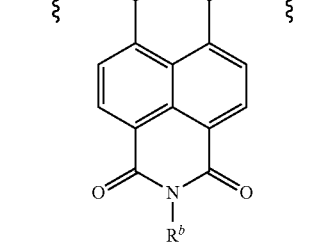

wherein $R^b$ is a linear or branched $C_{1-40}$ alkyl, $C_{1-40}$ haloalkyl, $C_{2-40}$ alkenyl, or $C_{2-40}$ alkynyl group.

In certain embodiments, the present polymers can be a p-type semiconducting polymer having a formula selected from the group consisting of:

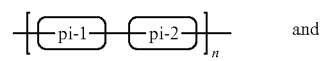 and

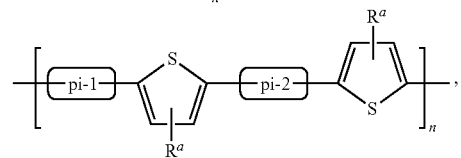

wherein:

R$^a$ is selected from the group consisting of H, F, Cl, —CN, R, —OR, —SR, —C(O)R, —OC(O)R, and —C(O)OR, where R is selected from the group consisting of a C$_{1-40}$ alkyl group, a C$_{1-40}$ haloalkyl group, a C$_{2-40}$ alkenyl group, and a C$_{2-40}$ alkynyl group;

pi-1 is an annulated TVT unit as described herein; and pi-2 is an optionally substituted electron-donating polycyclic moiety and can be selected from the group consisting of:

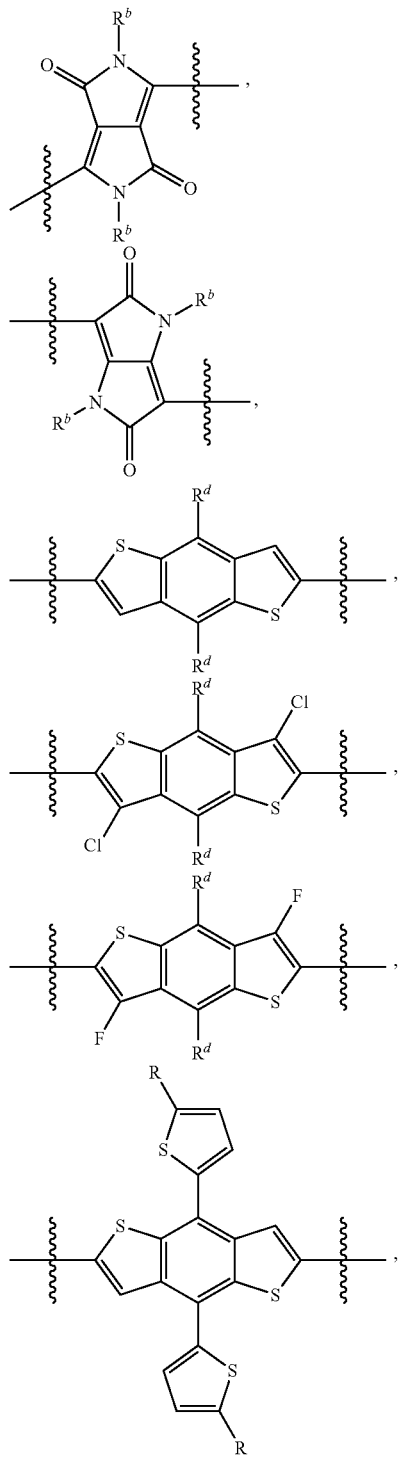

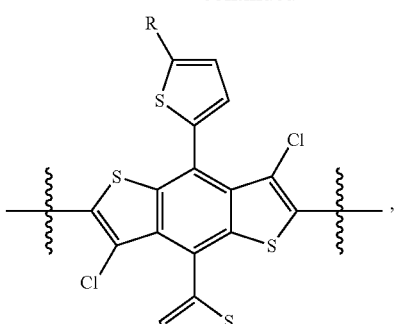

, and

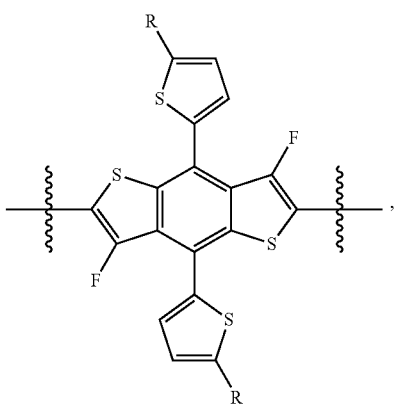

, wherein R$^b$ is a linear or branched C$_{1-40}$ alkyl, C$_{1-40}$ haloalkyl, C$_{2-40}$ alkenyl, or C$_{2-40}$ alkynyl group; R$^d$ is selected from R, OR, and SR; and R is a linear or branched C$_{1-40}$ alkyl, C$_{1-40}$ haloalkyl, C$_{2-40}$ alkenyl, or C$_{2-40}$ alkynyl group.

Without limitation, exemplary embodiments of the present polymers having a formula selected from the group consisting of:

include:

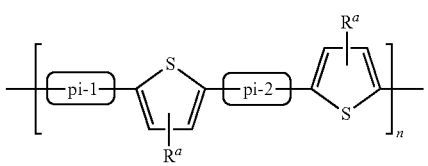

-continued

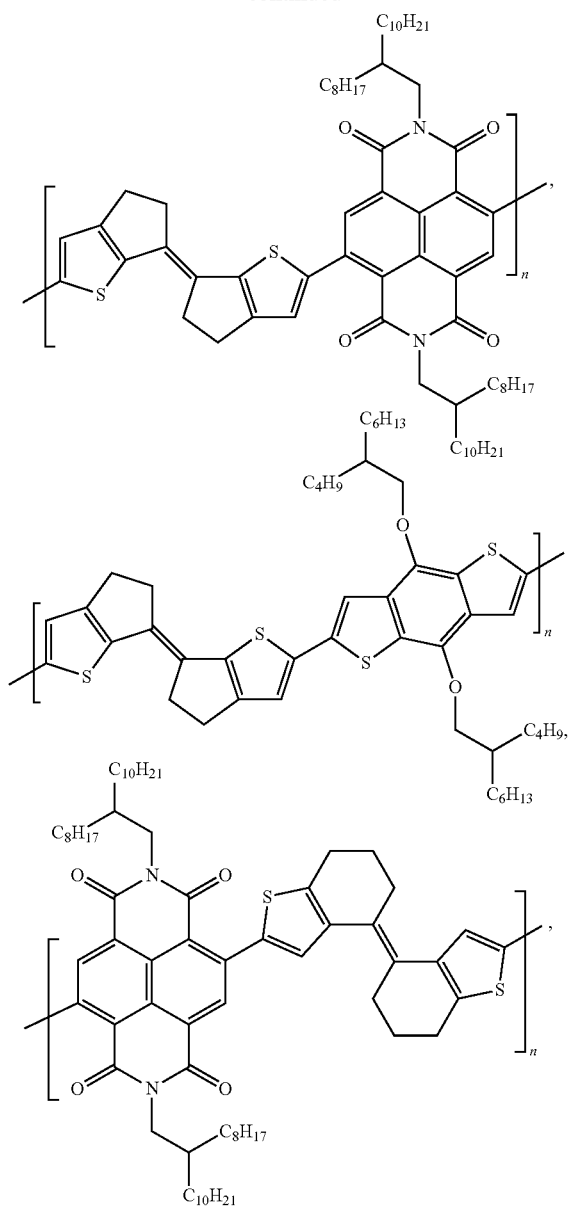

-continued

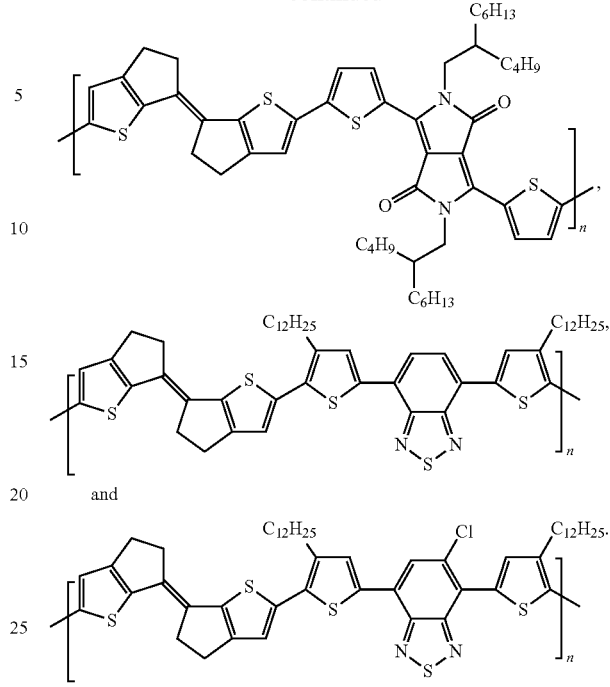

and

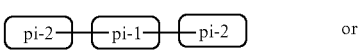

Also within the present teachings are dimers having the formula:

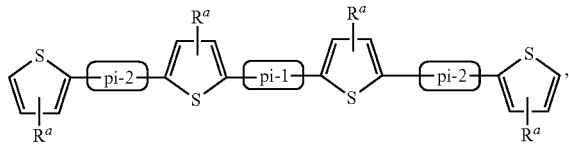

wherein $R^a$ is selected from the group consisting of H, F, Cl, —CN, R, —OR, —SR, —C(O)R, —OC(O)R, and —C(O)OR, where R is selected from the group consisting of a $C_{1-40}$ alkyl group, a $C_{1-40}$ haloalkyl group, a $C_{2-40}$ alkenyl group, and a $C_{2-40}$ alkynyl group; pi-1 is an optionally substituted annulated TVT unit as described herein; and pi-2 is an optionally substituted conjugated polycyclic moiety (examples of which include those provided hereinabove). Specific examples include:

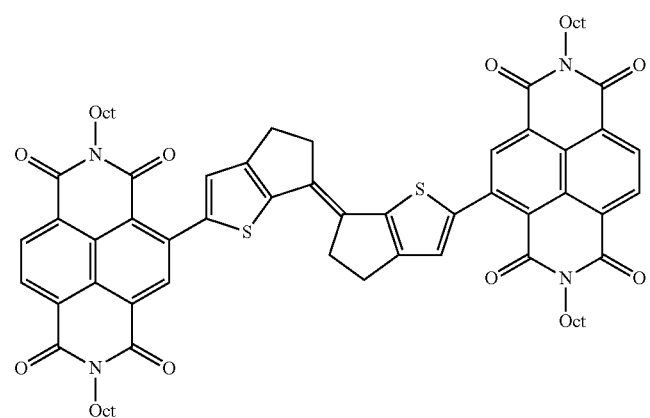

NDI-C5TVT-NDI

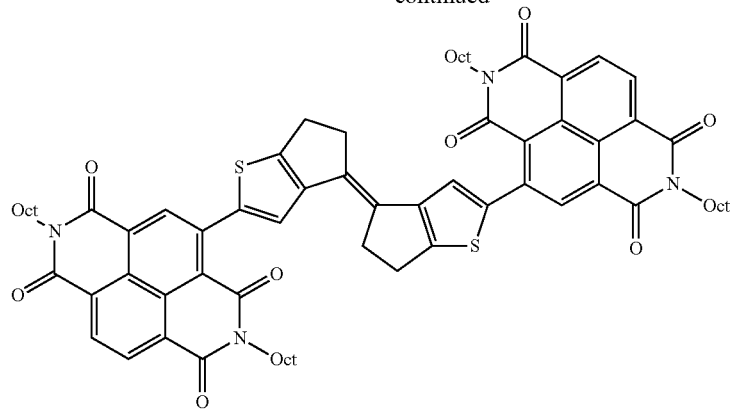

NDI-C5RTVT-NDI

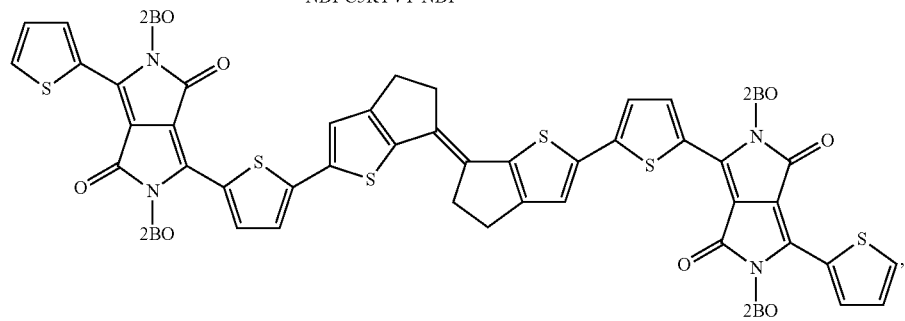

DPP-C5TVT-DPP (Oct: octyl)

where 2BO is a 2-butyloctyl group.

In certain embodiments, in addition to the first repeating unit:

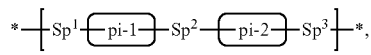

the present polymers also can include a second repeating unit which is different from the first repeating unit and has the formula:

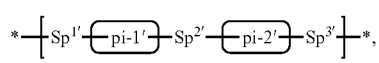

wherein:

pi-1' is an annulated thienyl-vinylene-thienyl (TVT) unit as described herein, for example, as represented by the formula:

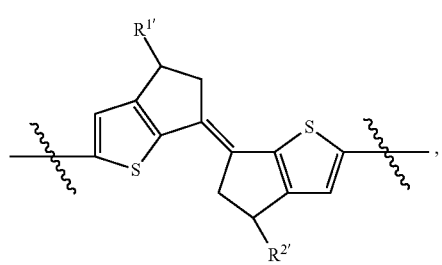

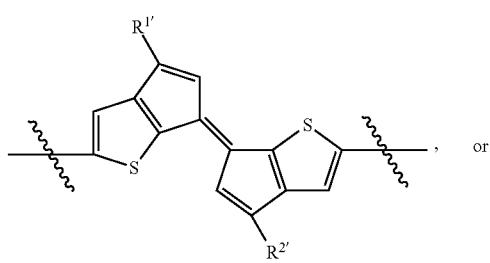, or

-continued

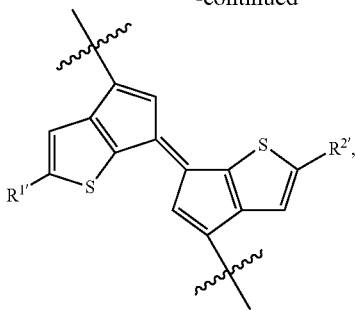

wherein $R^{1\prime}$ and $R^{2\prime}$ independently are selected from the group consisting of H, halogen, CN, a $C_{1-40}$ alkyl group, a $C_{2-40}$ alkenyl group, and a $C_{1-40}$ haloalkyl group;
pi-2' is a covalent bond or an optionally substituted conjugated polycyclic moiety; and
$Sp^{1\prime}$, $Sp^{2\prime}$, and $Sp^{3\prime}$ independently are a covalent bond or a conjugated spacer group comprising at least one of a conjugated linear linker and an optionally substituted conjugated monocyclic moiety; provided at least one of pi-2', $Sp^{1\prime}$, $Sp^{2\prime}$, and $Sp^{3\prime}$ is not a covalent bond.

For example, the second repeating unit can have a formula selected from the group consisting of:

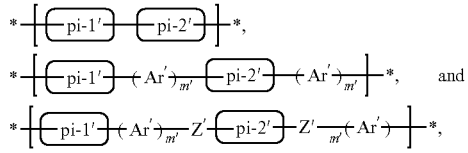

wherein:
pi-2' is an optionally substituted conjugated polycyclic moiety;
each Ar' independently is an optionally substituted conjugated monocyclic moiety;
Z' is a conjugated linear linker; and
m' is 1, 2, 3 or 4.

The first repeating unit and the second repeating unit can be arranged in an alternating manner or a random manner. In preferred embodiments, pi-1 and pi-1' can be the same, and the present polymer can be a random copolymer provided by copolymerization of pi-1 with two different building blocks each including an optionally substituted conjugated polycyclic moiety (i.e., pi-2 and pi-2'). To illustrate, random copolymers according to the present teachings can have a formula selected from the group consisting of:

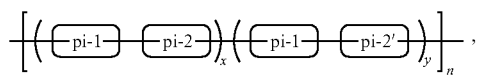

(where pi-2' is different from pi-2)

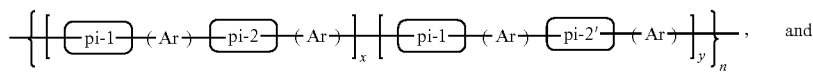

(where pi-2' is different from pi-2)

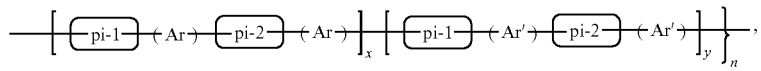

(where Ar' is different from Ar)

(where Ar' is different from Ar), wherein x and y are real numbers representing mole fractions, wherein $0.05 \leq x \leq 0.95$, $0.05 \leq y \leq 0.95$, and the sum of x and y is about 1.

For example, random polymers according to the present teachings can have the formula:

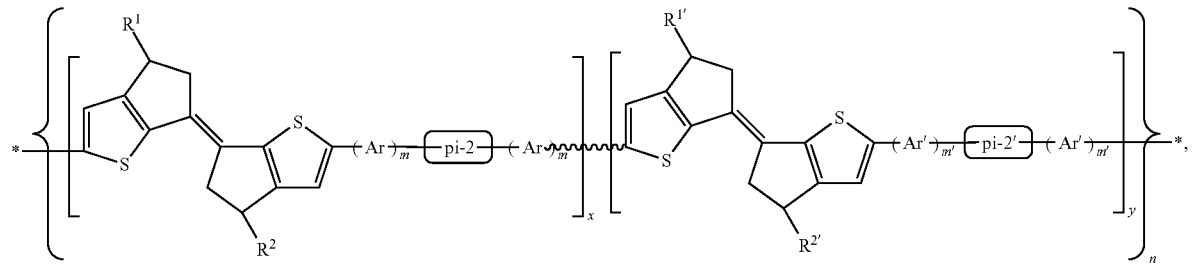

-continued

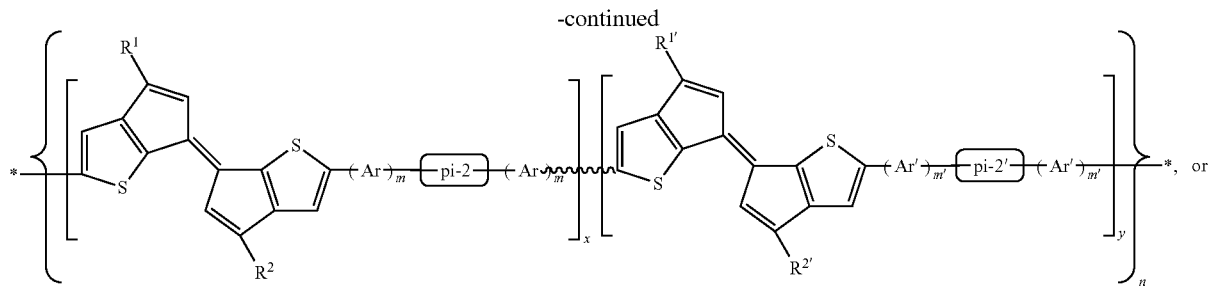

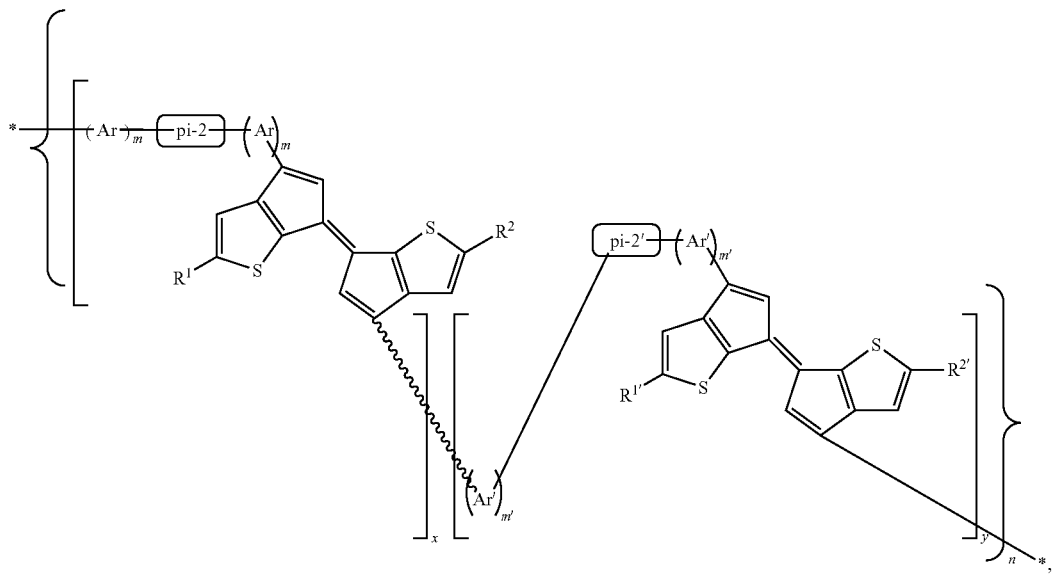

wherein n is an integer in the range of 3 to 5,000; x and y are real numbers representing mole fractions, wherein $0.05 \leq x \leq 0.95$, $0.05 \leq y \leq 0.95$, and the sum of x and y is about 1; and provided Ar is different from Ar', or $R^1$ and $R^2$ are different from $R^{1'}$ and $R^{2'}$, or pi-2 is different from pi-2', or m is different from m'.

In preferred embodiments, Ar and Ar' are different. To further illustrate, specific embodiments of the present random copolymers can have the formula:

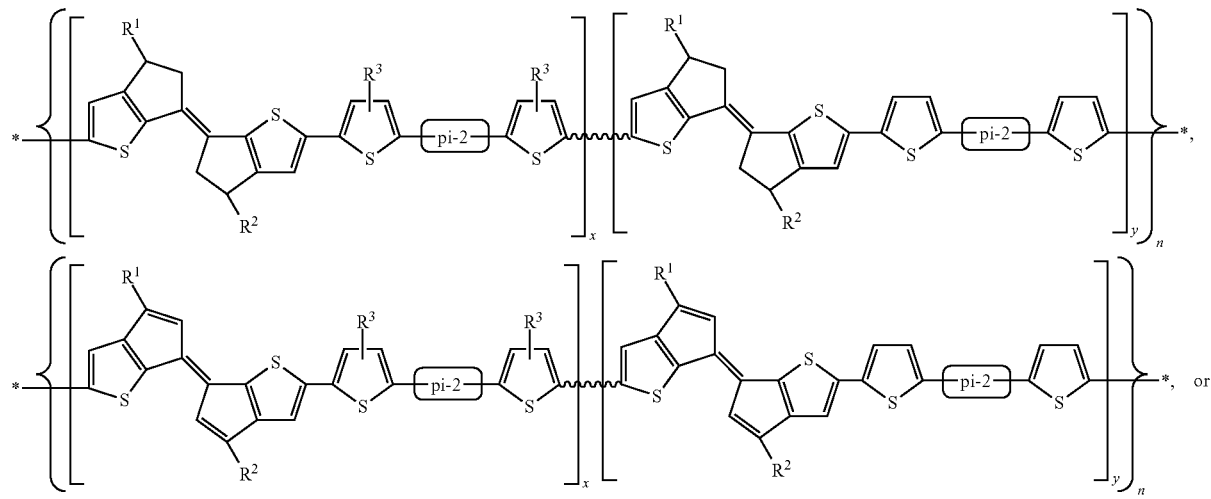

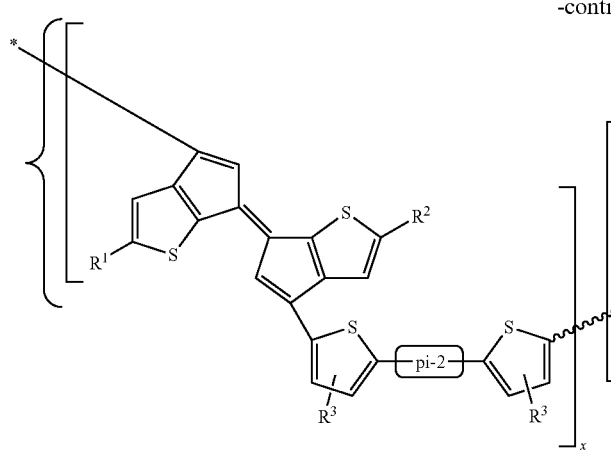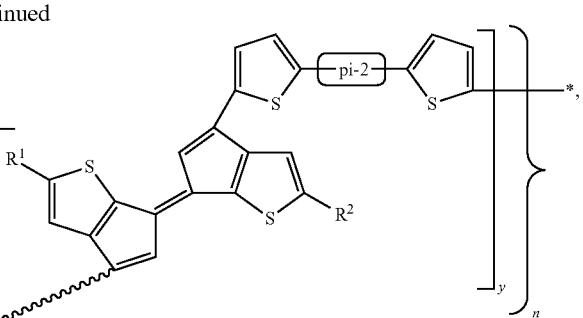

wherein each R³ independently is selected from the group consisting of R, OR, and SR, where R is selected from the group consisting of a $C_{1-40}$ alkyl group, a $C_{1-40}$ haloalkyl group, a $C_{2-40}$ alkenyl group, and a $C_{2-40}$ alkynyl group; and $R^1$, $R^2$, pi-2, x, y, and n are as defined herein.

Polymers of the present teachings and monomers leading to the present polymers can be prepared according to procedures analogous to those described in the Examples. In particular, McMurry reaction can be used to prepare the pi-1 building block by coupling two ketones having the formula:

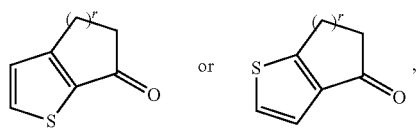

where r is 1 or 2, in the presence of a metal catalyst such as titanium chloride and a reducing agent such as Zn, K, or Mg. Subsequently, Stille coupling reactions can be used to couple stannylated pi-1 units with one or more brominated $Sp^1$, $Sp^2$, $Sp^3$, and/or pi-2 units (or vice versa) to prepare dimers and polymers according to the present teachings with high molecular weights and in high yields and purity, as confirmed by ¹H NMR spectra, elemental analysis, and/or GPC measurements. Other coupling reactions (such as Suzuki coupling and Negishi coupling) are known in the art and can be used as well.

Alternatively, the present polymeric compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., ¹H or ¹³C), infrared spectroscopy (IR), optical absorption/emission spectroscopy (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Polymers disclosed herein can be soluble in various common organic solvents. As used herein, a polymer can be considered soluble in a solvent when at least 0.1 mg of the polymer can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone.

The polymers described herein can be dissolved, dispersed or suspended in a single solvent or mixture of solvents to provide a composition suitable for solution processing techniques. In preferred embodiments, the solvent can be selected from the group consisting of chlorobenzene, dichlorobenzene (o-dichlorobenzene, m-dichlorobenzene, p-orobenzene, or mixtures thereof), trichlorobenzene, benzene, toluene, chloroform, dichloromethane, dichloroethane, xylenes, α,α,α-trichlorotoluene, methyl naphthalene (e.g., 1-methylnaphthalene, 2-methylnaphthalene, or mixtures thereof), chloronaphthalene (e.g., 1-chloronaphthalene, 2-chloronaphthalene, or mixtures thereof), and mixtures thereof. Various solution processing techniques have been used with organic electronics. Common solution processing techniques include, for example, spin coating, slot coating, doctor blading, drop-casting, zone casting, dip coating, blade coating, or spraying. Another example of solution processing technique is printing. As used herein, "printing" includes a noncontact process such as inkjet printing, microdispensing and the like, and a contact process such as screen-printing, gravure printing, offset printing, flexographic printing, lithographic printing, pad printing, microcontact printing and the like.

Polymers of the present teachings can exhibit semiconductor behavior (including photoactive behavior) such as optimized light absorption/charge separation in a photovoltaic device; charge transport/recombination/light emission in a light-emitting device; and/or high carrier mobility and/or good current modulation characteristics in a field-effect device. In addition, the present polymers can possess certain processing advantages such as solution-processability and/or good stability (e.g., air stability) in ambient conditions. The polymers of the present teachings can be used alone or in combination with other compounds to prepare either p-type (donor or hole-transporting), n-type (acceptor or electron-transporting), or ambipolar semiconductor materials, which in turn can be used to fabricate various organic or hybrid optoelectronic articles, structures and devices, including organic photovoltaic devices and organic light-emitting transistors. In some embodiments, semiconductor materials incorporating one or more compounds of the present teachings can exhibit p-type semiconductor activity, ambipolar activity, light absorption, and/or light emission.

The present teachings, therefore, further provide methods of preparing a semiconductor material and composites (e.g., devices) including the semiconductor material. The methods can include preparing a composition (e.g., a solution or dispersion) that includes one or more polymeric compounds disclosed herein dissolved or dispersed in a liquid medium such as a solvent or a mixture of solvents, and depositing the composition on a substrate to provide a semiconductor material. The deposited semiconductor material can be processed further (e.g., subject to an annealing step) prior to formation of additional components thereon to complete a particular device structure.

Various articles of manufacture including optical devices, optoelectronic devices, and electronic devices such as thin film semiconductors, photovoltaic/solar cells, photodetectors (or photodiodes), organic light emitting devices such as organic light emitting transistors (OLETs), that make use of the polymers disclosed herein are within the scope of the present teachings as are methods of making the same. The present polymers can offer processing and operation advantages in the fabrication and/or the use of these devices.

For example, articles of manufacture such as the various devices described herein can be an optical or optoelectronic device including a first electrode, a second electrode, and a photoactive component disposed between the first electrode and the second electrode, where the photoactive component includes a polymer of the present teachings.

In various embodiments, the optical or optoelectronic device can be configured as a solar cell, in particular, a bulk heterojunction solar cell. Polymers of the present teachings can exhibit broad optical absorption and/or a tuned redox properties and bulk carrier mobilities, making them desirable for such applications. In some embodiments, the bulk heterojunction solar cells according to the present teachings can incorporate a blend material (e.g., a blended film) including a polymer of the present teachings as the donor material and an acceptor material as the photoactive layer. Typical acceptor materials include fullerene-based compounds. Fullerenes useful in the present teachings can have a broad range of sizes (number of carbon atoms per molecule). The term fullerene as used herein includes various cage-like molecules of pure carbon, including Buckminsterfullerene ($C_{60}$) "bucky ball" and the related "spherical" fullerenes as well as carbon nanotubes. Fullerenes can be selected from those known in the art ranging from, for example, $C_{20}$-$C_{1000}$. In certain embodiments, the fullerene can be selected from the range of $C_{60}$ to $C_{96}$. In particular embodiments, the fullerene can be a $C_{60}$ fullerene derivative or a $C_{70}$ fullerene derivative, such as [6,6]-phenyl-$C_{61}$-butyric acid methyl ester ($PC_{61}BM$ or simply PCBM) or [6,6]-phenyl-$C_{71}$-butyric acid methyl ester ($PC_{71}BM$). In some embodiments, chemically modified fullerenes can be used, provided that the modified fullerene retains acceptor-type and electron mobility characteristics. Some common fullerene derivatives include bisadduct of $PC_{61}BM$ (Bis-PCBM), indene-$C_{60}$ monoadduct (ICMA), and indene-$C_{60}$ bisadduct (ICBA). Further, other acceptor materials can be used in place of fullerenes, provided that they have the required acceptor-type and electron mobility characteristics. For example, the acceptor material can be various organic small molecules, polymers, carbon nanotubes, or inorganic particles (quantum dots, quantum rods, quantum tripods, $TiO_2$, ZnO etc.).

In some embodiments, the acceptor material can be an electron-transporting (n-type) polymer. In some embodiments, the electron-transporting polymer can comprise a bis(imide)arene unit. Exemplary polymers are described in U.S. Patent Publication Nos. 2010/0326527, 2010/0326527, and 2010/0283047.

In some embodiments, the bulk heterojunction solar cells according to the present teachings can incorporate a blend material (e.g., a blended film) including a polymer of the present teachings as the acceptor material and a donor material as the photoactive layer. For example, embodiments of the present polymers that can function as an acceptor material (i.e., an n-type semiconducting polymer) include those having a bis(imide)arene unit, for example, a naphthalene diimide, as the pi-2 moiety. Many donor polymers have been reported, the most well known being poly(3-hexylthiophene) or P3HT. Many donor polymers have an alternating push-pull structure:

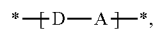

where the donor subunit (D) often includes a bridged dithiophene moiety (such as a benzodithiophene moiety, a naphthodithiophene moiety, a thienodithiophene moiety, and a pyridodithiophene moiety); the acceptor subunit (A) can include an electron-poor conjugated moiety; and either the donor subunit (D) or the acceptor subunit (A) can comprise one or more thienyl or thienothienyl groups. Suitable donor polymers are described in, for example, U.S. Patent Publication No. US 2013/0247992 and Facchetti, "Pi-Conjugated Polymers for Organic Electronics and Photovoltaic Cell Applications," *Chem. Mater.*, 23:733-758 (2011). In alternative embodiments where the annulated TVT unit is copolymerized with an electron-donating polycyclic moiety, the present polymers can function as a donor material (i.e., a p-type semiconducting polymer). Such p-type semiconducting polymer can be used together with a fullerene-based acceptor material or an n-type semiconducting polymer (including an n-type semiconducting polymer according to the present teachings) in a solar cell.

A photoactive component according to the present teachings can be prepared as a blended film deposited from a solution or dispersion containing a mixture of one or more of the present compounds and either an acceptor compound such as fullerene (e.g., PCBM) or a polymeric acceptor described herein, or a donor polymer. The ratio of the donor polymer to the acceptor compound can range from about 10:1 to about 1:10 by weight; for example, from about 5:1 to about 1:5 by weight, from about 3:1 to about 1:3 by weight, or from about 2:1 to about 1:2 by weight. The photoactive layer also can contain a polymeric binder, which can be present from about 5 to about 95% by weight. The polymeric binder, for example, can be a semicrystalline polymer selected from polystyrene (PS), high density polyethylene (HDPE), polypropylene (PP) and polymethylmethacrylate (PMMA). In some embodiments, the polymeric blend can be used together with additional components that are optically active, for example, components that can assist in light harvesting by capturing and transferring excitons to one or both of the electron-donor polymers/electron-acceptor polymers in the blend, and/or optically non-active components to modify and/or improve processing and/or device performance. Such optically non-active components can include alkanethiols (e.g., alkanedithiols) and other α,ω-functionalized alkanes (e.g., diiodoalkanes) as known in the art. See e.g., U.S. Pat. No. 8,227,691.

The blend composition can be deposited on a substrate (e.g., an electrode-substrate) preferably via a solution-phase process, followed by removal of the solvent or mixture of solvents to provide the photoactive layer. By having the blend composition provided as an intimate mixture of the present polymer and an acceptor compound, bulk heterojunctions are created upon removal of the solvent (optionally under reduced pressure and/or elevated temperature), during which nanoscale phase separation of the present donor polymers and the acceptor compound takes place. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, slot-die coating, drop-casting, zone casting, dip coating, blade coating, or spraying. When the film is formed by spin coating, the spin speed can range from about 300 rpm to about 6000 rpm, or from about 500 rpm to about 2000 rpm. Subsequent processing steps can include thermal annealing or irradiation of the deposited film. For example, the blended film can be annealed from about 50° C. to about 300° C., preferably from about 70° C. to about 200° C., more preferably from about 90° C. to about 180° C. for about 1 min to about 20 minutes. The annealing step can be carried out under an inert atmosphere (e.g., under nitrogen). Irradiation of the deposited film can be carried out using infrared light or ultraviolet light. As used herein, "annealing" refers to a post-deposition heat treatment to the semicrystalline polymer film in ambient or under reduced/increased pressure for a time duration of more than 60 seconds, and "annealing temperature" refers to the maximum temperature that the polymer film is exposed to for at least 30 seconds during this process of annealing. The photoactive layer typically can have a thickness ranging from about 30 nm to about 500 nm. In preferred embodiments, the photoactive layer can be a thin film having a thickness of about 80-300 nm.

FIG. 1 illustrates a representative structure of a bulk-heterojunction organic solar cell which can incorporate one or more compounds of the present teachings as either the donor material or the acceptor material. As shown, a representative solar cell 20 generally includes an anode 22, a cathode 26, and a photoactive layer 24 between the anode and the cathode that can incorporate one or more polymers of the present teachings as either the electron donor (p-channel) material or the electron acceptor (n-channel) material. In some embodiments, an optional smoothing layer can be present between the anode and the photoactive layer.

The substrate 28 can be a solid, rigid or flexible layer designed to provide robustness to the device. In preferred embodiments, the substrate can be transparent or semi-transparent in the spectral region of interest. As used herein, a material is considered "transparent" when it has transmittance over 50%, and a material is considered "semi-transparent" when it has transmittance between about 50% and about 5%. The substrate can comprise any suitable material known in the art such as glass or a flexible plastic (polymer) film.

The first and second electrodes should have different work functions, with the electrode having the higher work function at or above about 4.5 eV (the "high work function electrode") serving as the hole-injecting electrode or anode, and the electrode having the lower work function at or below about 4.3 eV (the "low work function electrode") serving as the electron-injecting electrode. In a traditional OPV device structure, the high work function electrode or anode typically is composed of a transparent conducting metal oxide or metal sulfide such as indium tin oxide (ITO), gallium indium tin oxide (GITO), and zinc indium tin oxide (ZITO), or a thin, transparent layer of gold or silver. The low work function electrode or cathode typically is composed of a low work function metal such as aluminum, indium, calcium, barium, and magnesium. The electrodes can be deposited by thermal vapor deposition, electron beam evaporation, RF or magnetron sputtering, chemical vapor deposition or the like.

In various embodiments, the solar cell can include one or more optional interface layers ("interlayers") between the anode and the photoactive layer and/or between the cathode and the photoactive layer. For example, in some embodiments, an optional smoothing layer (e.g., a film of 3,4-polyethylenedioxythiophene (PEDOT), or 3,4-polyethylenedioxythiophene:polystyrene-sulfonate (PEDOT:PSS)) can be present between the anode and the photoactive layer. The optional interlayer(s) can perform other functions such as reducing the energy barrier between the photoactive layer and the electrode, forming selective contacts for a single type of carrier (e.g., a hole-blocking layer), modifying the work function of the adjacent electrode, and/or protecting the underlying photoactive layer. In some embodiments, a transition metal oxide layer such as $V_2O_5$, $MoO_3$, $WO_3$ and NiO can be deposited on top of the ITO anode, instead of using PEDOT or PEDOT:PSS as the p-type buffer. To improve device stability via modification of the cathode, an n-type buffer composed of LiF, CsF or similar fluorides can be provided between the cathode and the photoactive layer. Other n-type buffer materials include $TiO_x$, $ZnO_x$ and Cs-doped $TiO_x$. Depending on the composition, the interlayers can be solution-processed (e.g., sol-gel deposition, self-assembled monolayers) or deposited by vacuum processes such as thermal evaporation or sputtering.

In certain embodiments, a solar cell according to the present teachings can include a transparent glass substrate onto which an electrode layer (anode) made of indium tin oxide (ITO) is applied. This electrode layer can have a relatively rough surface, and a smoothing layer made of a polymer, typically PEDOT:PSS made electrically conductive through doping, can be applied on top of the electrode layer to enhance its surface morphology. Other similar interlayers can be optionally present between the anode and the photoactive layer for improving mechanical, chemical, and/or electronic properties of the device. The photoactive layer is composed of an all-polymer blend as described above, and can have a layer thickness of, e.g., about 80 nm to a few μm. Before a counter electrode (cathode) is applied, an electrically insulating transition layer can be applied onto the photoactive layer. This transition layer can be made of an alkali halide, e.g., LiF, and can be vapor-deposited in vacuum. Again, similar to the anode, other similar interlayers can be optionally present between the photoactive layer and the cathode for improving mechanical, chemical, and/or electronic properties of the device.

In certain embodiments, a solar cell according to the present teachings can have an inverted device structure, where a modified ITO film is used as the cathode. For example, the ITO can be modified by n-type metal oxides or metal carbonates such as $TiO_x$, $ZnO_x$, Cs-doped $TiO_x$, and caesium carbonate. In particular embodiments, the inverted OPV can include a solution-processed $ZnO_x$ n-type interface layer as described in Lloyd et al., "Influence of the hole-transport layer on the initial behavior and lifetime of inverted organic photovoltaics," *Solar Energy Materials and Solar Cells*, 95(5): 1382-1388 (2011). Compared with the traditional device structure, inverted-type devices can demonstrate better long-term ambient stability by avoiding the need for the corrosive and hygroscopic hole-transporting PEDOT:PSS and low work function metal cathode. The anode of an inverted OPV cell can be composed of Ag, Au, and the like, with an optional p-type interface layer composed of transition metal oxides such as $V_2O_5$, $MoO_3$, $WO_3$ and NiO.

Another aspect of the present teachings relates to methods of fabricating an organic light-emitting transistor or an organic light-emitting diode (OLED) that incorporates one or more semiconductor materials of the present teachings. For example, in an OLED, one or more compounds of the present teachings can be used as electron-transporting and/or emissive and/or hole-transporting materials. An OLED generally includes a substrate, a transparent anode (e.g., ITO), a cathode (e.g., metal), and one or more organic layers which can incorporate one or more compounds of the present teachings as hole-transporting (p-channel) and/or emissive and/or electron-transporting (n-channel) materials. In embodiments where the present compounds only have one or two of the properties of hole transport, electron transport, and emission, the present compounds can be blended with one or more further organic compounds having the remaining required property or properties.

In other embodiments, the article of manufacture can be an electronic or optoelectronic device (e.g., an organic light-emitting transistor) including a first electrode, a second electrode, and a semiconducting component in contact with the first electrode and the second electrode, where the semiconducting component includes a compound of the present teachings. These devices can include a composite having a semiconducting component (or semiconductor material) of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., as described in Yoon, M-H. et al., PNAS, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylene-dioxythiophene) poly(styrenesulfonate) (PEDOT:PSS), polyaniline (PANI), polypyrrole (PPy)).

The following examples are provided to illustrate further and to facilitate the understanding of the present teachings and are not in any way intended to limit the invention.

All reagents were commercially available and were used without further purification unless otherwise stated. Anhydrous dichloromethane was distilled from $CaH_2$.

Unless otherwise stated, all reactions were carried out under inert atmosphere using standard Schlenk line techniques. NMR spectra were recorded on Varian Unity Plus 500 (500 MHz, room temperature) or Mercury (400 MHz, high temperature) spectrometers, and chemical shifts are referenced to residual protio-solvent signals.

Example 1: Synthesis of pi-1 Building Blocks

Example 1a: Synthesis of 6,6'-bis(2-trimethylstannyl-4,5-dihydro-6H-cyclopenta[b]thienylidene) (C5TVT-tin)

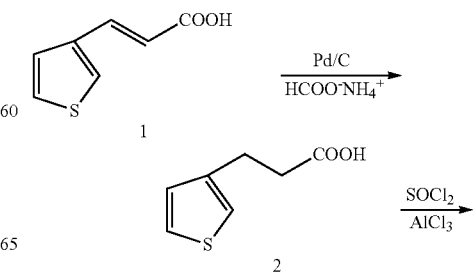

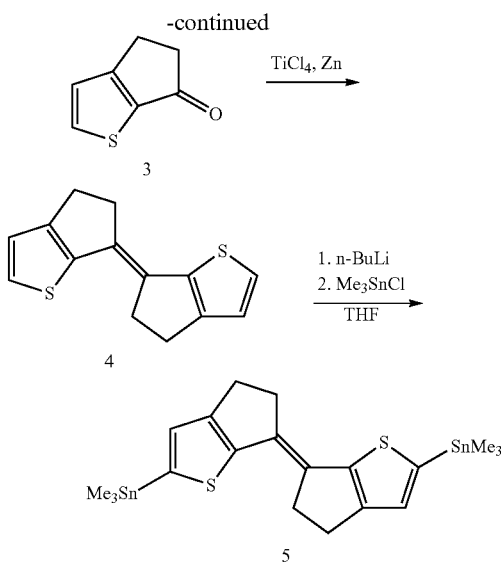

Synthesis of 2:

Pd/C (600 mg, 10 wt %) and ammonium formate (2.50 g, 39 mmol) were added to an isopropyl alcohol solution of trans-3-(3-thienyl)acrylic acid 1 (2.00 g, 13 mmol) under a $N_2$ atmosphere at 25° C. The mixture was stirred overnight at 80° C., and concentrated. The mixture was dissolved in dichloromethane ($CH_2Cl_2$), filtered through Celite®, and evaporated under reduced pressure to afford a white solid 2 upon standing (1.93 g, yield: 95%). The compound was used for the next reaction without further purification. $^1$H NMR (400 MHz, $CDCl_3$): δ (ppm)=2.69 (t, J=8.0 Hz, 2H), 2.99 (t, J=8.0 Hz, 2H), 6.96 (dd, J=5.0, 1.3 Hz, 1H), 7.00-7.01 (m, 1H), 7.26-7.28 (m, 1H).

Synthesis of 3:

A chloroform solution of 2 (2.00 g, 12.8 mmol) in the presence of a catalytic amount of DMF (0.05 mL) was treated dropwise with thionyl chloride (1.86 mL, 25.6 mmol) under a $N_2$ atmosphere at 25° C. The mixture was heated under reflux for 2 hours. The resulting dark orange solution was cooled, and concentrated in vacuo to give a brown oil. A 1,2-dichloroethane (DCE) solution of the carboxylic acid chloride was added dropwise to a suspension of $AlCl_3$ (1.71 g, 12.8 mmol) in DCE at 25° C. The mixture was stirred overnight at 25° C., then heated under reflux for 2 hours, and afterwards poured into an aqueous solution of HCl (5%). The aqueous phase was extracted with $CH_2Cl_2$, dried over $Na_2SO_4$, and evaporated. The residue was purified with a short silica pad ($CH_2Cl_2$) to afford cyclopenta[b]thiophen-6-one 3 as a white solid upon standing (1.45 g, yield: 82%). $^1$H NMR (400 MHz, $CDCl_3$): δ (ppm)=2.98-3.00 (m, 2H), 3.02-3.04 (m, 2H), 7.05 (d, J=4.8 Hz, 1H), 7.89 (d, J=4.8 Hz, 1H).

Synthesis of 4:

To a suspension of zinc powder (2.75 g, 42.0 mmol) in THF was added $TiCl_4$ (1.15 mL, 10.5 mmol) dropwise under a $N_2$ atmosphere at 0° C. The mixture was heated under reflux for 0.5 h then cooled to 0° C. A THF solution of cyclopenta[b]thiophen-6-one 3 (1.45 g, 10.5 mmol) was added dropwise, and the mixture was heated under reflux again overnight. The gray mixture was cooled to 25° C., and filtered through a Celite® pad. The filtrate was washed with water, then extracted with $CH_2Cl_2$. The organic phase was dried over $Na_2SO_4$, and evaporated to give an orange solid. The compound was purified by silica column chromatography ($CH_2Cl_2$) and re-precipitated from a $CH_2Cl_2$/methanol mixture to afford C5TVT 4 as an orange solid (929 mg, yield: 72%). $^1$H NMR (400 MHz, $CDCl_3$): δ (ppm)=3.00-3.03 (m, 4H), 3.25-3.28 (m, 4H), 6.91 (d, J=4.9 Hz, 2H), 7.31 (d, J=4.9 Hz, 2H).

Synthesis of 5:

6,6'-Bis(4,5-dihydro-6H-cyclopenta[b]thienylidene) 4 (100 mg, 0.41 mmol) was dissolved in 25 mL of THF, and the solution was cooled to −78° C. Then, 0.36 mL (0.90 mmol) of n-BuLi (2.5 M in hexane) was injected slowly into the solution. The mixture was warmed to 25° C. and stirred for 2 h. The temperature of the solution was decreased to −78° C. again, and 0.90 mL (0.90 mmol) of trimethylstannane chloride ($Me_3SnCl$: 1 M in hexane) was injected into the solution. The mixture was warmed to 25° C., and stirred overnight. An aqueous solution of $NH_4Cl$ was added to quench the reaction, and the mixture was extracted with $CH_2Cl_2$. The organic phase was dried over $Na_2SO_4$, then evaporated to give the stannylated compound C5TVT-tin 5 (228 mg, yield: 98%). $^1$H NMR (400 MHz, $CDCl_3$): δ (ppm)=0.37 (s, 18H), 2.98-3.00 (m, 4H), 3.31-3.32 (m, 4H), 6.97 (s, 2H). $^{13}$C NMR (400 MHz, $CDCl_3$): δ (ppm)=−7.90, 27.03, 36.33, 126.32, 131.19, 143.70, 150.62, 152.61.

Example 1b: Synthesis of 4,4'-bis(2-trimethylstannyl-5,6-dihydro-4H-cyclopenta[b]thienylidene) (C5RTVT-tin)

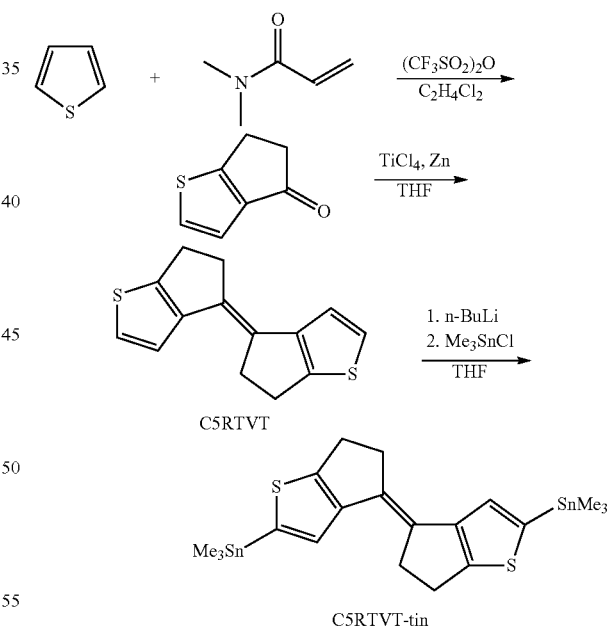

The isomer of 5, C5RTVT-tin, can be synthesized similarly by McMurry coupling of 5,6-dihydro-4H-cyclopenta[b]thiophen-4-one followed by stannylation. Various synthetic routes to 5,6-dihydro-4H-cyclopenta[b]thiophen-4-one are known in the art. For example, as described in International Publication No. WO2006084688, thiophene can be reacted with N,N-dimethyl-2-propenamide as a mixture with triflic anhydride in DCE as shown in the above scheme.

Example 1c: Synthesis of 4,4'-bis[2-trimethylstannyl-(6,7-dihydrobenzo[b]thiophen-4(5H)-ylidene)-4,5,6,7-tetrahydro] (C6RTVT-tin)

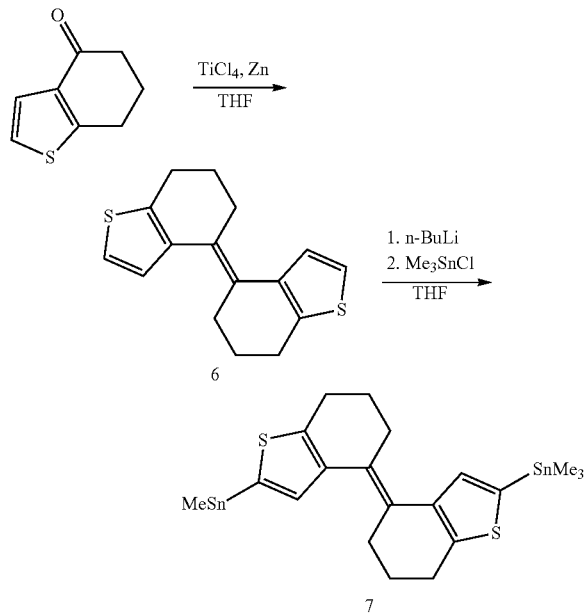

Example 1d: Synthesis of stannylated (E)-4,4'-bis(2-ethylhexyl)-4,4',5,5'-tetrahydro-6,6'-bi(cyclopenta[b]thiophenylidene) (C5$^{2EH}$TVT-tin)

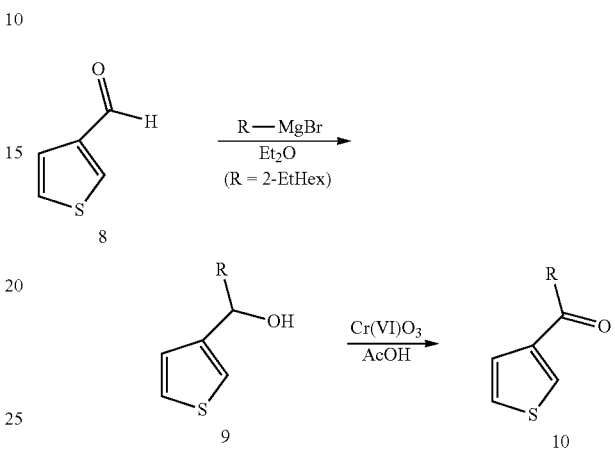

Synthesis of 6:

To a suspension of zinc powder (568 mg, 8.7 mmol) in THF was added TiCl$_4$ (237 μL, 2.2 mmol) dropwise under a N$_2$ atmosphere at 0° C. The mixture was heated under reflux for 0.5 h, then cooled to 0° C. A THF solution of 6,7-dihydro-1-benzothiophen-4(5H)-one (300 mg, 2.2 mmol) was added dropwise, and the mixture was heated at 50° C. overnight. The gray mixture was cooled to 25° C., and filtered through Celite® pad. The filtrate was washed with water, extracted with CH$_2$Cl$_2$. The organic phase was dried over Na$_2$SO$_4$, and evaporated to give an orange solid. The compound was purified by silica column chromatography (CH$_2$Cl$_2$) and recrystallization from CH$_2$Cl$_2$/methanol to afford C6RTVT 6 as a white solid (170 mg, yield: 58%). $^1$H NMR (400 MHz, CDCl$_3$): δ (ppm)=1.98 (m, 2H), 2.77 (m, 2H), 2.93 (t, J=6.4 Hz, 2H), 7.08 (d, J=5.3 Hz, 2H), 7.10 (d, J=5.3 Hz, 2H). $^{13}$C NMR (101 MHz, CDCl$_3$): δ (ppm)=25.81, 25.95, 30.90, 121.31, 127.59, 128.80, 136.66, 139.43.

Synthesis of 7:

Compound 6 (100 mg, 0.37 mmol) was dissolved in 20 mL of THF, and the solution was cooled to −78° C. Then, 0.32 mL (0.81 mmol) of n-BuLi (2.5 M in hexane) was injected slowly into the solution. The mixture was stirred at −78° C. for 0.5 h, and warmed to 25° C. and stirred for another 2 h. The temperature of the solution was decreased to −78° C. again, and 0.93 mL (0.93 mmol) of trimethylstannane chloride (Me$_3$SnCl: 1 M in hexane) was injected into the solution. The mixture was stirred at −78° C. for 1 h, and then stirred for another 5 h at 25° C. NH$_4$Cl (aq.) was added to quench the reaction, and the mixture was extracted with CH$_2$Cl$_2$. The organic phase was dried over Na$_2$SO$_4$, and evaporated to give the stannylated compound C6RTVT-tin 7 (230 mg, yield: 99%). $^1$H NMR (500 MHz, CDCl$_3$): δ (ppm)=0.36 (s, 18H), 1.98 (m, 4H), 2.80 (m, 4H), 2.97 (t, J=6.4 Hz, 4H), 7.15 (s, 2H). $^{13}$C NMR (126 MHz, CDCl$_3$): δ (ppm)=−7.95, 26.09, 26.18, 31.10, 127.57, 133.11, 136.85, 138.43, 145.17.

Synthesis of 10:

To a solution of (2-ethylhexyl)magnesium bromide (1 M in Et$_2$O, 22 mmol), a solution of 3-thiophene carboxaldehyde 8 (1.8 mL, 20 mmol) in 5 mL of Et$_2$O was added over 10 min at 0° C. The reaction mixture was warmed to 25° C. and stirred for 23 h. The mixture was poured into a mixture of ice water (80 mL) and conc. HCl (15 mL), and extracted with Et$_2$O (100 mL×3). The organic phases were dried over Na$_2$SO$_4$ and evaporated to afford a brown oil of the intermediate alcohol 9. The alcohol 9 was dissolved in acetic acid (10 mL), and a solution of Cr(VI)O$_3$ (2.1 g, 21 mmol) in 15 mL of acetic acid/water (2:1) was added dropwise. The reaction mixture was stirred for 3 h at 25° C. After the further addition of water (30 mL), the mixture was extracted with Et$_2$O (80 mL×3). The organic phase was washed with a saturated aqueous solution of Na$_2$CO$_3$ until neutralization. The organic phase was dried over Na$_2$SO$_4$ and evaporated to give a brown oil. The resulting oil was purified by a short silica column (CH$_2$Cl$_2$) to give the 3-acetylthiophene 8 as a yellow oil (3.52 g, yield: 78%). $^1$H NMR (400 MHz, CDCl$_3$): d (ppm)=0.80-0.89 (m, 6H), 1.16-1.44 (m, 8H), 2.00 (m, 1H), 2.76 (m, 2H), 7.29 (dd, J=5.1, 2.9 Hz, 1H), 7.53 (dd, J=5.1, 1.3 Hz, 1H), 8.01 (dd, J=2.9, 1.3 Hz, 1H). $^{13}$C NMR (101 MHz, CDCl$_3$): d (ppm)=11.26, 14.43, 23.31, 26.84, 29.26, 33.63, 36.19, 44.81, 126.53, 127.42, 131.98, 143.28, 195.45.

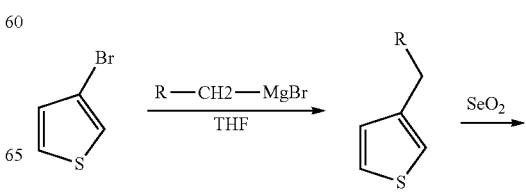

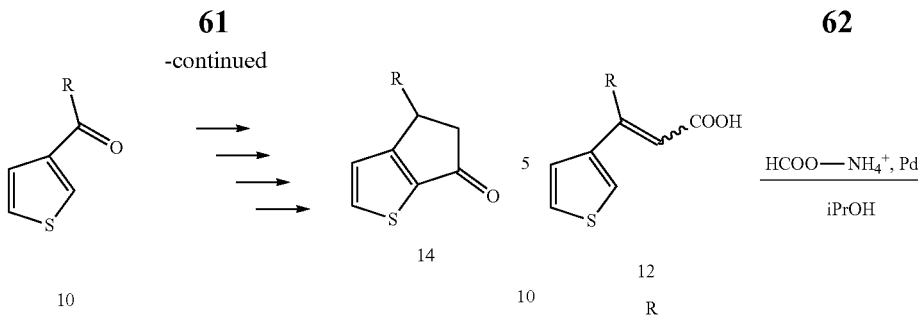

Alternative Synthesis of 10:

Alternatively, the 3-acetylthiophene 8 can be synthesized from 3-bromothiophene as described in the scheme above, which then can be used to prepare the ketone 14 as described below.

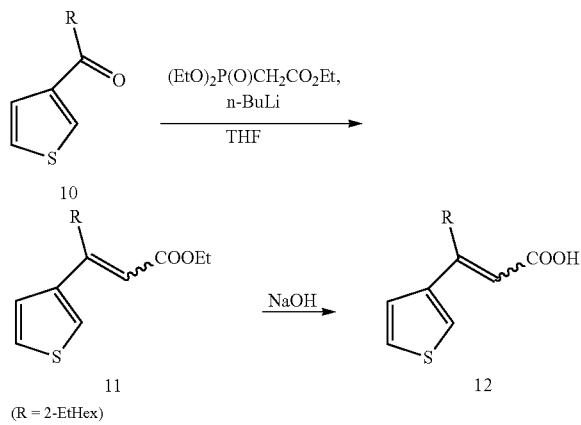

Synthesis of 12:

To a solution of triethyl phosphonoacetate (9.4 mL, 48 mmol) in THF (35 mL) was added a 2.5 M hexane solution of n-BuLi (19.5 mL, 49 mmol) dropwise at −60° C. under a N$_2$ atmosphere over 15 min. The reaction mixture was stirred for 2.5 h at −60° C., and then a THF solution of the 3-acetylthiophene 8 (3.52 g, 16 mmol) was added over 20 min. The dark orange solution was gradually warmed to 25° C., and stirred for 24 h at 25° C. and 48 h at 65° C. The solution was treated with aqueous NH$_4$Cl and HCl, and extracted with CH$_2$Cl$_2$ (100 mL×3). The organic phases were dried over Na$_2$SO$_4$ and evaporated to give a brown oil. The product was purified by silica gel chromatography (CH$_2$Cl$_2$/hexane=2:1) to afford a yellow oil as a second fraction corresponding to the intermediate ester 11. A mixture of the ester 11 and an aqueous solution of NaOH (10%) in EtOH was heated to reflux for 2 h. The reaction mixture was cooled to 25° C., and poured into a 10% aqueous solution of HCl. The mixture was extracted with CH$_2$Cl$_2$ (50 mL×3), washed with water, and dried over Na$_2$SO$_4$. The resulting organic phase was dried under vacuum to yield a clear, colorless oil corresponding to a mixture of the Z and E isomers of the unsaturated carboxylic acid 12 (yield 84%). Main isomer: $^1$H NMR (500 MHz, CDCl$_3$): d (ppm)=0.79-0.87 (m, 6H), 1.15-1.32 (m, 9H), 2.40 (d, J=5.5 Hz, 2H), 5.85 (s, 1H), 7.04-7.05 (m, 1H), 7.25-7.28 (m, 2H). $^{13}$C NMR (126 MHz, CDCl$_3$): d (ppm)=10.86, 14.42, 23.26, 25.81, 28.88, 32.60, 37.53, 45.60, 117.54, 124.49, 124.97, 128.28, 139.02, 156.14, 170.57.

Synthesis of 14:

Pd/C (300 mg, 10 wt %) and ammonium formate (845 mg, 13 mmol) were added to an isopropyl alcohol solution of the unsaturated carboxylic acid 12 (1.19 g, 4.4 mmol) under a N$_2$ atmosphere. The mixture was stirred overnight at 80° C., and then concentrated. The mixture was dissolved in CH$_2$Cl$_2$, filtered through a Celite® pad, and evaporated under reduced pressure to afford the intermediate saturated carboxylic acid 13 as a clear, colorless oil. A chloroform solution (10 mL) of the saturated carboxylic acid 13 in the presence of a catalytic amount of DMF (0.05 mL) was treated dropwise with thionyl chloride (0.48 mL, 6.6 mmol) under a N$_2$ atmosphere at 25° C. The mixture was then heated under reflux for 2 h. The resulting solution was cooled, and concentrated in vacuo to give a dark orange oil. A 1,2-dichloroethane (DCE) solution of the carboxylic acid chloride was added dropwise to a suspension of AlCl$_3$ (587 mg, 4.4 mmol) in DCE at 25° C. The mixture was stirred for 12 h at 25° C., and heated under reflux for 1 h, and then poured into an aqueous solution of HCl (5%). The mixture was extracted with CH$_2$Cl$_2$, dried over Na$_2$SO$_4$, and evaporated. The residue was purified by silica gel chromatography (CH$_2$Cl$_2$/hexane=5:1) to give a transparent oil of the ketone 14 (0.91 g, yield: 73%). One Stereoisomer: $^1$H NMR (400 MHz, CDCl$_3$): d (ppm)=0.86-0.92 (m, 6H), 1.22-1.57 (m, 10H), 1.63-1.72 (m, 1H), 2.56-2.62 (m, 1H), 3.09-3.16 (m, 1H), 3.34-3.36 (m, 1H), 7.04 (d, J=4.8 Hz, 1H), 7.87 (d, J=4.8 Hz, 1H). $^{13}$C NMR (101 MHz, CDCl$_3$): d (ppm)= 10.84, 14.47, 23.42, 25.91, 28.99, 32.92, 35.11, 37.70, 40.42, 48.70, 123.34, 140.61, 140.75, 173.67, 197.03.

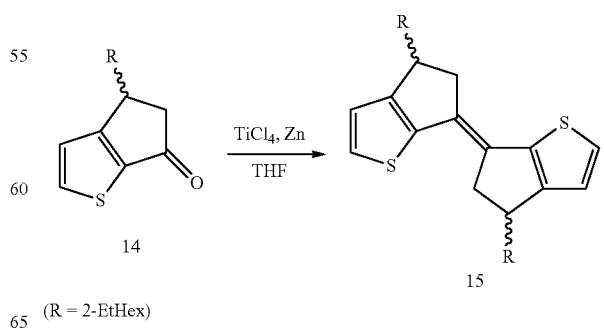

Synthesis of 15:

To a suspension of zinc powder (836 mg, 14.4 mmol) in THF was added TiCl$_4$ (0.35 mL, 3.6 mmol) dropwise under a N$_2$ atmosphere at 0° C. The mixture was then heated under reflux for 0.5 h and cooled to 0° C. again. A THF solution of the ketone 14 (664 mg, 2.7 mmol) was added dropwise, and the mixture was stirred at 45° C. for 14 h. The mixture was cooled to 25° C., and filtered through a Celite® pad. The filtrate was washed with water, extracted with CH$_2$Cl$_2$. The organic phase was dried over Na$_2$SO$_4$, and evaporated to give a brown oil. The compound was purified by silica column chromatography (CH$_2$Cl/hexane=1:6) to give an orange oil corresponding to the (E)-isomer 15 (405 mg, yield: 58%). One stereoisomer: $^1$H NMR (500 MHz, CDCl$_3$): d (ppm)=0.87-0.92 (m, 12H), 1.27-1.53 (m, 20H), 1.57-1.66 (m, 2H), 2.81 (m, 2H), 3.40 (m, 4H), 6.90 (d, J=4.9 Hz, 2H), 7.29 (d, J=4.9 Hz, 2H). $^{13}$C NMR (126 MHz, CDCl$_3$): d (ppm)=10.98, 14.53, 23.53, 26.38, 29.08, 33.23, 37.26, 38.46, 41.53, 43.09, 122.99, 125.74, 129.43, 143.37, 154.86.

hexane) was injected slowly into the solution. The mixture was stirred for 0.5 h at −78° C., gradually warmed to 25° C., and stirred for 2 h. The dark-brown solution was cooled to −78° C., and 2.13 mL (2.1 mmol) of trimethylstannane chloride (Me$_3$SnCl: 1 M in hexane) was injected into the solution. The mixture was stirred for 0.5 h at −78° C., gradually warmed to 25° C., and stirred overnight. Aqueous NH$_4$Cl was added to quench the reaction, and the mixture was extracted with CH$_2$Cl$_2$. The organic phase was dried over Na$_2$SO$_4$, and evaporated to give the stannylated compound 16 as a brown sticky solid (659 mg, yield: 98%). One stereoisomer: $^1$H NMR (500 MHz, CDCl$_3$): d (ppm)=0.32-0.43 (m, 18H), 0.89-0.93 (m, 12H), 1.30-1.51 (m, 22H), 2.87 (m, 2H), 3.35 (m, 2H), 3.45 (m, 2H), 6.96 (s, 2H). 13C NMR (126 MHz, CDCl$_3$): d (ppm)=−7.85, 10.91, 14.53, 23.55, 26.55, 28.99, 33.01, 37.21, 37.90, 41.53, 43.72, 125.64, 130.74, 149.71, 156.90, 172.85.

Example 1e: Synthesis of C6TVT

The scheme below provides a possible synthetic route for preparing building block 25. (C6TVT)

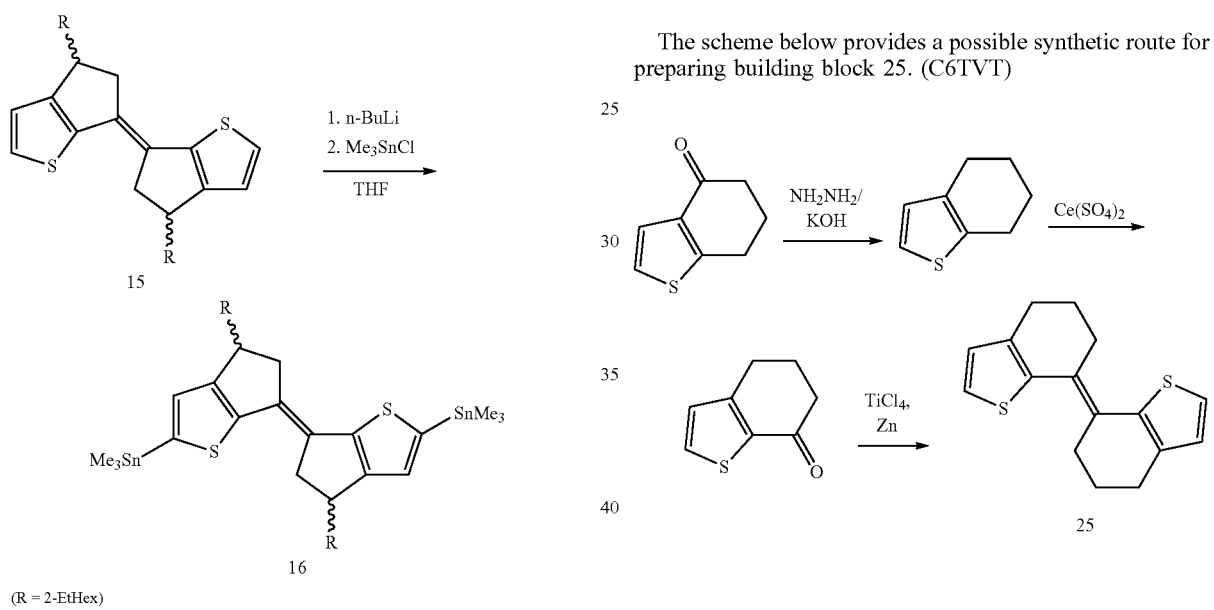

(R = 2-EtHex)

Example 1f: Synthesis of Additional pi-1 Building Blocks

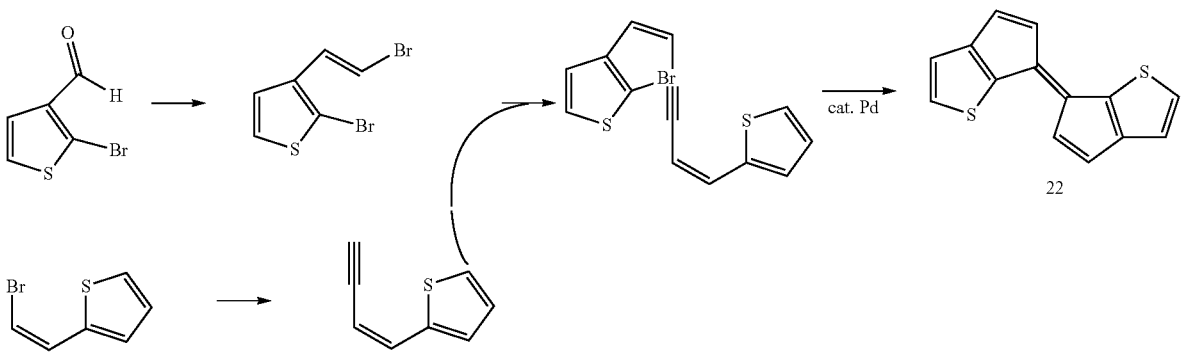

Synthesis of 16:

The thienyl-vinylene derivative 15 (400 mg, 0.85 mmol) was dissolved in 25 mL of THF, and the solution was cooled to −78° C. Then 0.75 mL (1.9 mmol) of n-BuLi (2.5 M in The scheme above provides a possible synthetic route for preparing building block 22. Alternatively, building block 22 can be prepared from ketone 3 as illustrate in the prophetic scheme below:

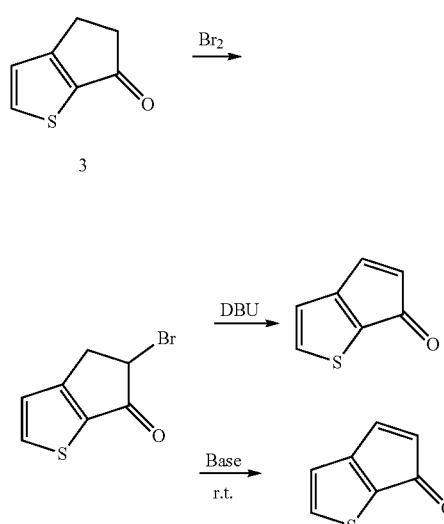
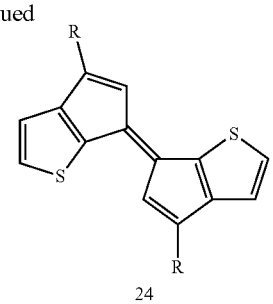
Alternatively, building block 24 can be prepared from ketone 14 as illustrated in the prophetic scheme below:
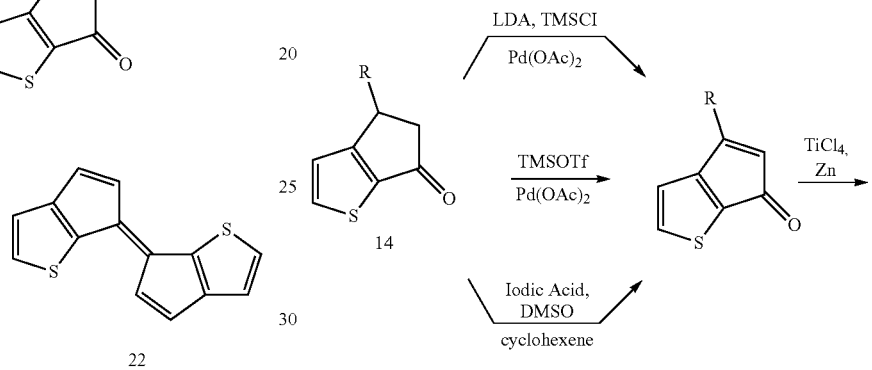
Building block 24 can be prepared from building block 22 as illustrated in the prophetic scheme below:
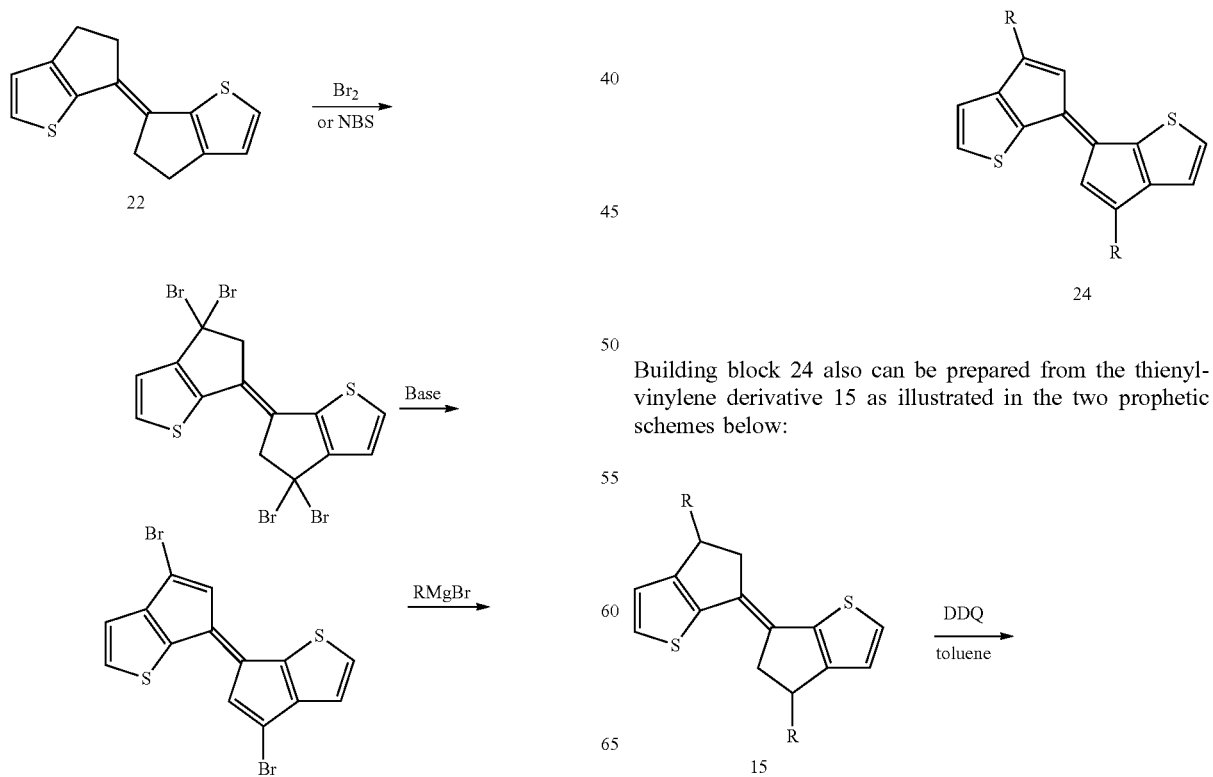
Building block 24 also can be prepared from the thienyl-vinylene derivative 15 as illustrated in the two prophetic schemes below:

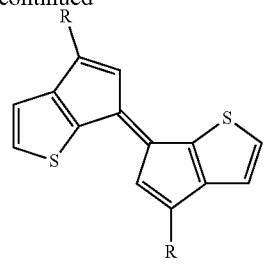

24

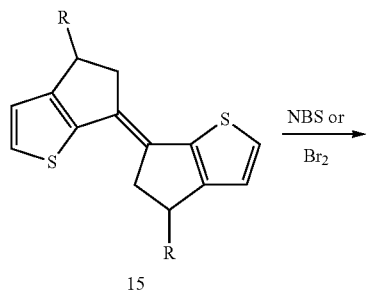

15

NBS or Br₂ →

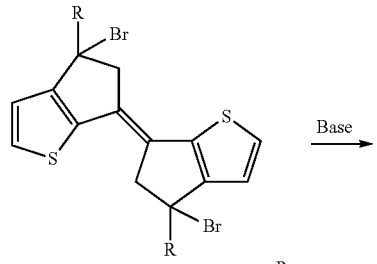

Base →

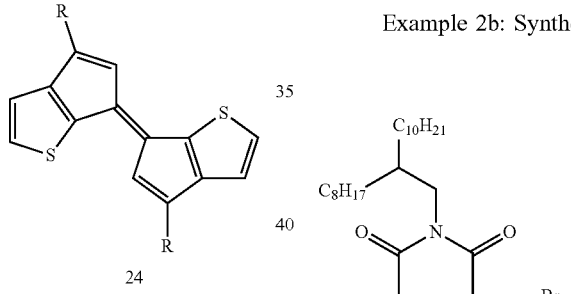

24

Example 2: Synthesis of Polymers

Example 2a: Synthesis of P(NDI-C5TVT)

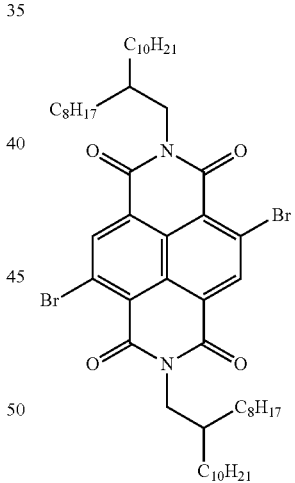

Under argon, a mixture of N,N'-bis(2-octyldodecyl)-2,6-dibromonaphthalene-1,4,5,8-bis(dicarboximide) (NDI-Br$_2$, 146.9 mg, 0.15 mmol), C5TVT-tin reagent 5 (85.0 mg, 0.15 mmol), and Pd(PPh$_3$)$_2$Cl$_2$ (4.2 mg, 0.0060 mmol) in anhydrous toluene (20 mL) was stirred at 90° C. for 17 h. Bromobenzene (0.5 mL) was then added and the reaction mixture was maintained at 90° C. for an additional 22 h. Upon cooling to room temperature, the reaction mixture was precipitated in methanol (50 mL). The crude product was collected by filtration, washed with methanol, and re-dissolved in chloroform (50 mL). This solution was precipitated in acetone (100 mL). The obtained solid product was subject to Soxhlet extraction with methanol (18 h), acetone (26 h), and hexane (18 h). Finally, the product was extracted with chloroform, and the resulting extract was concentrated to about 50 mL, filtered, and precipitated in methanol (80 mL). The precipitate was collected by filtration, washed with methanol, and dried in vacuum, leading to a dark solid as the product P(NDI2-CaTVT) (140.1 mg, 88.1%). $^1$H NMR (CDCl$_2$CD$_2$Cl$_2$, 400 MHz): δ: 8.30-8.84 (m, br, 2H), 6.80-7.50 (m, br, 2H), 4.11 (m, br, 4H), 3.37 (m, br, 4H), 3.20 (m, br, 4H), 1.98 (s, br, 2H), 0.94-1.60 (m, br, 64H), 0.86 (s, br, 12H). Elemental Analysis (calc. C, 76.27; H, 8.76; N, 2.56): found C, 75.99; H, 8.88; N, 2.71.

Example 2b: Synthesis of P(NDI-C6RTVT)

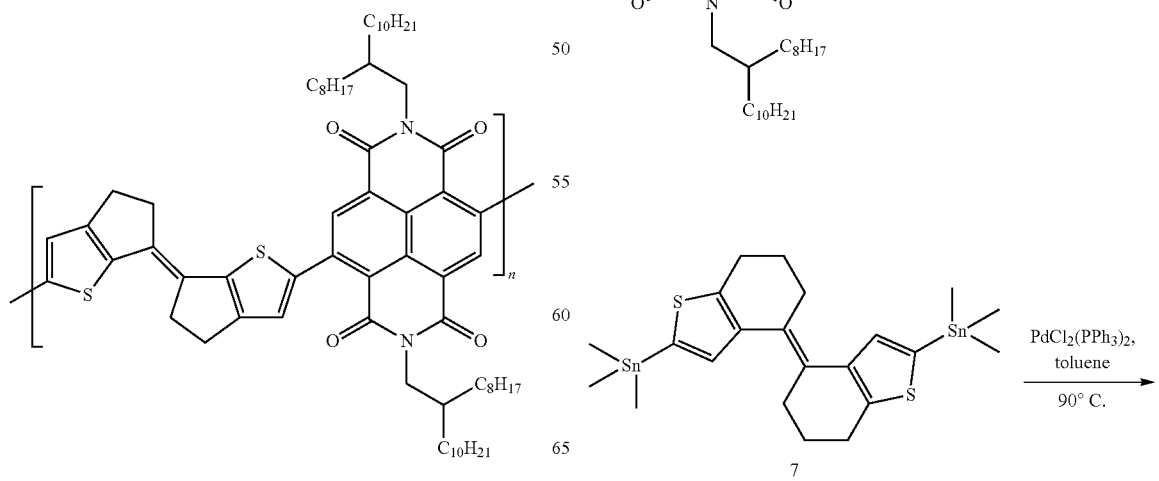

7

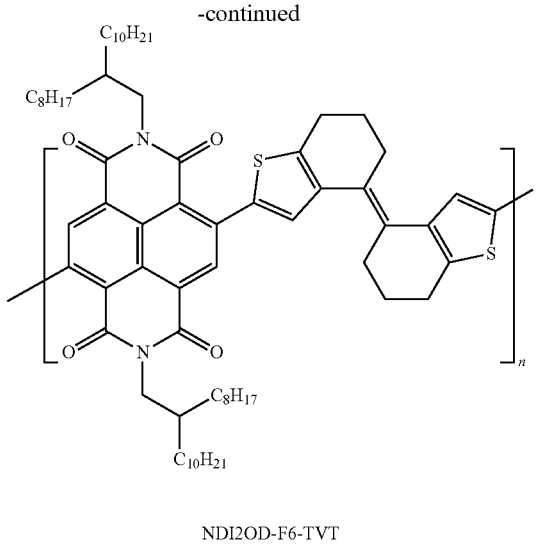

NDI2OD-F6-TVT

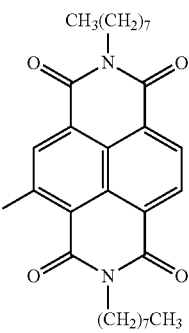

NDI-Br

+

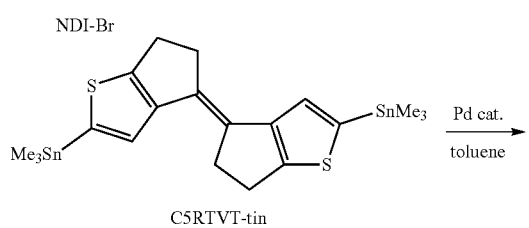

C5RTVT-tin

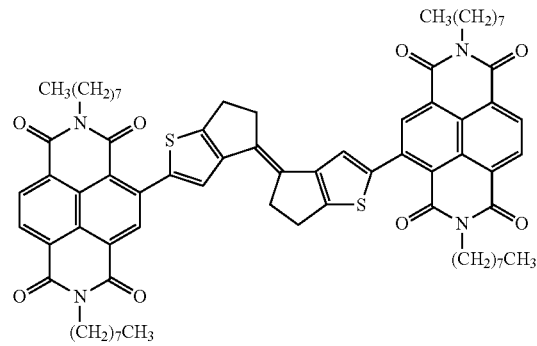

NDI-C5RTVT-NDI

Under argon, a mixture of NDI-Br$_2$ (152.9 mg, 0.16 mmol), C6RTVT-tin reagent 7 (92.8 mg, 0.16 mmol), and Pd(PPh$_3$)$_2$Cl$_2$ (4.3 mg, 0.0061 mmol) in anhydrous toluene (15 mL) was stirred at 90° C. for 20 h. Bromobenzene (0.2 mL) was then added and the reaction mixture was maintained at 90° C. for an additional 12 h. Upon cooling to room temperature, the reaction mixture was precipitated in methanol (100 mL). The crude product was collected by filtration, and washed with methanol (100 mL). This crude solid product was subject to Soxhlet extraction with methanol (18 h) and acetone (20 h). Finally, the product was extracted with chloroform, and the resulting extract was concentrated in vacuo. The residue was taken with THF (about 5 mL), and this solution was precipitated in methanol (50 mL). The precipitate was collected by filtration, washed with methanol, and dried in vacuum, leading to a greenish dark solid as the product P(NDI2-C6RTVT) (136.7 mg, 80.4%). $^1$H NMR (CDCl$_3$, 400 MHz): δ: 8.81 (m, br, 2H), 7.40 (m, br, 2H), 4.12 (m, br, 4H), 3.05 (m, br, 4H), 2.92 (m, br, 4H), 2.11 (m, br, 4H), 2.02 (m, br, 2H), 1.10-1.48 (m, br, 64H), 0.80-90 (m, br, 12H).

Using the building blocks C5RTVT-tin and NDI-Br$_2$, P(NDI-C5RTVT) was synthesized analogously via Stille coupling:

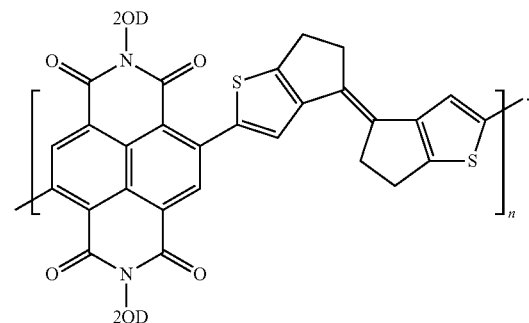

Dimers of NDI linked by a C5RTVT spacer were synthesized according to the scheme below:

Example 2c: Synthesis of P(DPP-C5TVT)

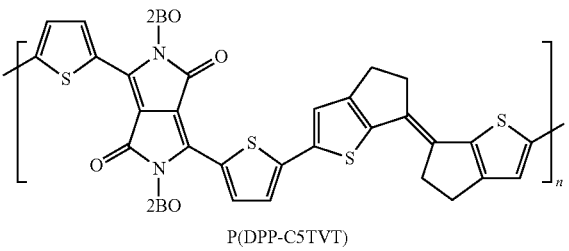

P(DPP-C5TVT)

Under argon, a mixture of 3,6-bis-(5-bromo-thiophen-2-yl)-2,5-bis-(2-butyl-octyl)-2,5-dihydro-pyrrolo[3,4-c]pyrrole-1,4-dione (DPP-Br$_2$, 118.8 mg, 0.15 mmol), C5TVT-tin reagent 5 (85.2 mg, 0.15 mmol), and Pd$_2$dba$_3$ (2.7 mg, 0.0029 mmol), and tol$_3$P (7.3 mg, 0.024 mmol) in anhydrous chlorobenzene (10 mL) was stirred at 130° C. for 18 h. Bromobenzene (0.2 mL) was then added and the reaction mixture was maintained at 130° C. for an additional 4 h. Upon cooling to room temperature, the reaction mixture was precipitated in methanol (50 mL). The crude product was collected by filtration, then washed with methanol. The obtained solid product was subject to Soxhlet extraction with methanol (18 h), acetone (20 h), and hexane (8 h). A portion of the product was then extracted with chloroform, and the resulting extract was concentrated to about 5 mL, filtered, and precipitated in methanol (50 mL). The precipitate was collected by filtration, washed with methanol, and dried in vacuum, leading to a dark greenish solid (32.1 mg). The remaining dark greenish solid P(DPP-C5TVT) in thimble was collected and dried in vacuum (53.8 mg) (total yield: 65.3%). $^1$H NMR (CDCl3, 400 MHz): δ: 8.88-9.12 (m, br, 4H), 6.70-7.40 (m, br, 2H), 3.70-4.22 (m, br, 8H), 2.70-3.10 (m, br, 4H), 1.96 (m, br, 2H), 1.00-1.50 (m, br, 32H), 0.85 (s, br, 12H).

Example 2c: Synthesis of P(BDT-C5TVT)

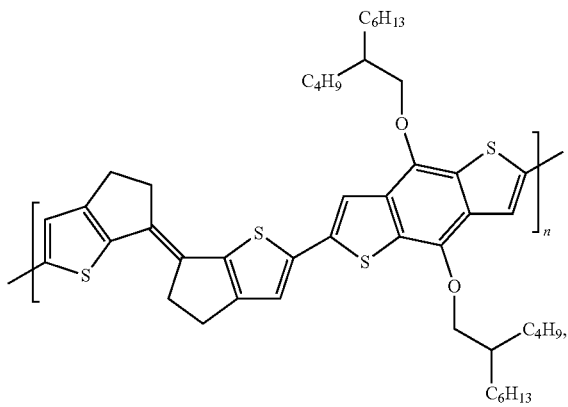

Under argon, a mixture of 4,8-bis-(2-butyl-octyloxy)-2,6-bis-bromo-1,5-dithia-s-indacene (BDT-Br$_2$, 98.4 mg, 0.14 mmol), C5TVT-tin reagent 5 (78.3 mg, 0.14 mmol), and Pd$_2$dba$_3$ (2.5 mg, 0.0027 mmol), and tol$_3$P (6.7 mg, 0.022 mmol) in anhydrous chlorobenzene (10 mL) was stirred at 130° C. for 17 h. Bromobenzene (0.2 mL) was then added and the reaction mixture was maintained at 130° C. for an additional 4 h. Upon cooling to room temperature, the reaction mixture was precipitated in methanol (50 mL). The crude product was collected by filtration, then washed with methanol. The obtained solid product was subject to Soxhlet extraction with methanol (18 h), acetone (20 h), and hexane (8 h). Finally, the product was extracted with chloroform, and the resulting extract was concentrated to about 5 mL, filtered, and precipitated in methanol (50 mL). The precipitate was collected by filtration, washed with methanol, and dried in vacuum, leading to a deep purple solid as the product P(BDT-C5TVT) (63.1 mg, 56.4%). $^1$H NMR (CDCl$_3$, 400 MHz): δ: 6.00-7.80 (m, br, 4H), 3.70-4.30 (m, br, 8H), 2.20-3.40 (m, br, 4H), 0.70-2.00 (m, br, 46H).

Example 2e: Synthesis of P(C12-BTZ-C12-C5TVT)

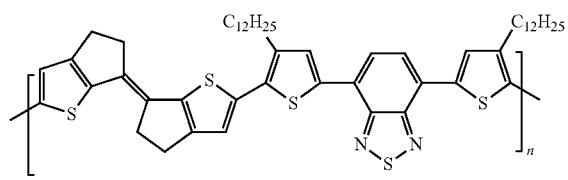

Under argon, a mixture of 4,7-bis-(5-bromo-4-dodecyl-thiophen-2-yl)-benzo[1,2,5]thiadiazole (C12-Br$_2$, 142.05 mg, 0.18 mmol), C5TVT-tin reagent 5 (101.86 mg, 0.18 mmol), Pd$_2$dba$_3$ (6.5 mg, 0.00715 mmol) and tol$_3$P (8.7 mg, 0.0286 mmol) in anhydrous chlorobenzene (20 mL) was stirred at 90° C. for 18 h. Upon cooling to room temperature the reaction mixture was precipitated in methanol (100 mL). The crude product was collected by filtration and washed with methanol. The obtained solid product was subjected to sequential Soxhlet extractions with methanol (17 h), ethyl acetate (24 h) and chloroform (4 h) under N$_2$. The chloroform fraction was concentrated under reduced pressure to ~20 mL and the polymer was precipitated into methanol (100 mL). The precipitate was collected by vacuum filtration and washed with methanol (3×10 mL). The polymer was re-dissolved in chloroform (20 mL) and slowly dripped into stirring acetone (50 mL). The precipitate was collected by vacuum filtration, washed with acetone (3×10 mL) and methanol (3×10 mL) and dried under vacuum to give a dark solid as the product P(C12-BTZ-C12-CaTVT) (70 mg, 45%). Elemental Analysis (calc. C, 71.18; H, 7.35; N, 3.19): found C, 68.22; H, 7.11; N, 3.05.

Example 2f: Synthesis of P(C12-BTZ$^{Cl}$-C12-C5TVT)

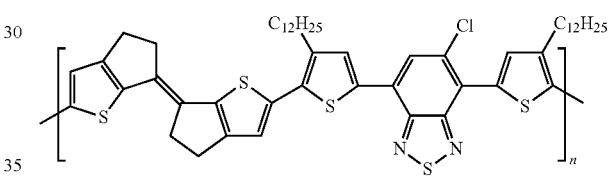

Under argon, a mixture of 4,7-bis-(5-bromo-4-dodecyl-thiophen-2-yl)-5-chloro-benzo[1,2,5]thiadiazole (C1-C12-Br$_2$, 130.61 mg, 0.16 mmol), C5TVT-tin reagent 5 (89.77 mg, 0.16 mmol), Pd$_2$dba$_3$ (5.8 mg, 0.0063 mmol) and tol$_3$P (7.7 mg, 0.025 mmol) in anhydrous chlorobenzene (20 mL) was stirred at 90° C. for 18 h. Upon cooling to room temperature, the reaction mixture was precipitated in methanol (100 mL). The crude product was collected by filtration and washed with methanol. The obtained solid product was subjected to sequential Soxhlet extractions with methanol (19 h), ethyl acetate (21 h), hexanes (19 h) and chloroform (3 h) under N$_2$. The chloroform fraction was added to methanol (400 mL) and the mixture was concentrated under a stream of N$_2$ with stirring to 250 mL. The precipitate was collected by vacuum filtration, washed with methanol (3×10 mL) and dried under vacuum (dark solid, 27 mg, 19%). Elemental Analysis (calc. C, 68.50; H, 6.96; N, 3.07): found C, 66.90; H, 6.89; N, 2.83.

Example 2g: Synthesis of Random Copolymer P(C12-BTZ-C12-C5TVT-co-C0-BTZ-C0-C5TVT)

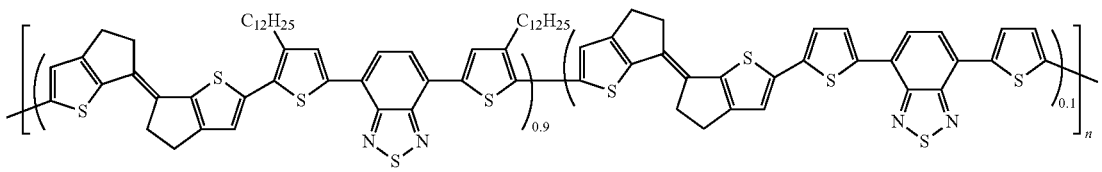

Under argon, a mixture of C12-Br₂ (62.5 mg, 0.079 mmol), 4,7-bis-(5-bromo-thiophen-2-yl)-benzo[1,2,5]thiadiazole (C0-Br₂, 4.0 mg, 0.0087 mmol), F5 TVT-tin reagent 5 (49.8 mg, 0.087 mmol), and Pd₂dba₃ (1.6 mg, 0.0017 mmol), and tol₃P (4.3 mg, 0.014 mmol) in anhydrous chlorobenzene (8 mL) was stirred at 130° C. for 8 h. Bromobenzene (0.1 mL) was then added and the reaction mixture was maintained at 130° C. for an additional 4 h. Upon cooling to room temperature, the reaction mixture was precipitated in methanol (50 mL). The crude product was collected by filtration, washed with methanol, and dried in vacuum, leading to a dark solid as the product (70.0 mg, 95.4%).

Example 2h: Synthesis of Random Copolymer P(DPP-C5$^{2EH}$TVT)

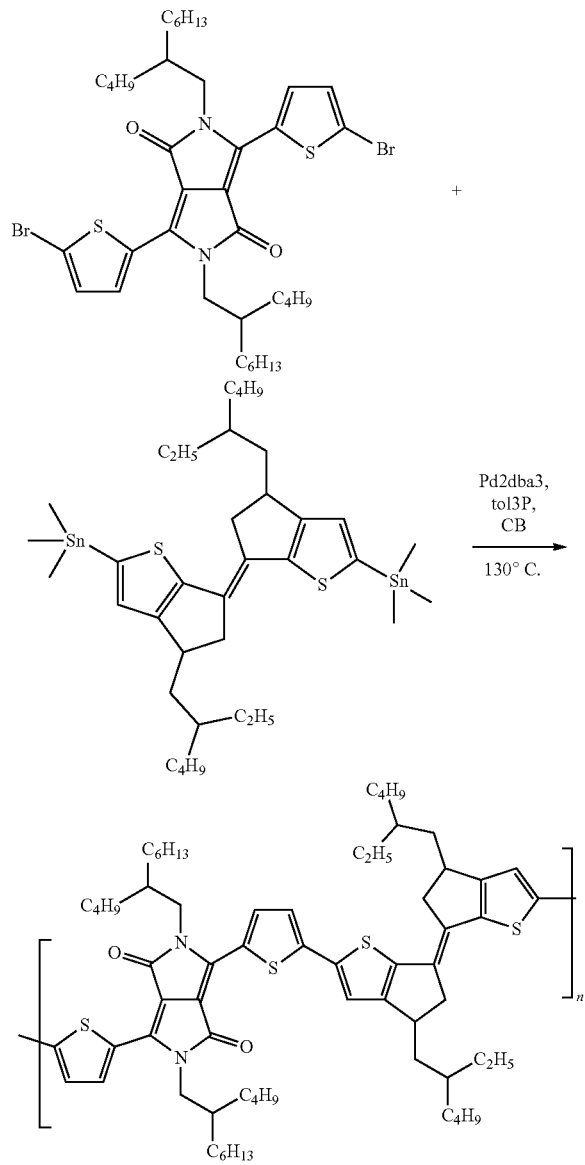

Under argon, a mixture of 3,6-bis-(5-bromo-thiophen-2-yl)-2,5-bis-(2-butyl-octyl)-2,5-dihydro-pyrrolo[3,4-c]pyrrole-1,4-dione (DPP-Br₂, 63.2 mg, 0.080 mmol), C5$^{2EH}$TVT-tin reagent (16, 63.2 mg, 0.080 mmol), and Pd₂dba₃ (1.5 mg, 0.0016 mmol), and tol₃P (3.9 mg, 0.013 mmol) in anhydrous chlorobenzene (10 mL) was stirred at 130° C. for 18 h. Bromobenzene (0.2 mL) was then added and the reaction mixture was maintained at 130° C. for an additional 8 h. Upon cooling to room temperature, the reaction mixture was precipitated in methanol (100 mL). The precipitate was collected by filtration, washed with methanol (~50 mL), and dried in vacuum, leading to a dark solid as the product (71.8 mg, 82.0%).

Example 3: Characterization of Monomers and Polymers

Table 1 below provides optical absorption data of certain embodiments of the present compounds in chloroform solution, as well as the optical band gaps estimated from the low energy band edge. Without wishing to be bound by any particular theory, it is noted that the optical absorption maxima and the absorption onset suggest a low energy gap for the monomer C5TVT (4) as compared to TVT

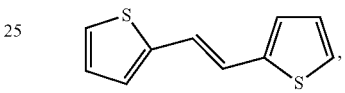

which is probably due to annulation. In addition, the polymers having the fused five (C5TVT or C5$^R$TVT) fusion (co-monomer 5 and 16 in the polymerization) exhibit a considerable red shift of the absorption maxima and/or a lower optical bandgap compared to the corresponding polymers with either a dithiophene (T2) co-monomer or a thienylvinylene (TVT) comonomer. This result could be ascribed to the increased planarization of the co-monomer, its more rigid structure, as well as the electron-donating properties of the C5 annulation. That planarization is the major factor affecting absorption is clear by the fact that when a fused six (C6RTVT) unit (co-monomer 7) is used, the optical absorption blue shifts and the bandgap is expanded.

TABLE 1

| Compounds | $\lambda_{max}$ (nm) | $E_{op}$ (EV) |
| --- | --- | --- |
| TVT | 342 | 3.31 |
| C5TVT (4) | 331, 348, 368 | 3.26 |
| P(NDI-T2) | 393, 697 | 1.52 |
| P(NDI-TVT) | 404, 693, 730 | 1.44 |
| P(NDI-C5TVT) | 447, 830, 916 | 1.18 |
| P(NDI-C6RTVT) | 325, 477, 623 | 1.65 |
| P(DPP-C5TVT) | 334, 416, 790 | 1.22 |
| P(DPP-C5$^{2EH}$TVT) | 412, 800 | 1.23 |
| P(C12-BDT-C12-C5TVT) | 474, 677, 724 | 1.43 |
| P(BDT-C5TVT) | 556, 598 | 1.79 |

Figure 2:
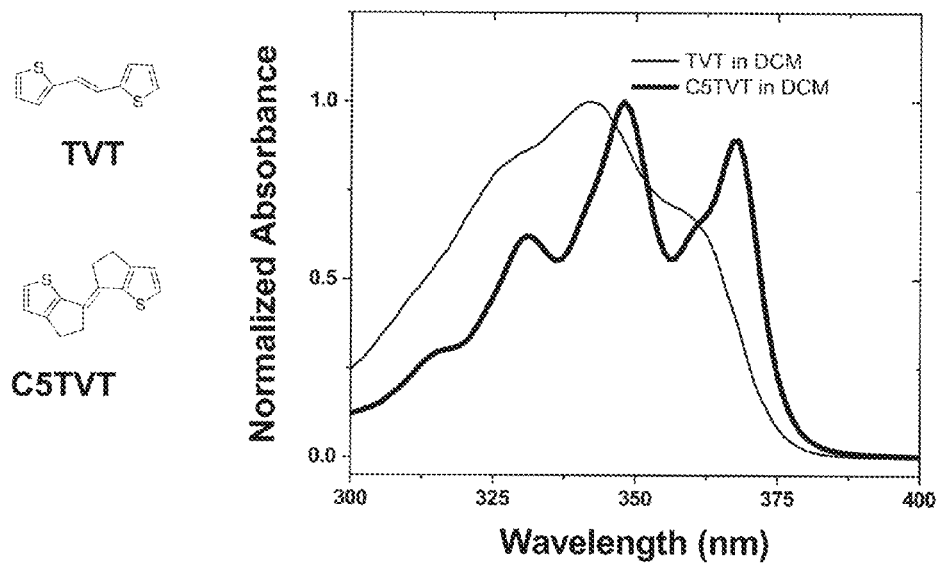
FIG. 2 compares the optical absorption spectra of 4,5-dihydro-6H-cyclopenta[b]thienylidene) (C5TVT) versus trans-1,2-di(2-thienyl)ethylene (TVT).
Figure 3:
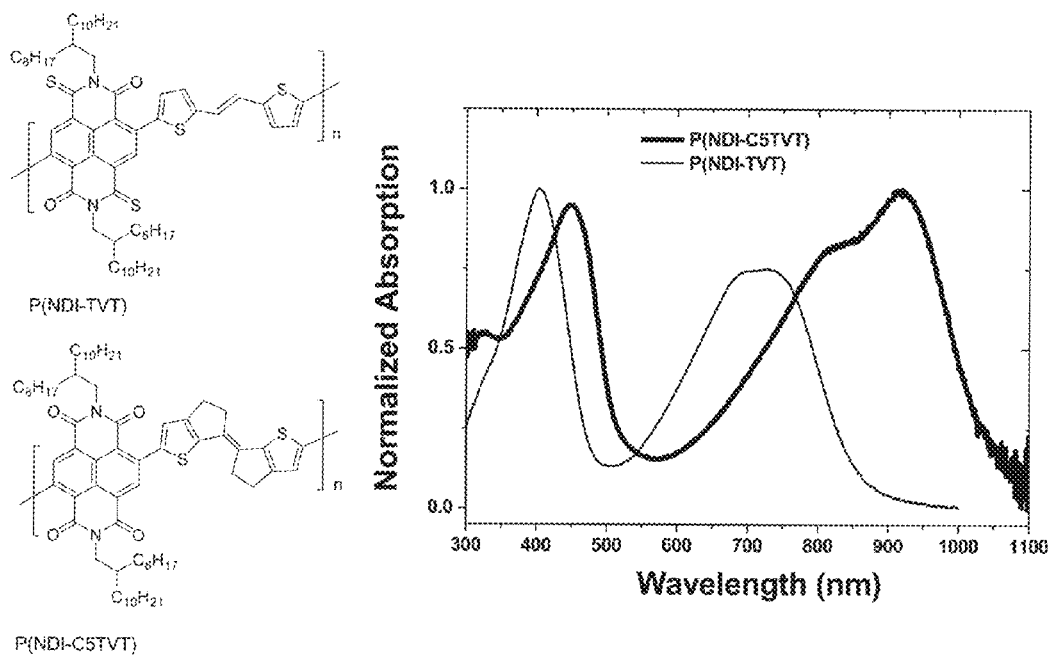
FIG. 3 compares the optical absorption spectra of a naphthalene tetracarboxylic diimide (NDI) polymer having a C5TVT co-monomer unit, P(NDI-C5TVT), versus an NDI polymer having a TVT co-monomer unit, P(NDI-TVT).

FIGS. 2 and 3 show the optical absorption spectra of monomer C5TVT as compared to TVT, and polymer P(NDI-C5TVT) as compared to P(NDI-TVT), respectively.

To investigate the redox properties of the present compounds, cyclic voltammetry experiments were performed using a THF-(NBu)₄PF₆ solvent-electrolyte solution, Pt as the working electrode, silver as the pseudo-reference electrode and ferrocene (0.54 V vs SCE) as the internal standard. The Pt working electrode was coated with a thin polymer film by drop-casting a CHCl₃ solution. Exemplary redox potential data including estimated frontier molecular orbital energies are provided in Table 2. These data evidence that in the case of the naphthalene-containing polymers the LUMO energy is pinned, as in the case of P(NDI-C5TVT). Thus, the effect of the C5 annulation of TVT mainly is on the energy of the HOMO.

TABLE 2

| Compound | $E_{red-1}^{onset}$ (V) | $E_{ox-1}^{onset}$ (V) | $E_{HOMO}^{b}$/$E_{LUMO}^{c}$ (eV) |
|---|---|---|---|
| P(NDI-T2) | −0.50 | — | −5.56/−3.94 |
| P(NDI-TVT) | −0.52[a] | — | −5.36/−3.92 |
| P(NDI-C5TVT) | −0.53[a] | — | −5.09/−3.91 |

[a]Half-wave first reduction potential.
[b]$E_{HOMO}$ calculated as: $-(E_{ox-1}^{onset} + 4.44\text{ eV})$ or calculated from: $E_g = $ LUMO − HOMO if oxidation peak is not observed.
[c]$E_{LUMO}$ calculated as: $-(E_{red-1}^{onset} + 4.44\text{ eV})$.

[a]Half-wave first reduction potential. [b]$E_{HOMO}$ calculated as: $-(E_{ox-1}^{onset} + 4.44$ eV) or calculated from: $E_g =$ LUMO−HOMO if oxidation peak is not observed. [c]$E_{LUMO}$ calculated as: $-(E_{red-1}^{onset} + 4.44$ eV).

Example 4—Device Fabrication and Characterization

Top-gate bottom-contact transistor (TFT) devices (50-100 μm channel lengths (L) and 1.0-4.0 mm channel widths (W)) were fabricated with the semiconductors films deposited by spin-coating a solution of chlorinated solvents (2-10 mg/mL) on top of Au electrodes/glass substrates. Next, the gate dielectric layer was spin-coated. Examples of gate dielectrics are PMMA, PS, PVA, PTBS and have thicknesses of 300-1500 nm. The device was completed by deposition of the gate Au contact. All electrical measurements were performed in ambient atmosphere.

A Keithley 4200 semiconductor characterization system was used to perform all electrical/TFT characterizations concerning the devices. The 4200 SCS system consists of three source measurement units (SMU), all of which are supplied with remote pre-amplifiers. The other major component of the test system is a Signatone probe station. Triax cable and probes were used for all electrodes to provide the first level of shielding. A dark/metal box enclosure was used to avoid light exposure and to further reduce environmental noise. The dark box had a triax cable feedthrough panel to maintain consistent triax shielding all the way from the preamps to the end of triax probe tips.

Transistor carrier mobilities (pi) were calculated by standard field effect transistor equations. In traditional metal-insulator-semiconductor FETs (MISFETs), there is typically a linear and saturated regime in the $I_{DS}$ vs $V_{DS}$ curves at different $V_G$ (where $I_{DS}$ is the source-drain saturation current, $V_{DS}$ is the potential between the source and drain, and $V_G$ is the gate voltage). At large $V_{DS}$, the current saturates and is given by:

$$(I_{DS})sat = (WC_i/2L)\mu(V_G - V_t)^2 \quad (1)$$

where L and W are the device channel length and width, respectively, $C_i$ is the capacitance of the gate insulator, and $V_t$ is the threshold voltage. Mobilities (μ) were calculated in the saturation regime by rearranging equation (1):

$$\mu_{sat} = (2I_{DS}L)/[WC_i(V_G-V_t)^2] \quad (2)$$

The threshold voltage ($V_t$) can be estimated as the x intercept of the linear section of the plot of $V_G$ versus $(I_{DS})^{1/2}$.

Table 3 summarizes the transistor performance parameters measured under ambient conditions including the field-effect electron and hole mobilities (μ, in saturation unless indicated), current on-to-off ratio ($I_{on}:I_{off}$), and turn-on voltage ($V_{on}$) calculated from $V_g=0$ V to $V_g=+/-60-80$ V.

TABLE 3

| Compound | $\mu_{sat}$ (e−) (cm²/V · s) | $\mu_{sat}$ (h+) (cm²/V · s) | $I_{on}/I_{off}$(e−) | $I_{on}/I_{off}$ (h+) | $V_{on}$(V) |
|---|---|---|---|---|---|
| P(NDI-C5TVT) | 2.3 × 10⁻² | 3.2 × 10⁻³ | 1 × 10² | 1 × 10² | +40, −40 |
| P(C12-BTZ$^{Cl}$-C12-C5TVT) | N/A | 1.0 × 10⁻³ | N/A | 1 × 10³ | N/A, −5 |

Conventional OPVs were fabricated on ITO-covered glass that was cleaned by sonication in soap water, water, acetone and isopropanol followed by storage in a glass oven. Immediately before deposition of the hole-injection layer, the substrates were UV ozone treated for 20 minutes in a JELIGHT UVO Cleaner® 42. An 8-nm film of MoO₃ was deposited onto the ITO thermally under a vacuum of ~10⁻⁶ Torr as the hole-injection layer. Active layers comprising blends of polymer:PC₇₁BM (in embodiments where the present polymer functions as the donor material) or polymer:polymer (in embodiments where the present polymer functions as the acceptor material) at weight ratios varying from 1:4 to 4:1 donor:acceptor, were spin cast from organic solvent solutions (e.g., chloroform:1,2-dichlorobenzene (9:1 by volume)). To complete the device fabrication, 0.6 nm of LiF and 100 nm of aluminum were successively deposited thermally under vacuum of ~10⁻⁶ Torr. The active area of the device was ~0.09 cm². The devices were then encapsulated with a cover glass using EPO-TEK OG112-6 UV curable epoxy (Epoxy Technology) in the glove box.

The photovoltaic characteristics of the encapsulated devices were tested in air. The current density-voltage (J-V) curves were obtained using a Keithley 2400 source-measure unit. The photocurrent was measured under simulated AM1.5G irradiation (100 mW cm⁻²) using a xenon-lamp-based solar simulator (Newport 91160A 300W Class-A Solar Simulator, 2 inch by 2 inch uniform beam) with air mass 1.5 global filter. The light intensity was set using an NREL calibrated silicon photodiode with a color filter.

Table 4 summarizes the OPV performance parameters including the power conversion efficiency (PCE), open circuit voltage (Voc), short circuit current (Jsc) and the fill factor (FF).

TABLE 4

| | Polymer Blend | |
|---|---|---|
| | P(C12-BTZ$^{Cl}$-C12-C5TVT) with a fullerene-based acceptor | P(NDI-C5TVT) with a non-P3HT donor polymer |
| PCE [%] | 0.4 | 0.2 |
| Voc [V] | 0.43 | 0.74 |
| Jsc [mA/cm²] | 2.3 | 0.5 |
| FF | 41.0 | 44.7 |

Inverted OPV cells were fabricated on ITO-covered glass onto which a ZnO film was deposited under vacuum. Active layers comprising blends of P(DPP-C5TVT):PC₇₁BM were spin cast from organic solvent solutions (chloroform, CHCl₃, chlorobenzene, CB, or dichlorobenzene, DCB) with or without diiodooctane, DIO. To complete the device fabrication, MoOx and Ag were successively deposited thermally under vacuum.

Figure 4:
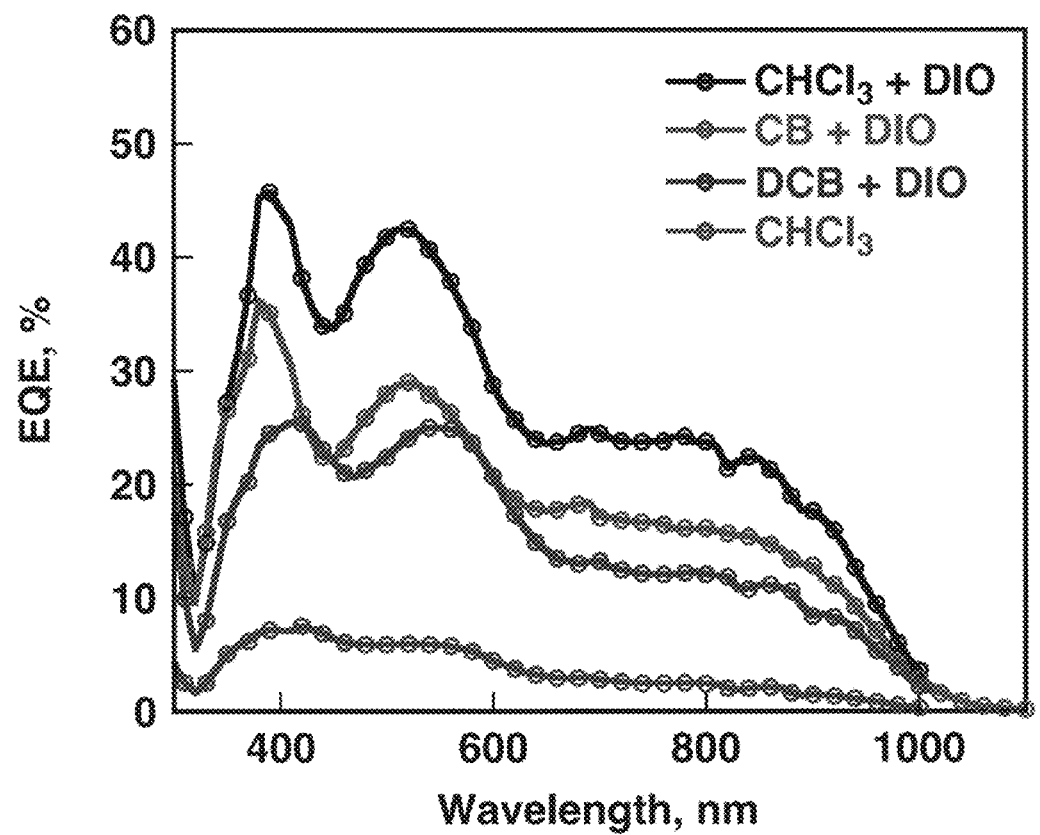
FIG. 4 shows the EQE curves of bulk-heterojunction OPV cells with $PC_{71}BM$ as the acceptor material and a p-type semiconducting polymer according to the present teachings as the donor material.

FIG. 4 provides the EQE curves of the tested OPV cells. As shown, the tested cells showed wide-range EQE up to 1000 nm.

Table 5 summarizes the OPV performance parameters including the power conversion efficiency (PCE), open circuit voltage (Voc), short circuit current (Jsc) and the fill factor (FF).

TABLE 5

| Solvent | $V_{OC}$, V | $J_{SC}$, mA cm$^{-2}$ | FF | PCE, % |
|---|---|---|---|---|
| CHCl$_3$ + DIO | 0.504 | 10.2 | 36.1 | 1.86 |
| CB + DIO | 0.477 | 7.04 | 40.4 | 1.36 |
| DCB + DIO | 0.489 | 4.78 | 39.1 | 0.91 |
| CHCl$_3$ | 0.517 | 1.58 | 48.3 | 0.39 |

All publications, including but not limited to patents and patent applications, cited in this specification are herein incorporated by reference as if each individual publication were specifically and individually indicated to be incorporated by reference herein as though fully set forth.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

The invention claimed is:

1. A polymer comprising as repeating units at least one annulated thienyl-vinylene-thienyl (TVT) unit and at least one other pi-conjugated unit, wherein the annulated TVT unit is selected from the group consisting of:

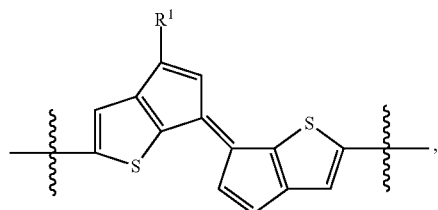

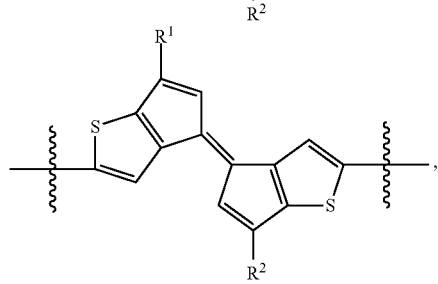

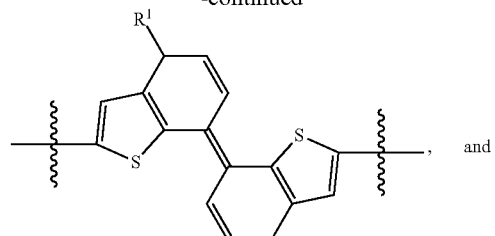

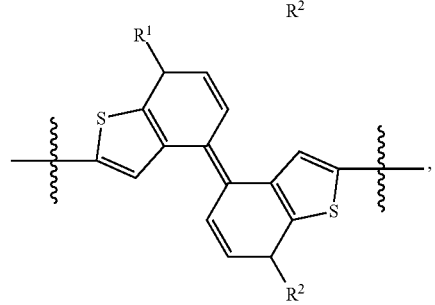

wherein R$^1$ and R$^2$ independently are selected from the group consisting of H, halogen, CN, a C$_{1-40}$ alkyl group, a C$_{2-40}$ alkenyl group, and a C$_{1-40}$ haloalkyl group; and
wherein the other pi-conjugated unit is a conjugated linear linker comprising one or more unsaturated bonds, or a conjugated cyclic linker comprising one or more carbocyclic and/or heterocyclic rings.

2. The polymer of claim 1, wherein the annulated TVT unit is:

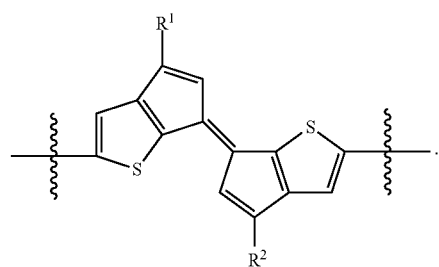

3. The polymer of claim 2, wherein the annulated TVT unit is present in a first repeating unit of the formula:

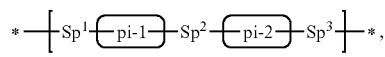

wherein:
pi-1 is the annulated TVT unit;
pi-2 is a covalent bond or an optionally substituted conjugated polycyclic moiety; and
Sp$^1$, Sp$^2$, and Sp$^3$ independently are a covalent bond or a conjugated spacer group comprising at least one of a conjugated linear linker and an optionally substituted conjugated monocyclic moiety;
provided at least one of pi-2, Sp$^1$, Sp$^2$, and Sp$^3$ is not a covalent bond.

4. The polymer of claim 3, wherein Sp$^1$, Sp$^2$, and Sp$^3$ independently are selected from the group consisting of:

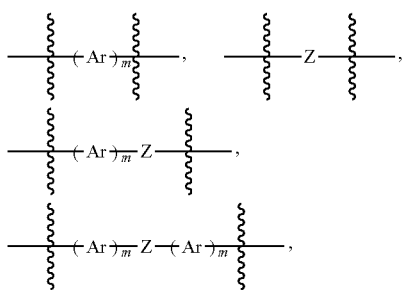

and a covalent bond, wherein each Ar independently is an optionally substituted conjugated monocyclic moiety; Z is a conjugated linear linker; and m is 1, 2, 3, 4 or 5.

5. The polymer of claim 4, wherein each Ar independently is a monocyclic 5- or 6-membered aryl or heteroaryl group optionally substituted with 1-4 $R^3$ groups, wherein each $R^3$ independently is selected from the group consisting of a halogen, CN, oxo, $=C(CN)_2$, a $C_{1-40}$ alkyl group, a $C_{1-40}$ haloalkyl group, a $C_{1-40}$ alkoxy group, and a $C_{1-40}$ alkylthio group.

6. The polymer of claim 4, wherein Z is selected from the group consisting of:

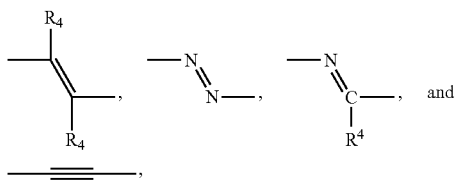

wherein each $R^4$ independently is selected from the group consisting of H, a halogen, CN, a $C_{1-40}$ alkyl group, a $C_{1-40}$ haloalkyl group, a $C_{1-40}$ alkoxy group, and a $C_{1-40}$ alkylthio group.

7. The polymer of claim 4, wherein pi-2 is a conjugated polycyclic moiety selected from the group consisting of:

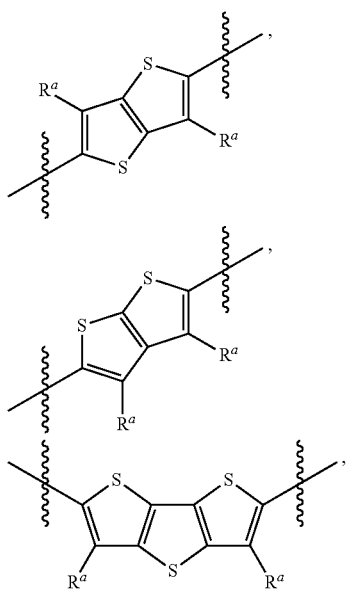

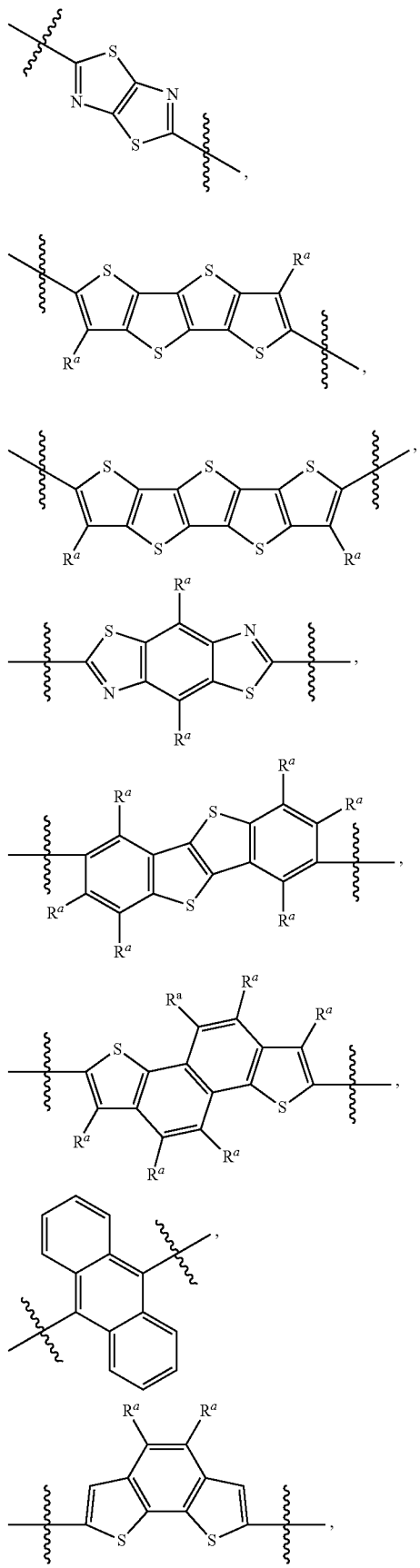

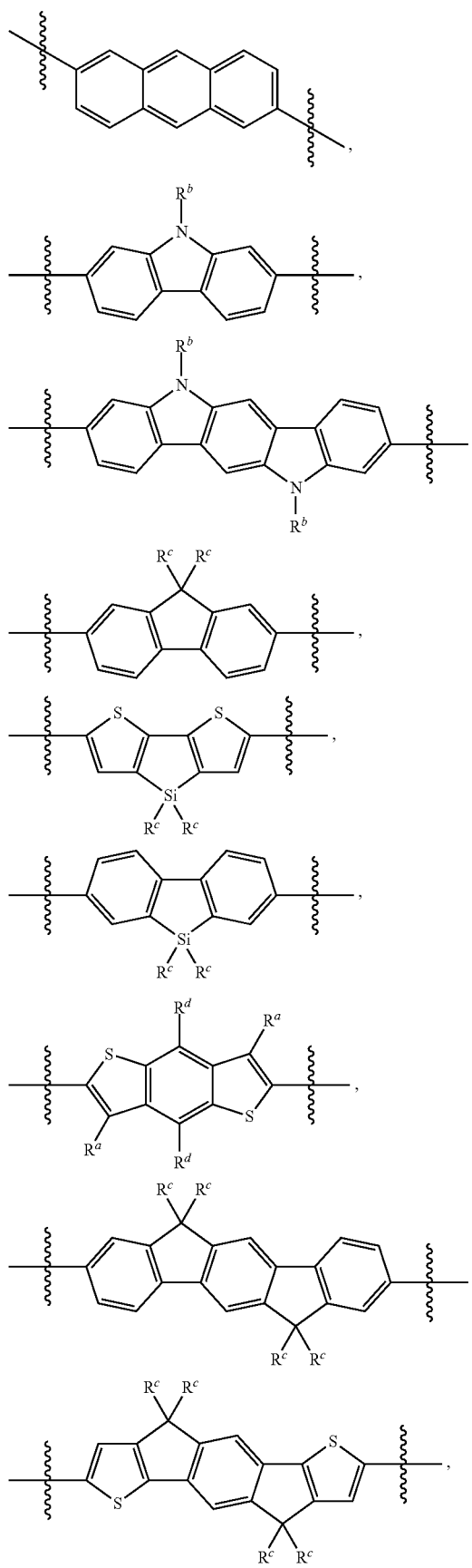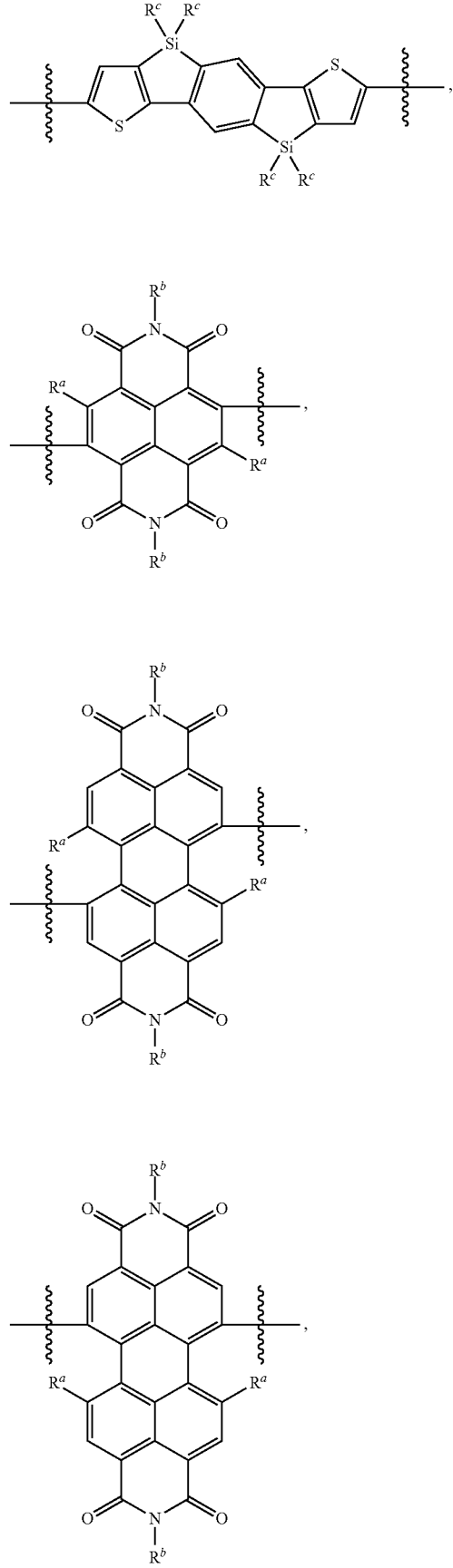

-continued
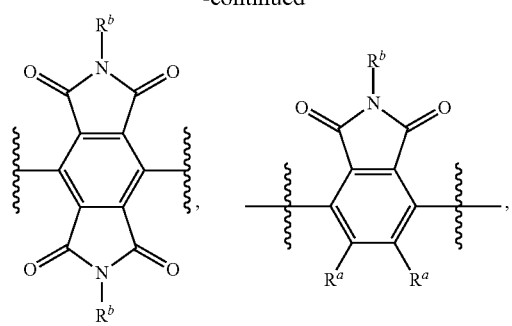
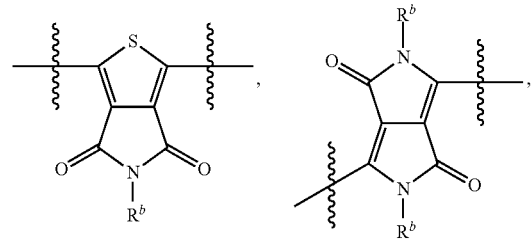
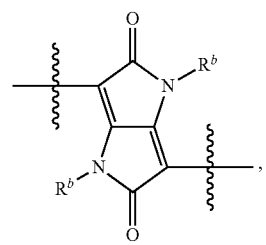
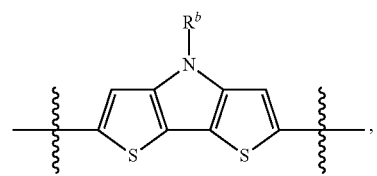
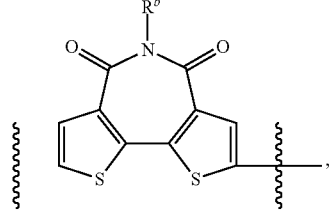
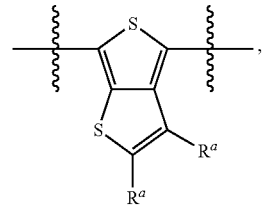
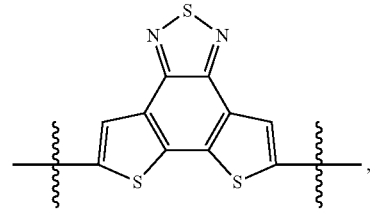
-continued
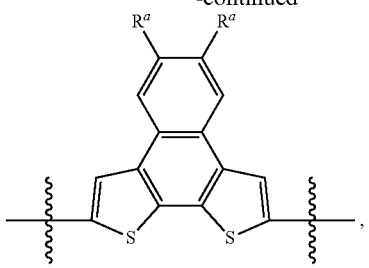
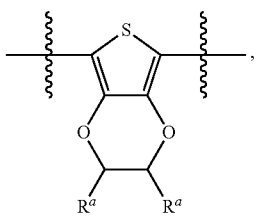
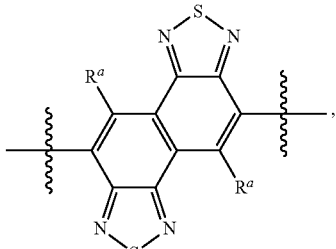
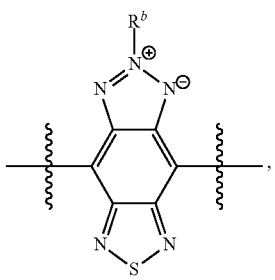
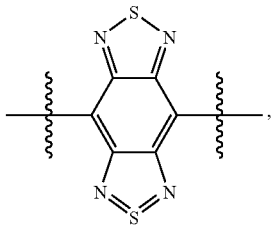
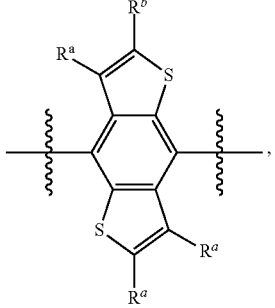

-continued

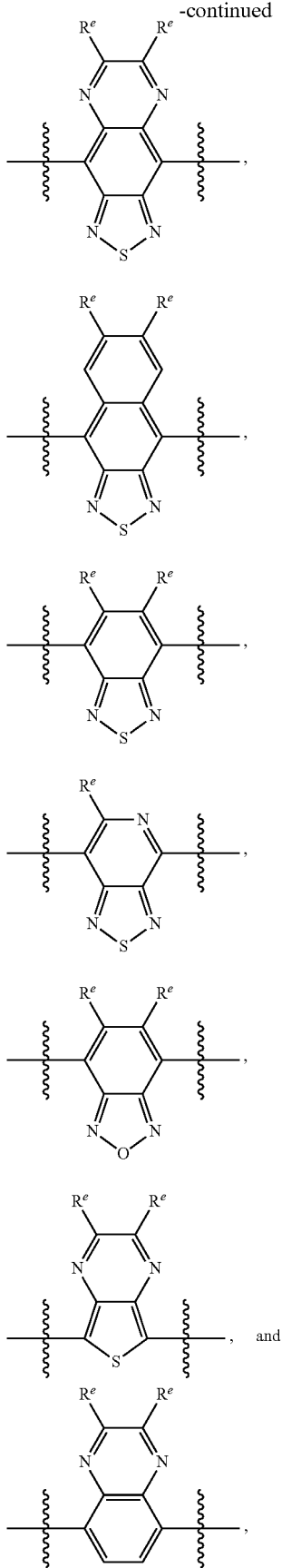

wherein:
$R^a$ is selected from the group consisting of H, F, Cl, —CN, R, —OR, —SR, —C(O)R, —OC(O)R, and —C(O)OR;

$R^b$ is selected from the group consisting of H, R, and -L-$R^f$;

$R^c$ is H or R;

$R^d$ is selected from the group consisting of H, F, Cl, —CN, R, —OR, —SR, —C(O)R, —OC(O)R, —C(O)OR, and -L-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group.

8. The polymer of claim 3 having a formula selected from the group consisting of

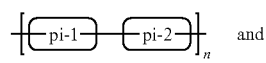 and

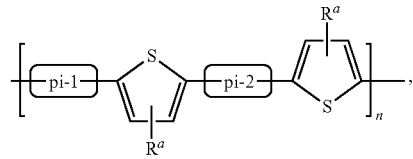

wherein:
$R^a$ is selected from the group consisting of H, F, Cl, —CN, R, —OR, —SR, —C(O)R, —OC(O)R, and —C(O)OR, where R is selected from the group consisting of a $C_{1-40}$ alkyl group, a $C_{1-40}$ haloalkyl group, a $C_{2-40}$ alkenyl group, and a $C_{2-40}$ alkynyl group; and n is an integer in the range of 3 and 5,000.

9. The polymer of claim 8, wherein pi-2 is selected from the group consisting of:

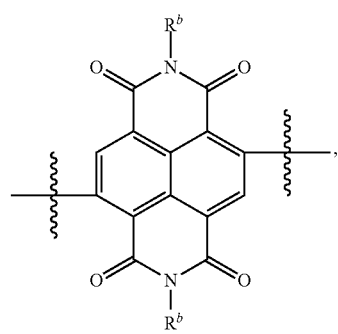

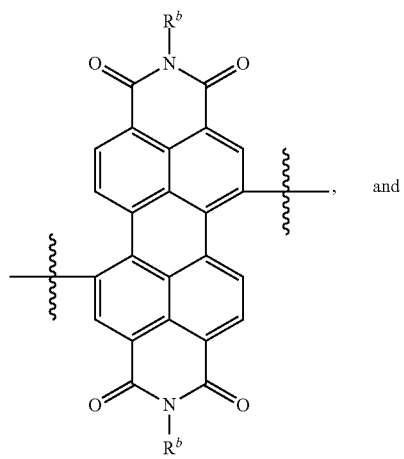
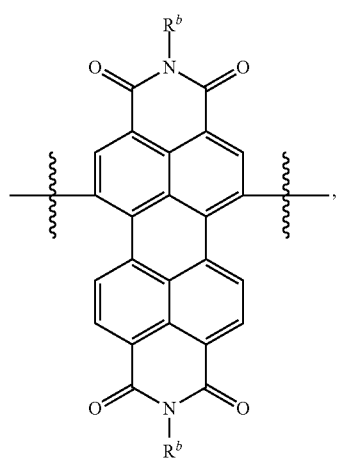
wherein $R^b$ is a linear or branched $C_{1-40}$ alkyl, $C_{1-40}$ haloalkyl, $C_{2-40}$ alkenyl, or $C_{2-40}$ alkynyl group.
10. The polymer of claim 8, wherein pi-2 is selected from the group consisting of:
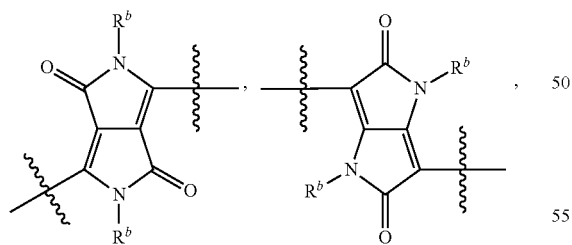
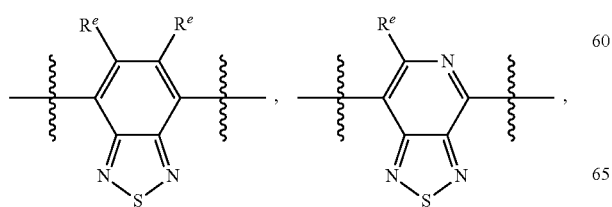
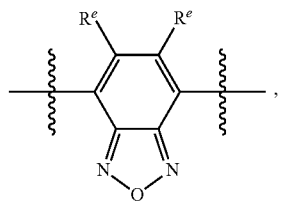
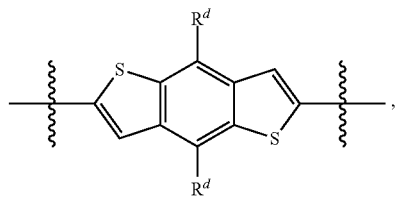
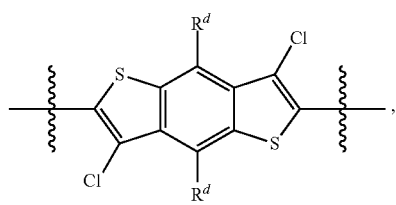
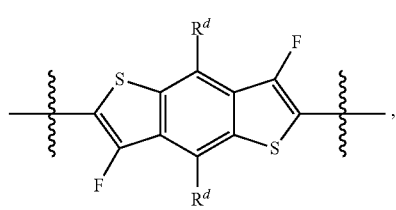
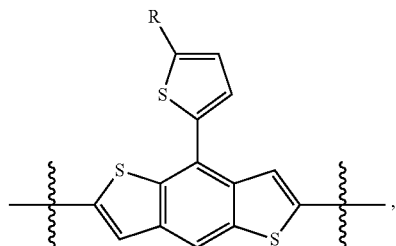
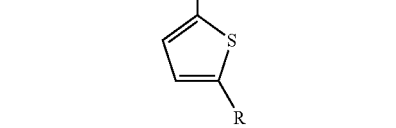
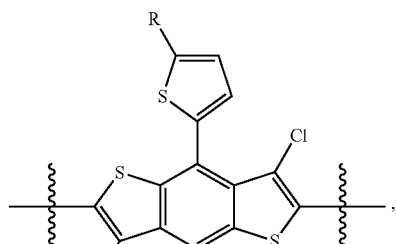
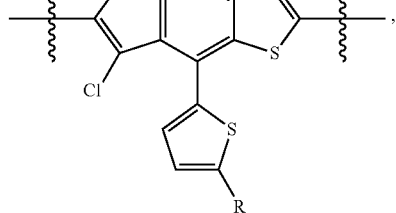, and -continued

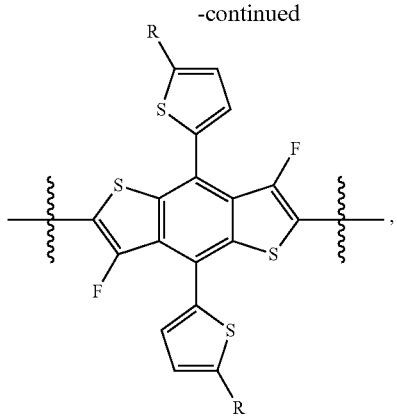

wherein $R^b$ is a linear or branched $C_{1-40}$ alkyl, $C_{1-40}$ haloalkyl, $C_{2-40}$ alkenyl, or $C_{2-40}$ alkynyl group; $R^d$ is selected from R, OR, and SR; R is a linear or branched $C_{1-40}$ alkyl, $C_{1-40}$ haloalkyl, $C_{2-40}$ alkenyl, or $C_{2-40}$ alkynyl group; and $R^e$ is selected from the group consisting of H, F, and Cl.

11. The polymer of claim 3, wherein the polymer comprises a second repeating unit different from the first repeating unit and the second repeating unit has the formula:

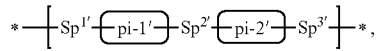

wherein:

pi-1' is selected from the group consisting of:

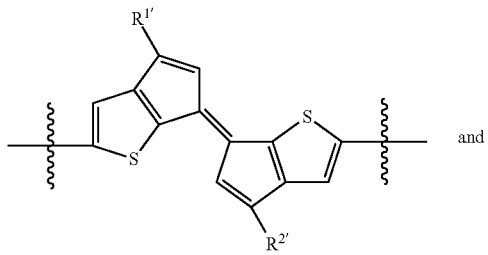

-continued

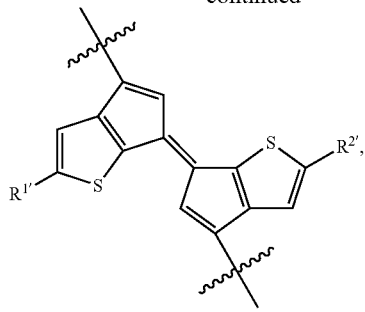

wherein $R^{1'}$ and $R^{2'}$ independently are selected from the group consisting of H, halogen, CN, a $C_{1-40}$ alkyl group, a $C_{2-40}$ alkenyl group, and a $C_{1-40}$ haloalkyl group;

pi-2' is a covalent bond or an optionally substituted conjugated polycyclic moiety; and each of $Sp^{1'}$, $Sp^{2'}$, and $Sp^{3'}$ independently is a covalent bond or a conjugated spacer group having a formula selected from the group consisting of:

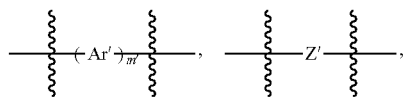

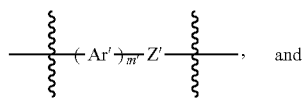

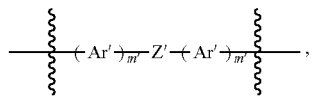

wherein each Ar' independently is an optionally substituted conjugated monocyclic moiety; Z' is a conjugated linear linker; and m' is 1, 2, 3 or 4.

12. The polymer of claim 11, wherein the first repeating unit and the second repeating unit are arranged in an alternating manner.

13. The polymer of claim 11, where the first repeating unit and the second repeating unit are arranged in a random manner.

14. The polymer of claim 11 having the formula:

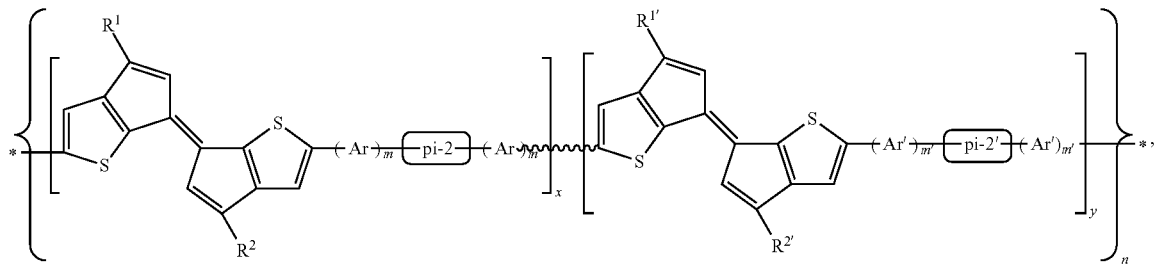

wherein n is an integer in the range of 3 to 5,000; x and y are real numbers representing mole fractions, wherein 0.05≤x≤0.95, 0.05≤y≤0.95, and the sum of x and y is 1; and provided Ar is different from Ar', or $R^1$ and $R^2$ are different from $R^{1'}$ and $R^{2'}$, or pi-2 is different from pi-2', or m is different from m'.

15. The polymer of claim 14 having the formula:

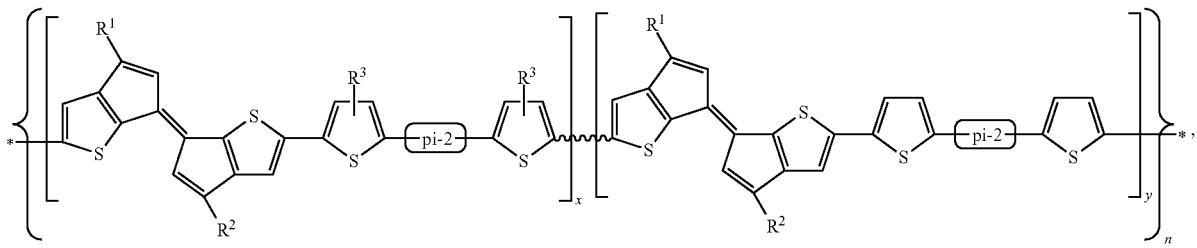

wherein:
- each $R^1$ and $R^2$ independently are selected from the group consisting of H, halogen, CN, a $C_{1-40}$ alkyl group, a $C_{2-40}$ alkenyl group, and a $C_{1-40}$ haloalkyl group;
- each $R^3$ independently is selected from the group consisting of R, OR, and SR;
- pi-2 is a conjugated polycyclic moiety selected from the group consisting of:

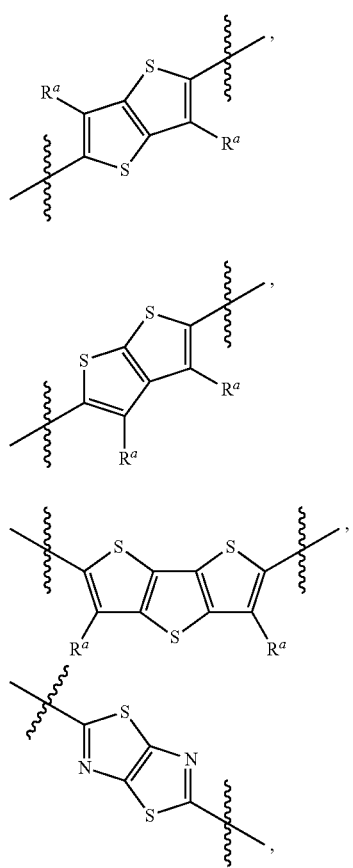

-continued

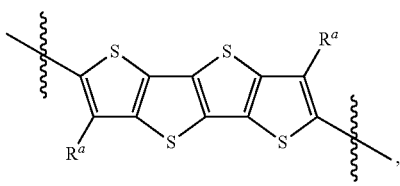

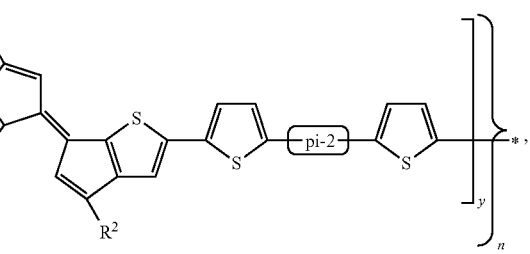

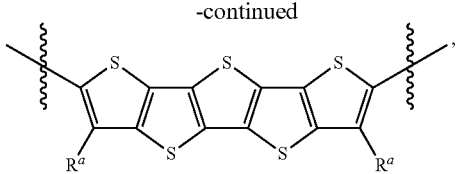

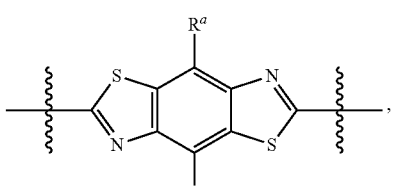

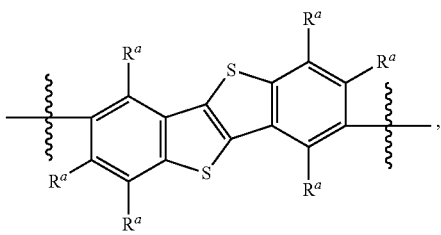

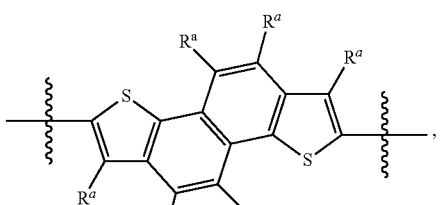

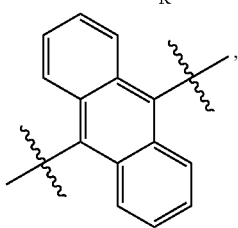

-continued
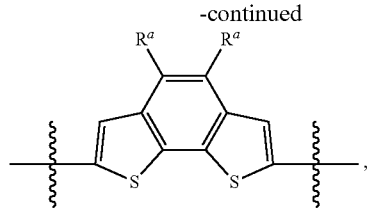
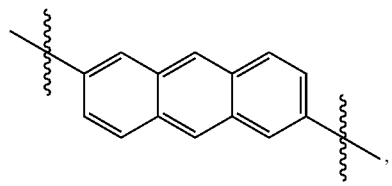
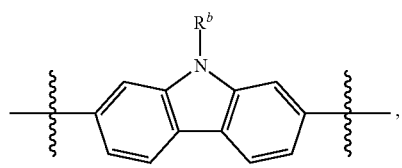
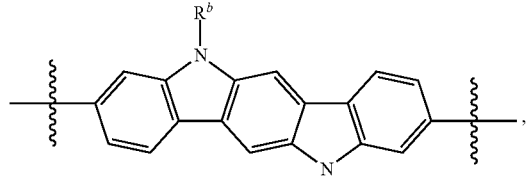
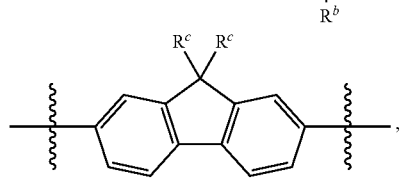
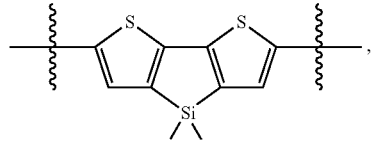
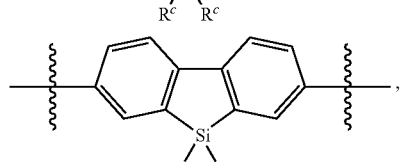
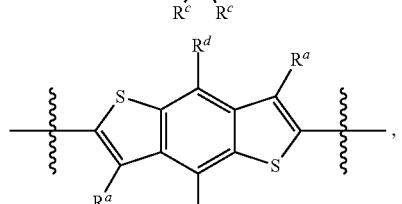
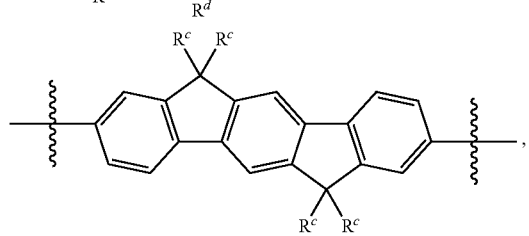
-continued
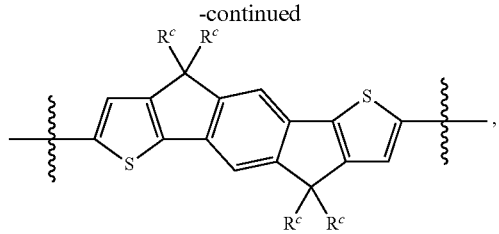
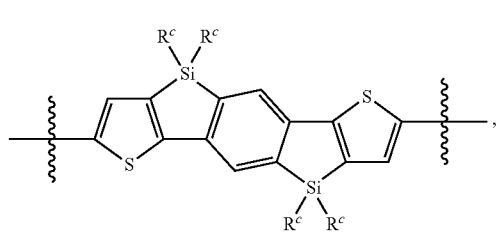
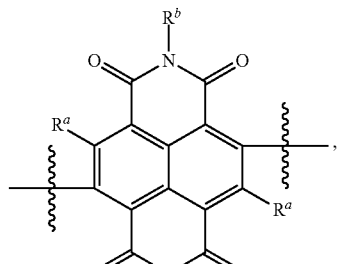
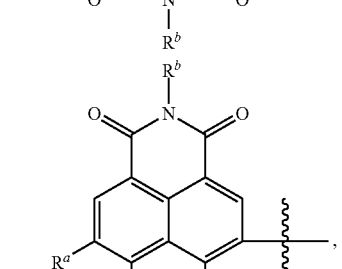
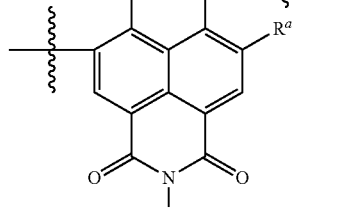
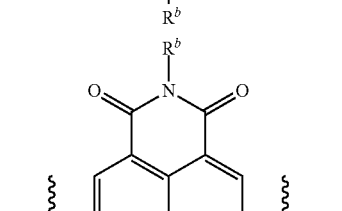
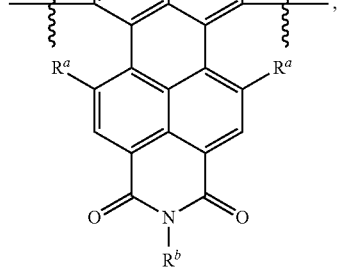

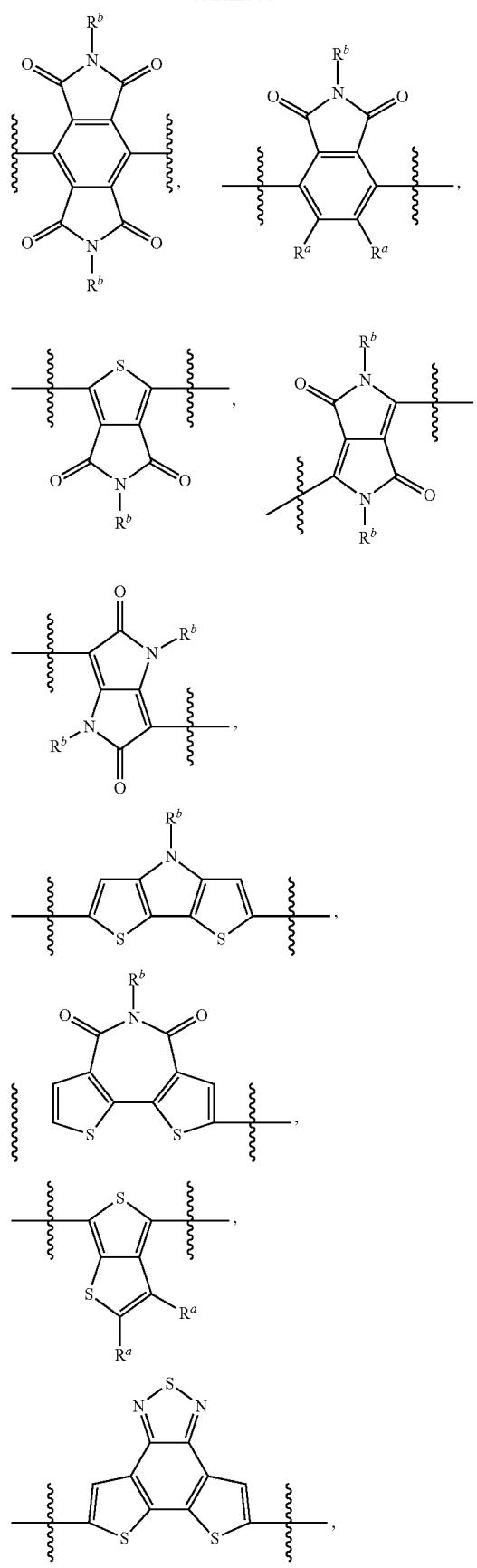
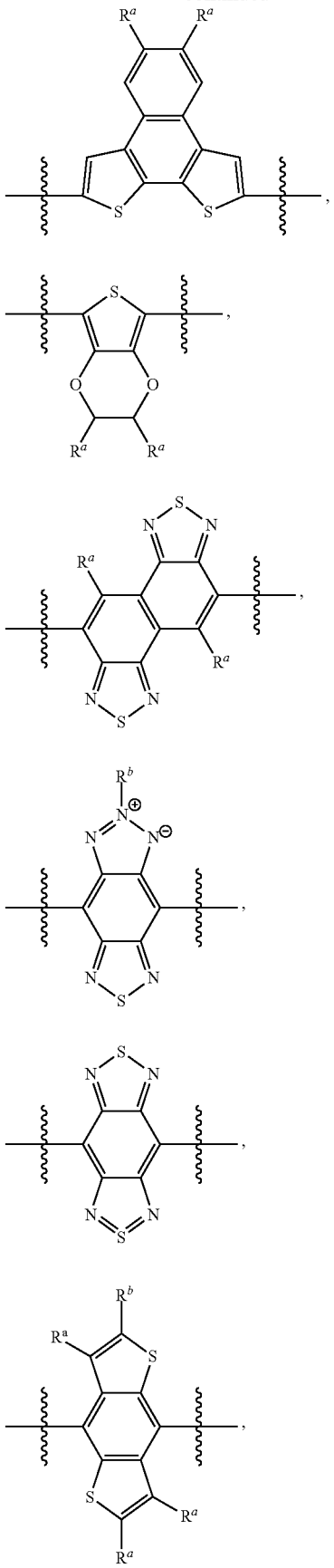

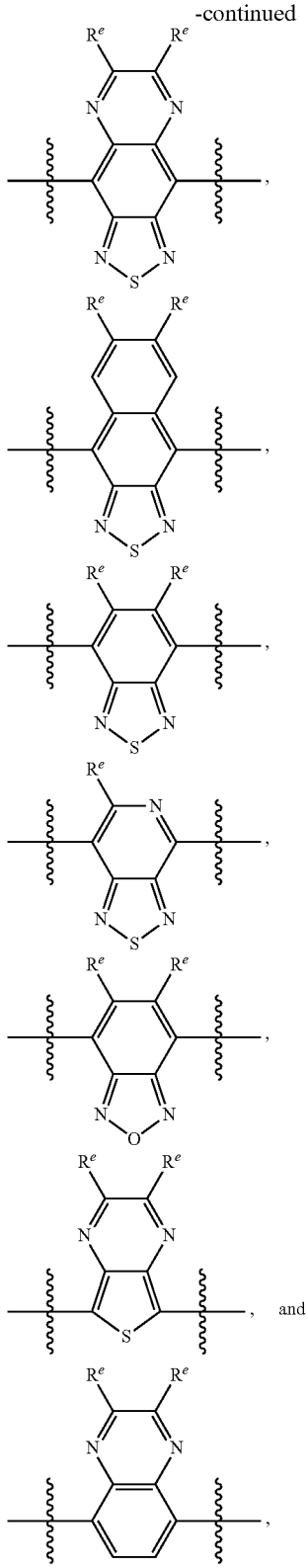

wherein:

$R^a$ is selected from the group consisting of H, F, Cl, —CN, R, —OR, —SR, —C(O)R, —OC(O)R, and —C(O)OR;

$R^b$ is selected from the group consisting of H, R, and -L-$R^f$;

$R^c$ is H or R;

$R^d$ is selected from the group consisting of H, F, Cl, —CN, R, —OR, —SR, —C(O)R, —OC(O)R, —C(O)OR, and -L-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group;

n is an integer in the range of 2 to 10,000;

x and y are real numbers representing mole fractions, wherein $0.05 \leq x \leq 0.95$, $0.05 \leq y \leq 0.95$, and the sum of x and y is 1.

16. An organic thin film transistor comprising a polymeric semiconductor component, the polymeric semiconductor component comprising the polymer of claim 2.

17. An organic photovoltaic device comprising an anode, a cathode, optionally one or more anode interlayers, optionally one or more cathode interlayers, and in between the anode and the cathode a polymeric semiconductor component comprising a blend material, the blend material comprising an electron-acceptor compound and an electron-donor compound, the electron-donor compound being the polymer of claim 2.

18. The device of claim 17, wherein the electron-acceptor compound is a fullerene compound.

19. An organic photovoltaic device comprising an anode, a cathode, optionally one or more anode interlayers, optionally one or more cathode interlayers, and in between the anode and the cathode a polymeric semiconductor component comprising a blend material, the blend material comprising an electron-acceptor compound and an electron-donor compound, the electron-acceptor compound being the polymer of claim 2.

20. The device of claim 17, wherein the electron-acceptor compound is an electron-transporting polymer.

* * * * *